United States Patent
Scott et al.

(10) Patent No.: US 8,167,793 B2
(45) Date of Patent: May 1, 2012

(54) AUGMENTED STEREOSCOPIC VISUALIZATION FOR A SURGICAL ROBOT USING TIME DUPLEXING

(75) Inventors: David Scott, Oakland, CA (US); Wenyi Zhao, Mountain View, CA (US); Christopher J. Hasser, Los Altos, CA (US); Brian D. Hoffman, Sunnyvale, CA (US); Ian McDowall, Woodside, CA (US); Catherine J. Mohr, Mountain View, CA (US); John D. Stern, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 834 days.

(21) Appl. No.: 12/165,189

(22) Filed: Jun. 30, 2008

(65) Prior Publication Data

US 2009/0270678 A1      Oct. 29, 2009

Related U.S. Application Data

(60) Provisional application No. 61/048,179, filed on Apr. 26, 2008.

(51) Int. Cl.
   *A61B 1/06*   (2006.01)
   *A61B 1/04*   (2006.01)
   *A61B 1/00*   (2006.01)
(52) U.S. Cl. .................. 600/160; 600/109; 600/166
(58) Field of Classification Search .............. 348/67–68, 348/70; 600/101, 108–109, 178, 180, 181
   See application file for complete search history.

(56) References Cited

U.S. PATENT DOCUMENTS

| | | | |
|---|---|---|---|
| 4,541,438 A | 9/1985 | Parker et al. | 128/664 |
| 4,556,057 A | 12/1985 | Hiruma et al. | 128/303.1 |
| 4,821,117 A | 4/1989 | Sekiguchi | 358/98 |
| 4,930,516 A | 6/1990 | Alfano et al. | 128/665 |
| 5,092,331 A | 3/1992 | Nakamura et al. | 128/634 |
| 5,507,287 A | 4/1996 | Palcic et al. | 128/633 |
| 5,590,660 A | 1/1997 | MacAulay et al. | 128/664 |
| 5,749,830 A * | 5/1998 | Kaneko et al. | 600/160 |
| 5,769,792 A | 6/1998 | Palcic et al. | 600/477 |

(Continued)

FOREIGN PATENT DOCUMENTS

EP      1 762 183 A1      3/2007

(Continued)

OTHER PUBLICATIONS

PCT/US09/40020 International Search Report and Written Opinion of the International Searching Authority, mailed Sep. 2, 2009, 11 pages.

(Continued)

*Primary Examiner* — Philip R Smith

(57) ABSTRACT

An endoscope with a stereoscopic optical channel is again held and positioned by a robotic surgical system. A capture unit captures (1) at a first time, a first image from light from the channel; and (2) at a second time different from the first time, a second image from the light. Only one of the first image and the second image includes a combination of a fluorescence image and a visible image. The other of the first image and the second image is a visible image. An intelligent image processing system generates an artificial fluorescence image using the captured fluorescence image. An augmented stereoscopic display system outputs an augmented stereoscopic image of at least a portion of the tissue comprising the artificial fluorescence image.

21 Claims, 29 Drawing Sheets

U.S. PATENT DOCUMENTS

| | | | |
|---|---|---|---|
| 5,827,190 A | 10/1998 | Palcic et al. | 600/476 |
| 6,468,204 B2* | 10/2002 | Sendai et al. | 600/160 |
| 6,635,011 B1* | 10/2003 | Ozawa et al. | 600/178 |
| 7,170,677 B1 | 1/2007 | Bendall et al. | |
| 7,172,553 B2* | 2/2007 | Ueno et al. | 600/160 |
| 7,179,222 B2* | 2/2007 | Imaizumi et al. | 600/109 |
| 7,253,894 B2 | 8/2007 | Zeng et al. | 356/326 |
| 7,341,557 B2 | 3/2008 | Cline et al. | 600/160 |
| 2002/0022766 A1* | 2/2002 | Adachi | 600/160 |
| 2002/0026099 A1* | 2/2002 | Adachi et al. | 600/178 |
| 2004/0162492 A1* | 8/2004 | Kobayashi | 600/476 |
| 2005/0288553 A1 | 12/2005 | Sugimoto | |
| 2005/0288556 A1* | 12/2005 | Sugimoto | 600/160 |
| 2006/0020169 A1* | 1/2006 | Sugimoto | 600/180 |
| 2006/0052710 A1 | 3/2006 | Miura et al. | 600/476 |
| 2006/0256191 A1 | 11/2006 | Iketani et al. | |
| 2008/0097198 A1 | 4/2008 | Miwa et al. | 600/431 |
| 2008/0239070 A1* | 10/2008 | Westwick et al. | 348/68 |

FOREIGN PATENT DOCUMENTS

| | | |
|---|---|---|
| JP | 21204683 A2 | 7/2001 |
| JP | 23093339 A2 | 4/2003 |
| JP | 2007143624 A | 6/2007 |
| WO | WO-03059150 A2 | 7/2003 |

OTHER PUBLICATIONS

Vertut, Jean et al., *Robot Technology: Teleoperation and Robotics Evolution and Development*, 1986, vol. 3A, English translation Prentice-Hall, Inc., Inglewood Cliffs, NJ, USA, 332 pages.

\* cited by examiner

AUGMENTED STEREOSCOPIC VISUALIZATION FOR A SURGICAL ROBOT USING TIME DUPLEXING

RELATED APPLICATION

This application claims the benefit of:

U.S. Provisional Application No. 61/048,179 filed Apr. 26, 2008 entitled "AUGMENTED STEREOSCOPIC VISUALIZATION FOR A SURGICAL ROBOT," naming as inventors, Wenyi Zhao, Catherine J. Mohr, Christopher J. Hasser, David D. Scott, John D. Stern, Paul Lilagan, Simon P. DiMaio, Tao Zhao, Gregory W. Dachs, David C. Shafer, and Brian D. Hoffman, which is incorporated herein by reference in its entirety.

This application may be related to the following commonly assigned and commonly filed U.S. Patent Applications, each of which is incorporated herein by reference in its entirety:

1. U.S. patent application Ser. No. 12/164,363 entitled "AUGMENTED STEREOSCOPIC VISUALIZATION FOR A SURGICAL ROBOT," naming as inventors, David D. Scott et al., filed on Jun. 30, 2008;
2. U.S. patent application Ser. No. 12/164,976 entitled "AUGMENTED STEREOSCOPIC VISUALIZATION FOR A SURGICAL ROBOT USING A CAPTURED FLUORESCENCE IMAGE AND CAPTURED STEREOSCOPIC VISIBLE IMAGES," naming as inventors, Wenyi Zhao et al., filed on Jun. 30, 2008;
3. U.S. patent application Ser. No. 12/165,194 entitled "AUGMENTED STEREOSCOPIC VISUALIZATION FOR A SURGICAL ROBOT USING A CAPTURED VISIBLE IMAGE COMBINED WITH A FLUORESCENCE IMAGE AND A CAPTURED VISIBLE IMAGE," naming as inventors, David D. Scott et al., filed on Jun. 30, 2008; and
4. U.S. patent application Ser. No. 12/165,121 entitled "AUGMENTED STEREOSCOPIC VISUALIZATION FOR A SURGICAL ROBOT USING A CAMERA UNIT WITH A MODIFIED PRISM," naming as inventors, David D. Scott et al., filed on Jun. 30, 2008.

BACKGROUND

1. Field of Invention

Aspects of this invention are related to endoscopic imaging, and are more particularly related to blending visible and alternate images so as to provide an enhanced real-time video display for a surgeon.

2. Art

The da Vinci® Surgical System, manufactured by Intuitive Surgical, Inc., Sunnyvale, Calif., is a minimally invasive, teleoperated robotic system that offers patients many benefits, such as reduced trauma to the body, faster recovery and shorter hospital stay. One key component of the da Vinci® Surgical System is a capability to provide two-channel (i.e., left and right) video capture and display of three-dimensional (3D) visible images that provides stereoscopic viewing for the surgeon.

Such electronic stereoscopic imaging systems may output high definition video images to the surgeon, and may allow features such as zoom to provide a "magnified" view that allows the surgeon to identify specific tissue types and characteristics, as well as to work with increased precision. In a typical surgical field, however, certain tissue types are difficult to identify, or tissue of interest may be at least partially obscured by other tissue.

SUMMARY OF THE INVENTION

In one aspect, a robotic surgical system positions and holds an endoscope. A visible imaging system is coupled to the endoscope. The visible imaging system captures a visible image of tissue. An alternate imaging system is also coupled to the endoscope. The alternate imaging system captures a fluorescence image of at least a portion of the tissue. A stereoscopic video display system is coupled to the visible imaging system and to the alternate imaging system. The stereoscopic video display system outputs a real-time stereoscopic image comprising a three-dimensional presentation of a blend of a fluorescence image associated with the captured fluorescence image, and the visible image.

Thus, the stereoscopic video capturing and viewing capability of surgical robots is augmented by incorporating both stereoscopic visible images and stereoscopic alternate imaging modality images to identify, in real-time during surgery, tissue of clinical interest.

Aspects of the invention simultaneously provide stereoscopic alternate modality images that identify tissue of clinical interest in addition to stereoscopic visible images that a surgeon normally uses when performing a surgical operation using a teleoperated surgical system. This combination of stereoscopic visible and alternate images provides benefits including, but not limited to, allowing a surgeon in real-time to identify positive tumor margins for diseased tissue excision and to identify nerves so as to avoid cutting those nerves.

This imaging combination may be a continuous overlay of the stereoscopic visible and alternate images, or the overlay of stereoscopic alternate images may be toggled on and off. Also, the real-time three-dimensional blend of the visible image and the another fluorescence image is presented in only one eye of the stereoscopic image in one aspect.

In another aspect, the visible imaging system captures the visible image at a first frame rate, while the alternate imaging system captures the fluorescence image at a second frame rate. The first frame rate is different from the second frame rate. The alternate imaging system provides fluorescence images to the stereoscopic video display system at the first frame rate by generating artificial fluorescence images to synchronize the fluorescence images with the visible images.

Thus, in one aspect, a method includes capturing, from an endoscope held by and positioned by a robotic manipulator arm of a robotic surgical system, a visible image of tissue. This method also captures, from the endoscope, an alternate image of at least a portion of the tissue. The alternate image comprises a fluorescence image. In this method, a blend of another fluorescence image associated with the captured fluorescence image and the visible image are output in a real-time stereoscopic video display.

In another aspect, the method generates a second fluorescence image using information associated with the captured fluorescence image. The second fluorescence image is the another fluorescence image.

In still another aspect, the method generates a second visible image using information associated with the visible image. The visible image and the second visible image comprise a stereoscopic pair of visible images. In this aspect, the method also generates a second fluorescence image using information associated with the fluorescence image. The second fluorescence image is the another fluorescence image.

In one aspect, an illumination channel is held and positioned by a robotic surgical system. Light from the illumination channel illuminates tissue. A stereoscopic optical channel is also, held and positioned by the robotic surgical system. The stereoscopic optical channel transports first light from the tissue. Another optical channel also is held and positioned by the robotic surgical system. This optical channel transports second light from the tissue. The stereoscopic optical channel is different from the another optical channel.

An image capture system includes a first capture unit coupled to the stereoscopic optical channel. The first capture unit captures a stereoscopic visible image from the first light. The image capture system also includes a second capture unit coupled to the another optical channel. The second capture unit captures a fluorescence image from the second light.

An intelligent image processing system is coupled to the first capture unit and to the second capture unit. The intelligent image processing system receives the captured stereoscopic visible image and the captured fluorescence image. The intelligent image processing system generates a stereoscopic pair of fluorescence images.

An augmented stereoscopic display system is coupled to the intelligent image processing system, and to the image capture system. The augmented stereoscopic display system outputs a real-time stereoscopic image comprising a three-dimensional presentation of a blend of the stereoscopic visible image and the stereoscopic pair of fluorescence images.

In another aspect, a method includes capturing a stereoscopic visible image of tissue from a stereoscopic optical path held and positioned by a robotic surgical system. This method also captures a fluorescence image of the tissue from another optical channel held and positioned by the robotic surgical system. The stereoscopic optical channel is different from the another optical channel.

The method processes the captured fluorescence image using information from the captured stereoscopic visible image to generate a stereoscopic pair of fluorescence images. A real-time augmented stereoscopic image of the tissue comprising a three-dimensional presentation of a blend of the stereoscopic visible image and the stereoscopic pair of fluorescence images is generated.

In one aspect, an endoscope is held and positioned by a robotic surgical system. The endoscope includes a stereoscopic optical channel, which has a first channel for transporting first light from tissue and a second channel for transporting second light from the tissue.

A first capture unit is coupled to the first channel. The first capture unit captures: a visible first color component of a visible left image combined with a fluorescence left image from the first light; a visible second color component of the visible left image from the first light; and a visible third color component of the visible left image from the first light.

A second capture unit is coupled to the second channel. The second capture unit captures: a visible first color component of a visible right image combined with a fluorescence right image from the second light; a visible second color component of the visible right image from the second light; and a visible third color component of the visible right image from the second light. The two capture units are included in an image capture system.

An augmented stereoscopic display system is coupled to the image capture system. The augmented stereoscopic display system outputs a real-time stereoscopic image of at least a portion of the tissue. The real-time stereoscopic image includes a three-dimensional presentation including the visible left and right images and the fluorescence left and right images.

The first capture unit includes a prism. The prism separates the first light into (1) the visible first color component of the visible left image, (2) the visible second color component of the visible left image, (3) the third color component visible left image, and (4) a fourth component separated and removed from the first, second, and third color components and having a color of the first color component wherein the fourth component is the fluorescence left image. The second capture unit includes a similar prism in one aspect.

In still yet another aspect, a method captures a visible first color component of a visible left image of tissue combined with a fluorescence left image of at least a portion of the tissue from a stereoscopic optical path in an endoscope held and positioned by a robotic surgical system. The method also captures a visible second color component of the visible left image from the stereoscopic optical path; a visible third color component of the visible left image from the stereoscopic optical path; a visible first color component of a visible right image of the tissue combined with a fluorescence right image of at least a portion of the tissue from the stereoscopic optical path in an endoscope held and positioned by a robotic surgical system; a visible second color component of the visible right image from the stereoscopic optical path; and a visible third color component of the visible right image from the stereoscopic optical path.

The method generates a real-time augmented stereoscopic image of the tissue. The real-time augmented stereoscopic image includes a three-dimensional presentation including the visible left and right images and the fluorescence left and right images.

This method uses a prism to separate light from the stereoscopic optical path into (1) the visible first color component, (2) the visible second color component, (3) the visible third color component, and (4) a fourth component separated and removed from the first, second, and third color components and having a color of the first color component. The fourth component is the fluorescence image.

In one aspect, an endoscope also is held and positioned by a robotic surgical system. The endoscope includes a stereoscopic optical channel for transporting light from tissue. A capture unit is coupled to the stereoscopic optical channel. The capture unit captures (1) a visible first image and (2) a visible second image combined with a fluorescence second image from the light. The first image is one of a left image and a right image. The second image is the other of the left image and the right image.

An intelligent image processing system is coupled to the capture unit to receive (1) the visible first image and (2) the visible second image combined with the fluorescence second image. The intelligent image processing system generates at least one fluorescence image of a stereoscopic pair of fluorescence images and a visible second image.

An augmented stereoscopic display system is coupled to the intelligent image processing system, and to the image capture system. The augmented stereoscopic display system outputs a real-time stereoscopic image including a three-dimensional presentation. The three-dimensional presentation includes in one eye, a blend of the at least one fluorescence image of a stereoscopic pair of fluorescence images and one of the visible first and second images; and in the other eye, the other of the visible first and second images.

In yet a further aspect, a method captures a visible first image of tissue from a stereoscopic optical path in an endoscope held and positioned by a robotic surgical system. The method also captures a visible second image combined with a fluorescence second image of the tissue from the stereoscopic optical path in the endoscope held and positioned by the robotic surgical system. The first image is one of a left image and a right image. The second image is the other of the left image and the right image.

The method processes the visible first image and the visible second image combined with the fluorescence second image to generate at least one fluorescence image of a stereoscopic pair of fluorescence images and a visible second image. A real-time stereoscopic image comprising a three-dimensional presentation is generated. The three-dimensional presentation includes: in one eye, a blend of the at least one fluorescence image of a stereoscopic pair of fluorescence images and one of the visible first and second images; and in the other eye, an other of the visible first and second images.

In one aspect, an endoscope is again held and positioned by a robotic surgical system. The endoscope includes a stereoscopic optical channel for transporting light from tissue. A capture unit is coupled to the stereoscopic optical channel.

The capture unit captures (1) at a first time, a first image from the light; and (2) at a second time different from the first time, a second image from the light. Only one of the first image and the second image includes a combination of a fluorescence image and a visible image. The other of the first image and the second image is a visible image.

An intelligent image processing system is coupled to the capture unit. The intelligent image processing system generates an artificial fluorescence image using the captured fluorescence image. An augmented stereoscopic display system is coupled to the intelligent image processing system. The augmented stereoscopic display system outputs an augmented stereoscopic image of at least a portion of the tissue comprising the artificial fluorescence image.

In one aspect, the fluorescence image includes a fluorescence left image and a fluorescence right image. The first image comprises a stereoscopic pair of images including: a visible left image combined with the fluorescence left image: and a visible right image combined with the fluorescence right image. The robotic surgical system generates an artificial stereoscopic pair of fluorescence images for the second time using the fluorescence left and right images so that the artificial stereoscopic pair of fluorescence images are the artificial fluorescence image. The intelligent image processing system also includes temporal image registration for registering the first image and the second image.

In another aspect, the first image includes a visible image which in turn includes a visible first color component, a visible second color component, and a visible third color component. The second image includes a visible image combined with a fluorescence image including: a visible first color component combined with the fluorescence image, a visible second color component and a visible third color component. The intelligent image processing system further comprises a fluorescence image and artifacts generator to generate (1) artifacts for the visible second and third color components, and (2) the fluorescence image plus artifacts for the visible first color component.

In this aspect, the intelligent image processing system also includes a fluorescence image extractor coupled to the fluorescence image and artifacts generator. The fluorescence image extractor generates a first fluorescence image for the second time. A fluorescence image enhancement system is coupled to the fluorescence image generator. The fluorescence image enhancement system receives the first fluorescence image and generates the artificial fluorescence image.

In still yet a further aspect, a method includes capturing at a first time, a first image from light from a stereoscopic optical path in an endoscope held and positioned by a robotic surgical system at a first time wherein the light is from tissue. This method also includes capturing at a second time different from the first time, a second image from the light wherein only one of the first image and the second image includes a combination of a fluorescence image and a visible image; and an other of the first image and the second image is a visible image. An artificial fluorescence image is generated using the captured fluorescence image. An augmented stereoscopic image of at least a portion of the tissue including the artificial fluorescence image is also generated.

Figure 1:
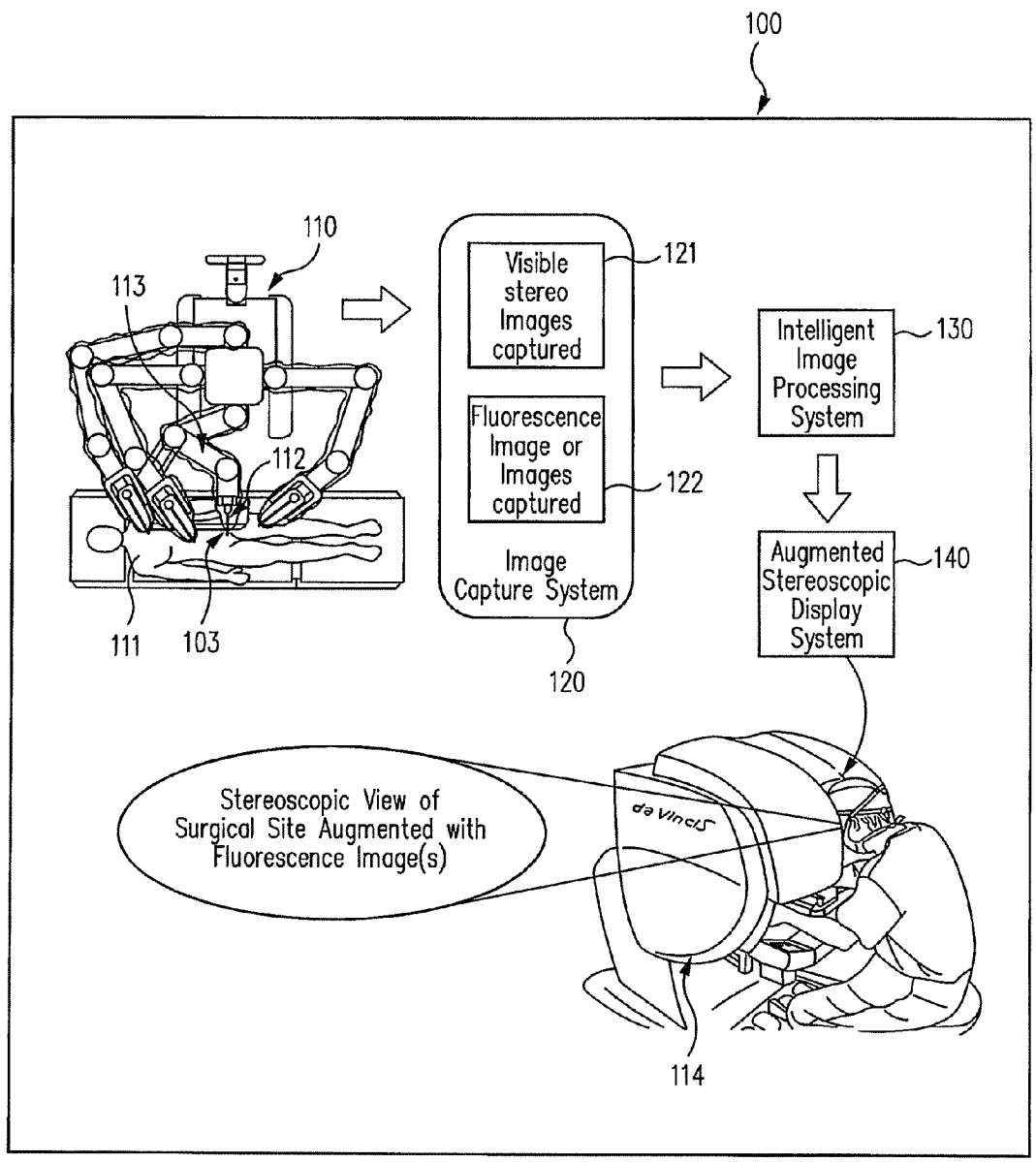
FIG. 1 is a diagrammatic view of an augmented stereoscopic visualization system for a minimally invasive surgical robot.

In the drawings, the first digit of a figure number for single digit figure numbers and the first two digits of a figure number for double digit figure numbers indicates the figure in which the element with that figure number first appeared.

As used herein, "robot" should be broadly construed, and includes telerobotic systems.

As used herein, electronic stereoscopic imaging includes the use of two imaging channels (i.e., channels for left and right images).

As used herein, a stereoscopic optical path includes two channels in an endoscope for transporting light from tissue (e.g., channels for left and right images). The light transported in each channel represents a different view of the tissue and so is sometimes referred to as first light and second light to distinguish the light in the two channels. The light can include one or more images.

As used herein, an illumination path includes a path in an endoscope providing illumination to tissue.

As used herein, images captured in the visible spectrum are referred to as visible images.

As used herein, images, not including visible images, captured in an alternate imaging modality are referred to as alternate images. An example of an alternate imaging modality is an image that captures tissue fluorescence.

As used herein, images captured as the result of fluorescence are referred to herein as fluorescence images. There are various fluorescence imaging modalities. Fluorescence may result from the use of, e.g., injectable dyes, fluorescent proteins, or fluorescent tagged antibodies. Fluorescence may result from, e.g., excitation by laser or other energy source. Fluorescence images can provide vital in vivo patient information that is critical for surgery, such as pathology information (e.g., fluorescing tumors) or anatomic information (e.g., fluorescing tagged nerves).

As used herein, a long pass filter lets all the wavelengths longer than a wavelength number through. For instance, a 510 nm long pass filter lets all the wavelengths greater than 510 nm through the filter. Typically, long pass filters are used as barrier filters in fluorescence. A long pass filter is sometimes used to pass the fluorescence light through the filter and not the excitation light.

As used herein, a short pass filter lets light through the filter that is lower in wavelength than a wavelength of the filter. For instance, a 480 nm short pass filter lets light that is shorter in wavelength than 480 nm (less than 480 nm) through the filter. Short pass filters are sometimes used as excitation filters for fluorescence.

As used herein, a band pass filter allows only a set of wavelengths through. The wavelength number is referred to as the center wavelength of a band pass filter. The center wavelength is the wavelength that allows the most light through within the range of wavelengths that will be passed through the filter. Frequently this is the center wavelength of the filter. A band pass filter is rated by center wavelength and the pass band or width.

DETAILED DESCRIPTION

Aspects of this invention augment the stereoscopic video capturing and viewing capability of surgical robots, e.g., the da Vinci® Surgical Robot System manufactured by Intuitive Surgical, Inc. of Sunnyvale, Calif. by incorporating both stereoscopic visible images and stereoscopic alternate imaging modality images to identify, in real-time during surgery, tissue of clinical interest. (da Vinci® is a registered trademark of Intuitive Surgical, Inc. of Sunnyvale, Calif.)

Aspects of the invention simultaneously provide stereoscopic alternate modality images that identify tissue of clinical interest in addition to stereoscopic visible images that a surgeon normally uses when performing a surgical operation using a teleoperated surgical system. This combination of stereoscopic visible and alternate images provides benefits including, but not limited to, allowing a surgeon in real-time to identify positive tumor margins for diseased tissue excision and to identify nerves so as to avoid cutting those nerves.

This imaging combination may be a continuous overlay of the stereoscopic visible and alternate images, or the overlay of stereoscopic alternate images may be toggled on and off (e.g., by using a foot pedal or by double-clicking master finger grips on the da Vinci® Surgical System surgeons console).

FIG. 1 is a high level diagrammatic view of one robotic surgical system, for example, the da Vinci® Surgical System, including an augmented stereoscopic visualization system 100. In this example, a surgeon, using a surgeon's console 114, remotely manipulates an endoscope 112 using a robotic manipulator arm 113. There are other parts, cables etc. associated with the da Vinci® Surgical System, but these are not illustrated in FIG. 1 to avoid detracting from the disclosure.

As explained more completely below, an illumination system (not shown) is coupled to endoscope 112. Typically, the illumination system provides white light and at least one fluorescence excitation light. All or part of this light is coupled to at least one illumination path in endoscope 112 by a fiber optic bundle. The light passes through at least one illumination path in endoscope 112 and illuminates tissue 103 of a patient 111. Endoscope 112 also includes, in one aspect, two optical channels for passing light from the tissue, e.g., reflected white light and fluorescence. The reflected white light is a visible image, while the fluorescence is a fluorescence image.

The white light reflected from tissue 103 is captured as visible stereoscopic images 121 in image capture system 120. Similarly, a fluorescence image or fluorescence images 122 are also captured in image capture hardware 120. As explained more completely below, there are a variety of ways that the various images needed for the stereoscopic display can be captured. Typically, image capture hardware 120 includes at least one camera including a charge-coupled device (CCD) sensor. The capture of the images occurs simultaneously or nearly simultaneously in image capture system 120.

In one aspect, intelligent image processing system 130 functions in cooperation with image capture system 120 to extract the fluorescence image from the information provided from the optical channel. For example, filter processing is working with a spectrum balancer to compensate for any degradation to the visible image in the process of removing the fluorescence image given the frequency of the laser light used to excite the fluorescence.

Also, the captured images are processed for subsequent display stereoscopically in intelligent imaging processing system 130. For example, when separate optical channels having a fixed relationship are used for transporting the fluorescence image and the reflected white light image to intelligent image processing system 130, a one step calibration is used based upon the fixed relative positions of the separate optical channels.

Intelligent image processing system 130, also when appropriate, performs spatial image registration of the fluorescence image(s) and the visible images. The spatial image registration permits proper overlay of the fluorescence image in augmented stereoscopic display system 140.

In another aspect, intelligent image processing system 130 does stereo matching of left-channel and right-channel visible images. In still other aspects, intelligent image processing generates artificial visible and/or fluorescence images so that an augmented stereoscopic display can be presented to the surgeon.

Thus, for a surgeon to perform minimally invasive surgery using surgical robotic system with augmented stereoscopic visualization 100, tissue 103 is illuminated in an illuminate tissue process 201 (FIG. 2) to allow capture of both visible images and alternate images, such as fluorescence images.

Knowledgeable individuals understand that fluorescence can occur naturally when tissue itself is excited by a particular wavelength light, or alternatively, when tissue-specific fluorophores attached to tissue 103 are excited by a particular wavelength of light. Thus, the fluorescence images described herein can be obtained by either technique. Knowledgeable persons also know that some fluorophores emit energy within the visible spectrum, and others emit energy outside the visible spectrum (e.g., at approximately 830 nm).

Aspects of the invention include illumination of tissue using both a broad spectrum white light source for visible images and another light source for the alternate images in illuminate tissue process 201. For example, narrow band light to excite tissue-specific fluorophores may be used as the light source for the alternate images.

For fluorescence alternate images, if the excitation wavelength occurs in the visible spectrum, the white light may function to excite the fluorophores. If the excitation wavelength occurs outside the visible spectrum (e.g., in the near infrared (IR)) or if additional excitation energy is required at a wavelength in the visible spectrum, a laser module (or other energy source, such as a light-emitting diode or filtered white light) is used to simultaneously illuminate the tissue in illuminate tissue process 201. This simultaneous illumination can be accomplished in various ways as discussed more completely below.

The light from tissue 103, reflected and emitted, is conditioned in pre-process light from tissue process 202. For example, the light is filtered to enhance the contrast in the images in the stereoscopic video display. If the reflected and emitted light are included in a single light channel, pre-process light from tissue process 202 separates the light into reflected light and emitted light.

Pre-process light from tissue process 202 is optional and may not be used in some aspects. Thus, either the preprocessed light from tissue 103 or the original light from tissue 103 is passed to capture images process 203.

The output from pre-process light from tissue process 202 is captured in capture images process 203 as visible images and alternate image(s). See for example, image capture system 120 described above.

Intelligent processing 204 performs the necessary processes on the captured image to provide a complete set of visible and fluorescent images for stereoscopic display.

In generate stereoscopic video display of tissue process 205, the set of visible and fluorescent images are blended as needed to generate a three dimensional presentation of the tissue. The three-dimensional presentation eliminates problems in the prior art associated with varying distances and geometries of the tissue with respect to the endoscope. In particular, the real-time stereoscopic display of the tissue with the alternate image and/or visible images provides an accurate three-dimensional view of the tissue that the surgeon can use in determining the scope of the surgery, e.g., location of diseased tissue, location of nerves or other organs etc.

Two Separate Optical Paths from Tissue

Figure 3A:
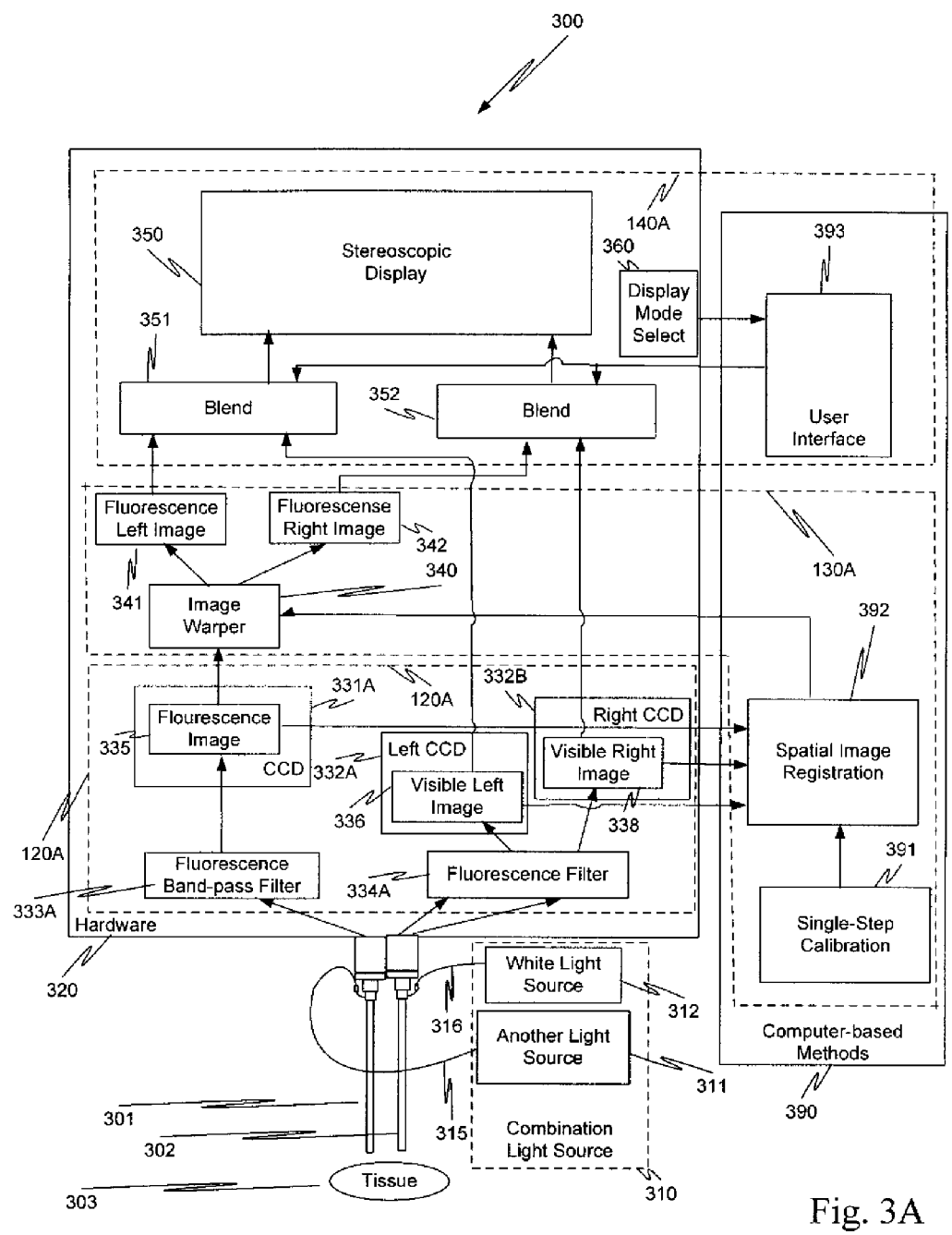
FIG. 3A is a schematic view that illustrates hardware and software (image processing and user interface) aspects of the use of two separate optical paths (but one camera unit for fluorescence imaging) for capturing, processing, and outputting blended real-time stereoscopic visible and fluorescence images in a minimally invasive surgical robotic system.

In the embodiment of FIG. 3A, a robotic surgical system (not shown) includes two separate and distinct optical paths for transporting light from tissue 303 to augmented stereoscopic vision system 300. Light from the two optical paths is used to generate a real-time stereoscopic video display of tissue 303 for the surgeon operating the robotic surgical system.

In one aspect, the stereoscopic video display includes a normal three-dimensional view of tissue 303 augmented with one or more alternate images to highlight regions of interest in the tissue such as diseased portions of tissue 303 and/or a specific tissue, such as a nerve or organ different from that being operated on. Typically, the alternate image is presented in a specific color, e.g., blue.

In this example, two separate endoscopes 301, 302 are shown as providing a stereoscopic optical path and at least one other optical path from tissue 303 to hardware 320. Endoscope 302 includes two light channels that make up the stereoscopic optical path, while endoscope 301 includes at least one light channel. Alternatively, all of the light channels can be in a single endoscope. Accordingly, the aspects of FIG. 3A are illustrative only and are not intended to limit this embodiment to the specific aspects shown.

In this example, endoscopes 301 and 302 each include an illumination path for providing light from combination light source 310 to tissue 303. Alternatively, a single illumination path could be used to provide the light to tissue 303. While it is not shown, in one aspect, endoscopes 301 and 302 are each held and moved by the robotic surgical system in a fixed relationship. See FIG. 1 for example. Alternatively, different robotic arms could be used to hold and move the two endoscopes separately. In such an aspect, the real time kinematic information from the robotic arms is used in aligning the two endoscopes.

In this example, augmented stereoscopic vision system 300 includes a combination light source 310, hardware 320, and a plurality of computer-based methods 390. As shown in FIG. 3A, a portion of hardware 320 makes up image capture system 120A. Another portion of hardware 320 and a portion of plurality of computer-based methods 390 make up intelligent image processing system 130A. Yet another portion of hardware 320 and another portion of plurality of computer-based methods 390 make up augmented stereoscopic display system 140A. Within image capture system 120A and intelligent image processing system 130A, the portions that process visible images make up a visible imaging system while the portions that process fluorescence images make up an alternate imaging system.

Figure 2:
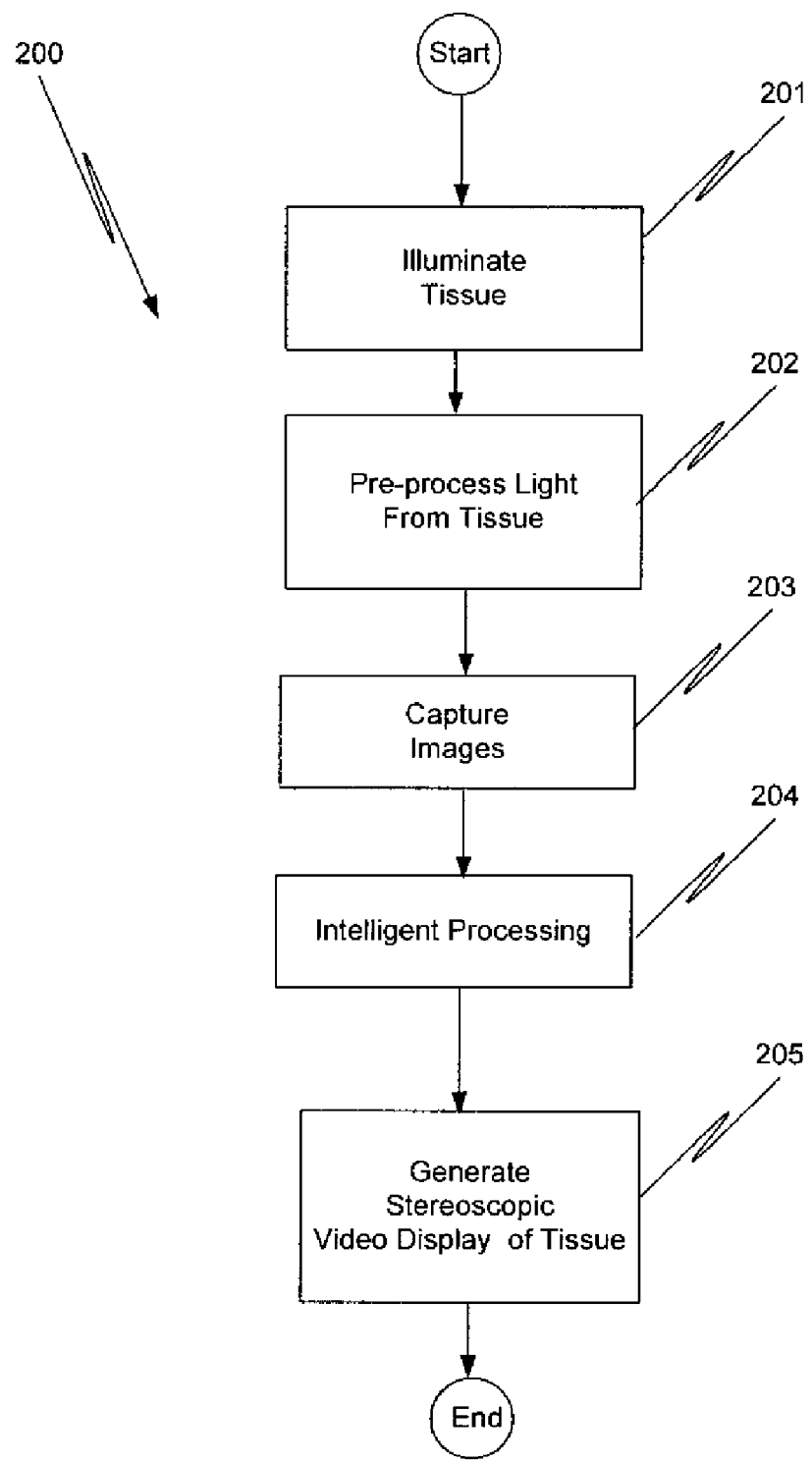
FIG. 2 is process flow diagram of a process performed using, for example, the augmented stereoscopic visualization system for a minimally invasive surgical robot of FIG. 1.
Figure 4:
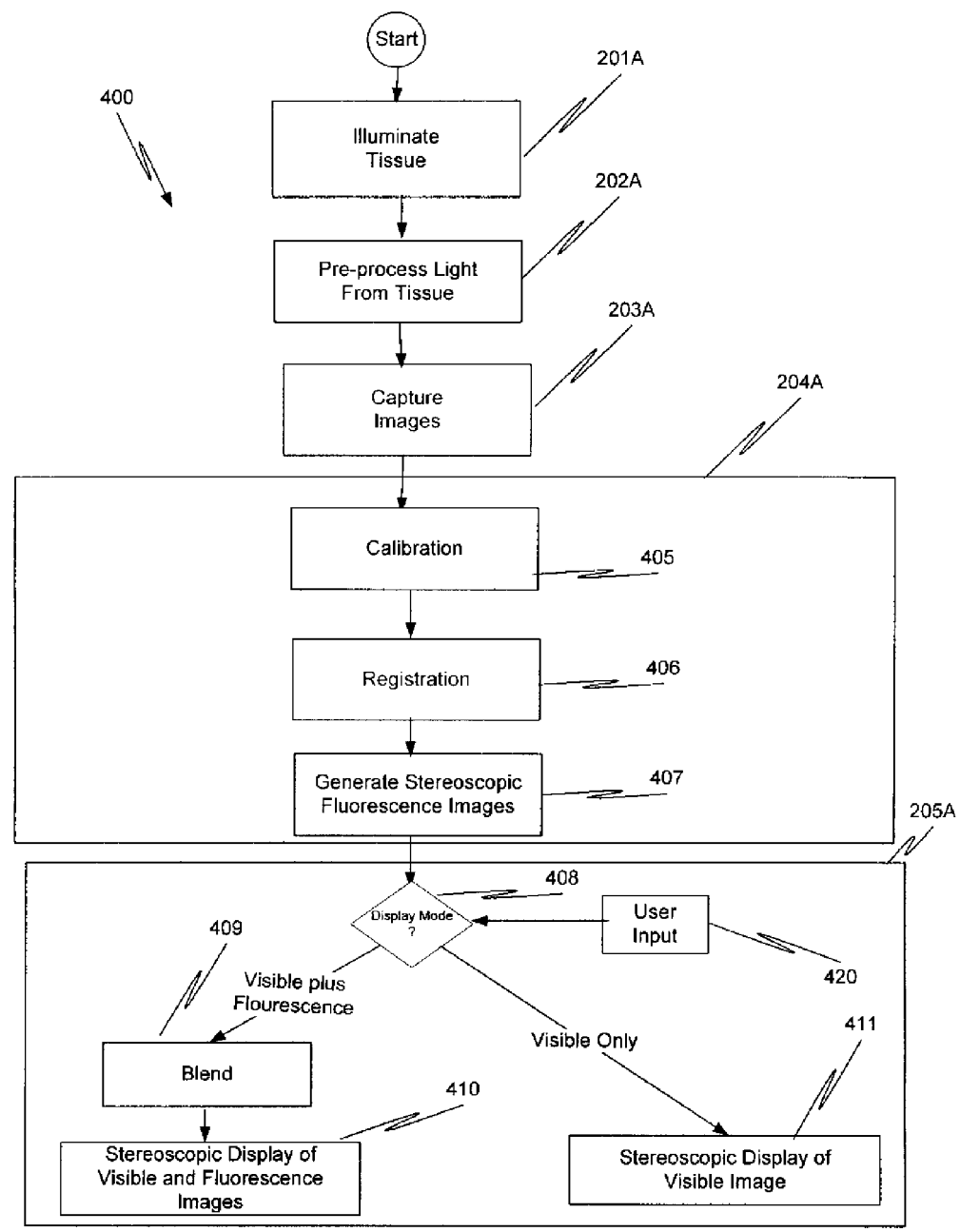
FIG. 4 is process flow diagram of a process performed using, for example, the augmented stereoscopic visualization system for a minimally invasive surgical robot of FIG. 3A.

Also, method 400 of FIG. 4 is implemented, in one aspect, using augmented stereoscopic vision system 300. As shown in FIG. 4, method 400 includes a plurality of separate processes. Method 400 is one implementation of method 200 (FIG. 2).

Figure 3B:
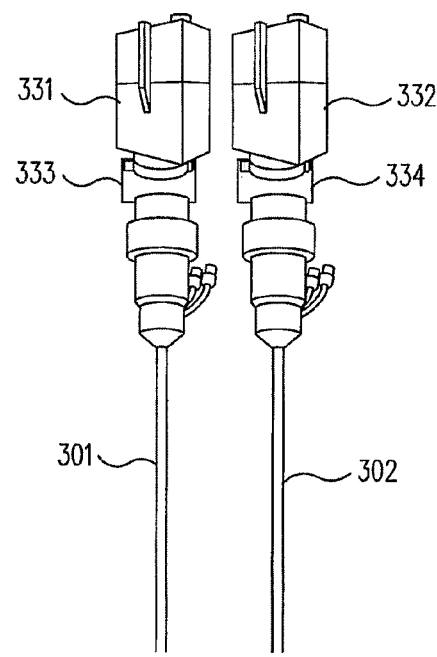
FIG. 3B is a more detailed view showing endoscopes with two separate optical paths, and separate camera units coupled to each optical path.

In one aspect, hardware 320 includes at least two camera units 331, 332 (FIG. 3B). One camera unit 332 includes two 3-chip charge-coupled device (CCD) high definition cameras and another camera 331 unit includes a one-chip CCD camera.

In this aspect, camera unit 331 is coupled to endoscope 301 by a filter block 333 that includes a filter, as described more completely below for preprocessing the light from endoscope 301. Similarly, camera unit 332 is coupled to endoscope 302 by a filter block 334 that includes a filter, as described more completely below for preprocessing the light from endoscope 302. In another aspect, the filters can be incorporated in the camera units or alternatively cannot be used. Hardware 320 also includes hardware circuits for performing the functions described more completely below. Plurality of computer-based methods 390 are, for example, software executing on a computer processor.

Those of knowledge appreciate that computer-based methods can also be implemented using hardware only, implemented partially in hardware and partially in executable computer code, or implemented entirely in executable computer code. Similarly, the hardware described herein could also be implemented as computer-based methods or a combination of hardware and computer-based methods. Accordingly, the characterization used herein with respect to hardware and computer-based methods are illustrative only and are not intended to be limiting to the specific aspect described.

Two Separate Optical Paths—Illumination

Combination light source 310, 310A (FIGS. 3A and 3C) includes a white light source 312A and another light source 311A. Combination light source 310 is used in conjunction with an illumination path in an endoscope to perform illuminate tissue process 201A (FIG. 4). White light source 312A provides white light, e.g., a first light, which illuminates tissue 303. Other light source 311 provides light, e.g., a second light, for exciting alternate images of tissue 303. For example, narrow band light from light source 311A is used to excite tissue-specific fluorophores so that the alternate images are fluorescence images of specific tissue within tissue 303.

For alternate images that are fluorescence images, if the fluorescence excitation wavelength occurs in the visible spectrum, white light source 312A (FIG. 3B) may be used as both the white light source and as a source to excite the fluorophores. If the fluorescence excitation wavelength occurs outside the visible spectrum (e.g., in the near infrared (IR)) or if additional excitation energy is required at a wavelength in the visible spectrum, a laser module 317 (or other energy source, such as a light-emitting diode or filtered white light) is used to simultaneously illuminate tissue 303.

Thus, in one aspect, fluorescence is triggered by light from laser module 317. As an example, antibody agents, which were obtained from Medarex, Inc., were excited using a 525 nm laser.

The particular alternate light source selected for combination light source 310A depends on the fluorophore or fluorophores used. Excitation and emission maxima of various FDA approved fluorescent dyes used in vivo are presented in Table 1.

TABLE 1

| Fluorescent Dye | Excitation maxima (nm) | Emission maxima (nm) |
| --- | --- | --- |
| Fluorscein | 494 | 521 |
| Indocyanine Green | 810 | 830 |
| Indigo Carmine | 436 in alkaline solution | 528 in alkaline solution |
| Methylene Blue | 664 | 682 |

Table 2 presents examples of common protein fluorophores used in biological systems.

TABLE 2

| Fluorescent proteins/ Fluorophore | Excitation maxima (nm) | Emission maxima (nm) |
| --- | --- | --- |
| GFP | 489 | 508 |
| YFP | 514 | 527 |
| DsRed (RFP) | 558 | 583 |
| FITC | 494** | 518** |
| Texas red | 595** | 615** |
| Cy5 | 650** | 670** |
| Alexa Fluor 568 | 578** | 603** |
| Alexa Fluor 647 | 650** | 668** |
| Hoechst 33258 | 346 | 460 |
| TOPRO-3 | 642 | 661 |

**Approximate excitation and fluorescence emission maxima for conjugates.

Those knowledgeable in the field understand that a fluorophore can be bound to an agent that in turn binds to a particular tissue of the patient. Accordingly, when a particular fluorophore is selected, combination light source 310A includes a light source that provides light with the excitation maxima wavelength for that fluorophore. Thus, given the fluorophore or fluorophores of interest, appropriate light sources can be included in combination light source 310, 310A.

The above examples in Tables 1 and 2 are illustrative only and are not intended to limit this aspect to the particular examples presented. In view of this disclosure, an alternate imaging characteristic of the tissue can be selected and then an appropriate light source can be selected based upon the fluorescence or other alternate imaging characteristics being utilized.

In one aspect, white light source 312A of combination light source 310A (FIG. 3C) uses a Xenon lamp 314 with (1) an elliptic back reflector 314A and (2) a long pass ultraviolet (W) filter coating 314B is used to create broadband white illumination light for visible images. The use of a Xenon lamp is illustrative only and is not intended to be limiting. For example, a high pressure mercury arc lamp, other arc lamps, or other broadband light sources may be used.

Band pass filter 318 removes expected fluorescence emission wavelengths from the white illumination light. This increases the contrast of the fluorescence image. The fluorescence image capture chip(s) are prevented from being saturated with reflected light from the entire tissue at the fluorescence wavelength.

The filtered white light from filter 318 is directed into a fiber optic bundle 316. Similarly, the light from laser module 317 is directed into fiber optic bundle 315. As illustrated in FIG. 3A, fiber optic bundles 315 and 316 are two separate and distinct fiber optic bundles. However, in another aspect, bundles 315 and 316 may be different groups of fibers in a common fiber optic bundle.

Two Separate Optical Paths—Image Capture System 120A

The visible images from tissue 303 (FIG. 3A) are captured from one stereoscopic optical path in endoscope 302, and the fluorescence image is captured from a separate monoscopic or stereoscopic optical path in endoscope 301. As noted above, while the separate optical paths are illustrated in two separate endoscopes in FIG. 3A, the separate optical paths may be in a single endoscope. An advantage of using two separate optical paths is optical efficiency because there is no loss due to, e.g., aspects that use beam splitting, as described below.

The light from the stereoscopic optical path of endoscope 302, e.g., a first light, is passed through a fluorescence excitation and fluorescence filter 334A to remove the fluorescence excitation wavelengths and the fluorescence, which leaves the visible left and right images. This helps to enhance the contrast between the visible stereoscopic image and the fluorescence image and to improve the quality of the visible image.

The filtered visible images from fluorescence excitation and fluorescence filter 334A are captured as a visible left image 336 in a left CCD 332A and a visible right image 338 in a right CCD 332B. Left CCD 332A captures red, green, and blue images for visible left image 336. Similarly, right CCD 332B captures red, green, and blue images for visible right image 338. Left CCD 332A and right CCD 332B can be multiple CCDs with each CCD capturing a different color component; a single CCD with a different region of that CCD capturing a particular color component, etc.

Moreover, herein use of a monochrome charge-coupled device (CCD) is illustrative only. Instead of a monochrome CCD, an intensified charge-coupled device (ICCD), a charge injection device (CID), a charge modulation device (CMD), a complementary metal oxide semiconductor image sensor (CMOS) or an electron beam charge-coupled device (EB-CCD) type of sensor may also be used. Similarly, herein, a 3-chip CCD senor is also illustrative and a color CMOS image sensor, or a three-CMOS color image sensor assembly may also be used. These comments apply to the various 1-chip CCD sensors and 3-chip sensors described herein and so are not repeated with respect to each aspect of such sensors described herein.

The light from the optical path of endoscope 301 is passed through a fluorescence band-pass filter 333A to remove all visible wavelengths but the fluorescence image. Fluorescence image 335 from fluorescence band-pass filter 333A is captured in CCD 331A, which in one aspect is a single CCD sensor.

In this aspect, filters 333A and 334A perform pre-process light from tissue operation 202A (FIG. 4). Capture images process 203A is performed by capturing the various images in the CCDs as just described.

Two Separate Optical Paths—Intelligent Image Processing System 130A

Since captured visible and fluorescence images originate from optical paths at different locations, the captured images are aligned using image processing methods. In this example, typically prior to using the camera units in a normal setting, captured images, typically visible images, are provided to single-step calibration 391. If the physical relationship between the two optical paths is constant, image alignment is done once in single-step calibration 391 prior to normal use, and the alignment information is then applied to all captured images (a fixed relationship or "single-step" calibration). Single-step calibration 391 determines the displacement necessary to bring the images from the two optical paths into proper alignment.

In one aspect of single-step calibration 391, at least two factors are considered:
1) the intrinsic calibration of each endoscope and camera that is important for the geometric aspect of imaging, e.g., a) focal length, b) optical center, and c) lens distortion parameters; and
2) the relative position and orientation of the two optical paths.

A computer-based method for such a calibration may involve using the two endoscopes and associated camera units to capture images of a calibration pattern, for example, a checker-board pattern. So long as the relationship between the optical paths remains fixed, this calibration is valid. In this aspect, single-step calibration 391 (FIG. 3A) is calibration process 405 (FIG. 4) within intelligent imaging process 204A.

The results from single-step calibration 391 are supplied to spatial image registration 392 (FIG. 3A) of registration process 406 (FIG. 4). Spatial image registration 392 also receives as inputs, each of captured images 335, 336, and 338. Briefly, spatial image registration registers the images taken from different viewing angles so that any two corresponding pixels from both images, based on the registration results, refer to the same scene point in the world.

Figure 3C:
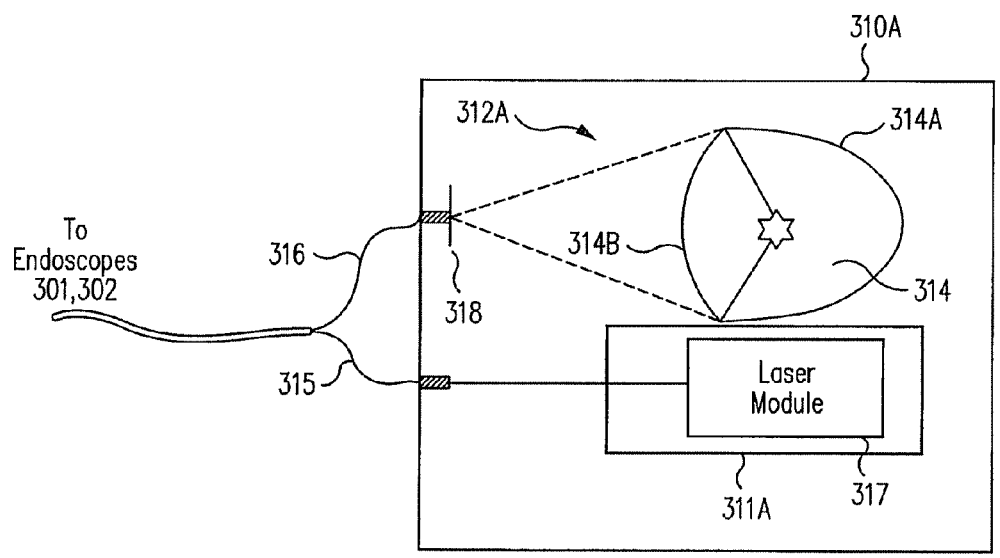
FIG. 3C illustrates one aspect of a combination illumination source connected to a fiber optic cable.
Figure 3D:
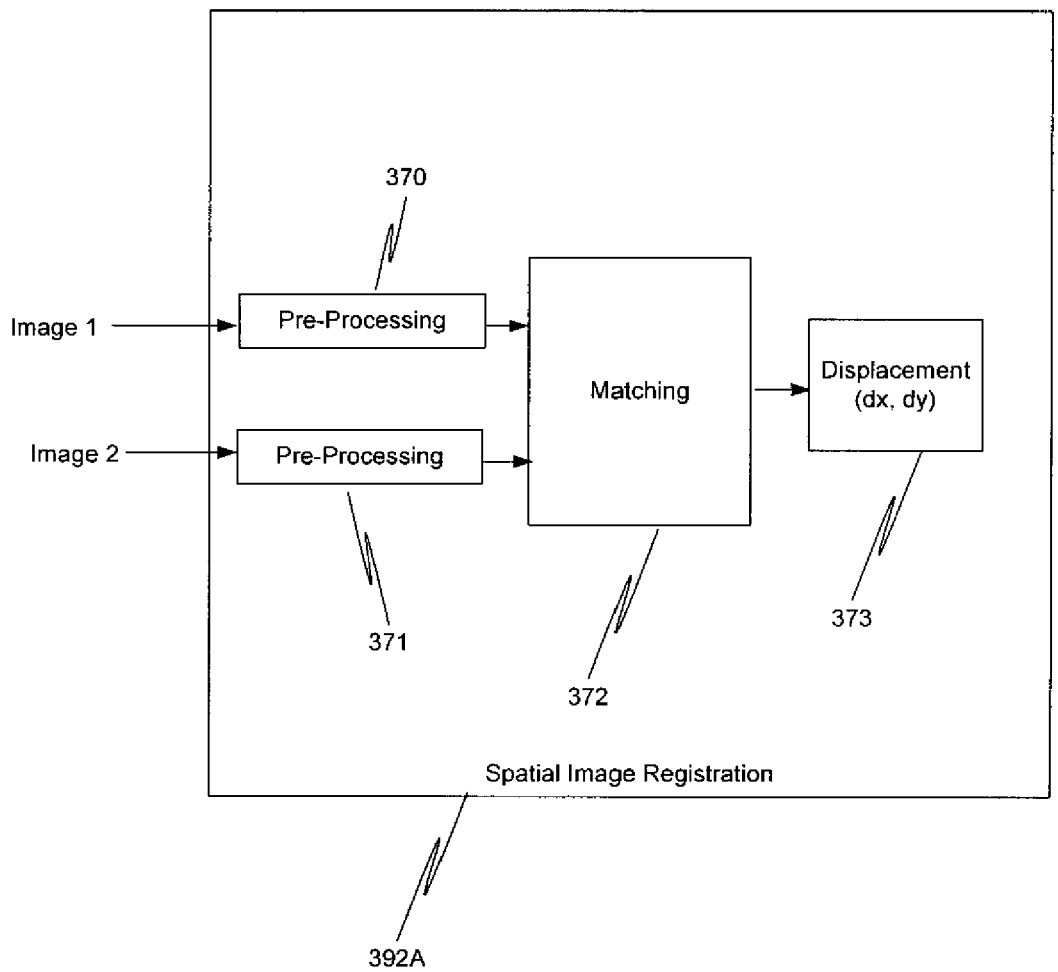
FIG. 3D illustrates one aspect of a spatial image registration system.

One aspect of spatial image registration 392 is presented in FIG. 3D. Table 3 presents image modalities that are sometimes used in spatial image registration 392.

TABLE 3

| Image Modalities | Input for matching | | |
|---|---|---|---|
| | Raw Image | Gradient Images | Image Features |
| Visible against visible | Yes | Yes | Yes |

TABLE 3-continued

| | Input for matching | | |
|---|---|---|---|
| Image Modalities | Raw Image | Gradient Images | Image Features |
| Visible against fluorescence | | Yes | Yes |

In spatial image registration 392A (FIG. 3D), two of the captured images, e.g., the fluorescence image and one of the visible images, are input as Image 1 to pre-processing 370 and Image 2 to pre-processing 371. Depending on the feature being used in matching the visible against the fluorescence, pre-processing 370, 371 generates the appropriate information. For example, for gradient images, the gradient of the raw images along the X and Y directions is generated. Similarly, image features are obtained by pre-processing raw images. Many image features are available, for example, a histogram of image intensities in a local region.

The results from pre-processing 370, 371 are supplied to matching process 372. There are many methods available for matching process 372. A first example of matching is a normalized cross-correlation of gradient images computed using all pixels in a small region surrounding the pixel at location (x, y). Another example is mutual information based matching with the inputs being intensity histograms.

The output of matching process 372 is a displacement (dx, dy) that gives the best matching score after moving the pixel at (x, y) from one input image to the other input image. If the displacement (dx, dy) is generated for all the pixels in the inputs, the result is called a disparity map consisting of two images of dx (x, y) and dy (x, y).

In this aspect, fluorescence image 335, sometimes referred to as captured fluorescence image 335 or stored fluorescence image 335, is registered to visible left image 336, sometimes referred to as captured visible left image 336 or stored visible left image 336, in spatial registration 392. Alternatively, two visible images 336 and 338 can be registered first and then registered against fluorescence image 335. Similarly, fluorescence image 335 is registered to visible right image 338, sometimes referred to as captured visible right image 338 or stored visible right image 338, in spatial registration 392. In general, herein, an image that is shown in a CCD is sometimes referred to as a captured image or a stored image.

The results from spatial image registration 392 are available to image warper 340. Image warper 340 also receives as input captured fluorescence image 335. Using the spatial image registration information, image warper 340 converts captured fluorescence image 335 into a stereoscopic fluorescence pair, e.g., an artificial fluorescence left image 341 and an artificial fluorescence right image 342 for use in generating the stereoscopic display of the fluorescence image. Herein, artificial is used to refer that an image that is generated by hardware, software, or a combination of the two, and is in contrast to a captured image.

Specifically, image warper 340 uses the registration of fluorescence image 335 to visible left image 336 to warp fluorescence image 335 into fluorescence left image 341. Similarly, image warper 340 uses the registration of fluorescence image 335 to visible right image 338 to warp fluorescence image 335 into fluorescence right image 342. Thus, image warper 340 performs generate stereoscopic fluorescence images process 407 (FIG. 4). Note that while this description is necessarily linear and describes a single pass through the processing, the processes are occurring in real-time and the various images are being continuously updated to reflect the current state of tissue 303 as observed via endoscopes 301, 302.

Two Separate Optical Paths—Augmented Stereoscopic Display System 140A

In one aspect, the augmented stereoscopic video output display may be operated in various modes. For example, in a first mode, only stereoscopic visible images are output to the surgeon, as in the da Vinci® Surgical System. In a second mode, the fluorescence images are superimposed on the visible images to create augmented images, and the stereoscopic augmented images are output to the surgeon.

The video output may be toggled between these two modes by using, e.g., a foot switch, a double click of the master grips that control the surgical instruments, voice control, and other like switching methods. The toggle for switching between the two modes is represented in FIG. 3A as display mode select 360.

In response to a user input 420 (FIG. 4), the signal from display mode select 360 (FIG. 3A) is provided to a display mode check operation 408 in a user interface 393 that in turn provides a control signal to blend circuit 351 and blend circuit 352. If the surgeon selects visible only, visible left image 336 and visible right image 338 are presented in stereoscopic display 350 via stereoscopic display of visible image process 411 (FIG. 4) in generate stereoscopic video display of tissue process 205A. In one aspect, intelligent image processing system 130, can include spectrum balancers, similar to those shown in FIG. 5A, to color balance the visible left and right images provided to blend circuit 351 and blend circuit 352, respectively.

If the surgeon selects visible plus fluorescence, in blend process 409, blend circuit 351 blends fluorescence left image 341 and visible left image 336, while blend circuit 352 blends fluorescence right image 342 and visible right image 338. Different image blending options, such as alpha blending, can be implemented in blend circuits 351, 352. The outputs of blend circuits 351, 352 are presented in stereoscopic display 350 via stereoscopic display of visible and fluorescence images process 410 (FIG. 4).

Since fluorescence images 341, 342 show tissue of medical interest, fluorescence images 341, 342 can be processed to enhance the surgeon's video display presentation. This processing produces an artificial fluorescence image. For example, the fluorescing regions in the fluorescence image may be artificially colored (pseudo-colored) using known methods. When the artificial fluorescence image is blended with the visible video image, the surgeon then sees the fluorescing tissue (e.g., artificially made bright green) in a high contrast to the surrounding tissue in the visible image. Again, different image blending options, such as alpha blending, of the pseudo color fluorescence images and visible images are made available.

In another aspect of enhancing the fluorescence image, a highly visible border is placed around the fluorescence area using known methods. Frequently, the fluorescing tissue is associated with a go or no go decision, e.g., remove or do not remove, by the surgeon and so the highly visible border is of assistance.

In yet another aspect of enhancing the fluorescence images, a local histogram equalization is performed on raw fluorescence image data 335. Instead of performing a histogram equalization for the entire fluorescence image frame, one or more local areas are identified around the portion of the fluorescence image that shows the fluorescing tissue. The histogram equalization is performed on the one or more local areas to balance the light dark fluorescence appearance in the enhanced fluorescence image. Such image enhancement also helps spatial image registration.

Further, the fluorescence image may be artificially sustained in the video output to the surgeon. As an example, the fluorescence image may be sustained after an injected agent no longer fluoresces so that the fluorescing region is still visible to the surgeon.

The stable platform provided by robotic surgical system, which holds the endoscope or endoscopes, facilitates the processing of the captured fluorescence image in real-time because, unlike hand-held endoscopes, it is unnecessary to compensate for instability of the endoscope or endoscopes which typically results in blurred fluorescence images for hand guided endoscopes. In addition, the sharper fluorescence image relative to hand held endoscopes facilitates the enhanced processing of the captured fluorescence image.

Two Separate Optical Paths—Multiple Fluorescence Images

Figure 3E:
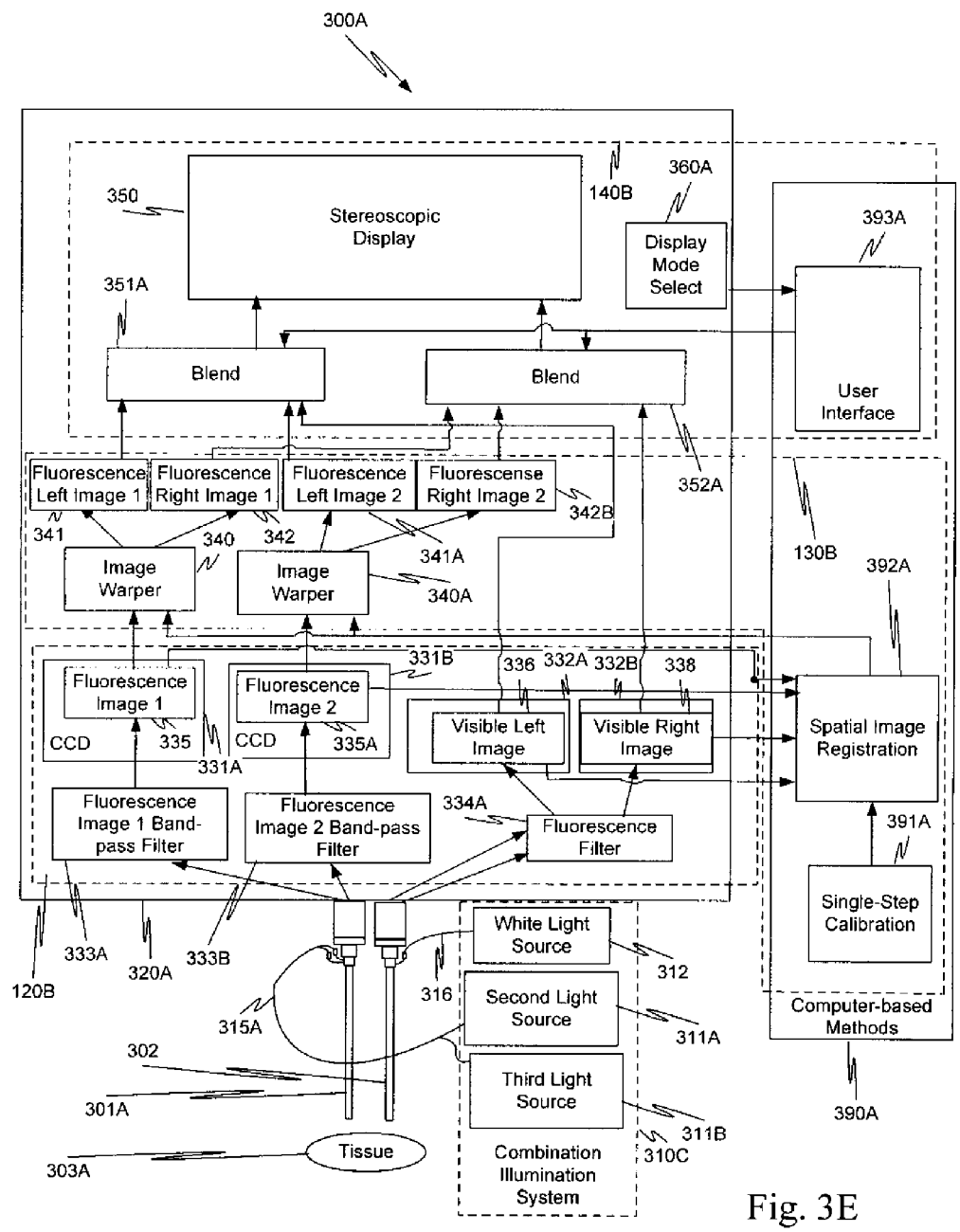
FIG. 3E is an alternate schematic view that illustrates hardware and software (image processing and user interface) aspects of the use of two separate optical paths and stereo cameras for capturing, processing, and outputting blended real-time stereoscopic visible and fluorescence images in a minimally invasive surgical robotic system.

In another aspect of using two separate optical paths, multiple fluorescence images can be captured using augmented stereoscopic vision system 300A (FIG. 3E). System 300A is similar to system 300 and so only the differences are described. Elements with the same reference numeral are the same or equivalent elements.

In the embodiment of FIG. 3E, a robotic surgical system (not shown) includes two separate and distinct stereoscopic optical paths for transporting light from tissue 303A to augmented stereoscopic vision system 300A. Light from the two light paths is used to generate a real-time stereoscopic video display of tissue 303 for the surgeon operating the robotic surgical system. The stereoscopic video display includes a normal three-dimensional view of tissue 303 augmented with two alternate images to highlight regions of interest in tissue 303A such as diseased portions of tissue 303A and other tissue in tissue 303A, such as a nerve or organ. Typically, the alternate images are each presented in a different specific color that typically contrasts with the colors normally seen in the stereoscopic video display.

Again in this example, two separate endoscopes 301A, 302 are shown as providing the two distinct stereoscopic optical paths from tissues 303A to hardware 320A. Endoscope 302 has two light channels, and endoscope 301A has two light channels. The two light channels in endoscope 301A are used for capturing two different fluorescence images, fluorescence image 1 and fluorescence image 2. For convenience, fluorescence image 1 is taken to be the same as the fluorescence image in FIG. 3A, and the visible images are taken as the same visible images as in FIG. 3A. In this aspect, camera unit 331 includes at least a two-chip CCD camera.

Thus, the description of elements 333A, 331A, 335, 340, 341 and 342 above are incorporated herein by reference. Similarly, the description of elements 334A, 332A, 336, 332B, and 338 above are incorporated herein by reference.

In this example, augmented stereoscopic vision system 300A includes a combination source illumination system 310C, hardware 320A, and a plurality of computer-based methods 390A. As shown in FIG. 3E, a portion of hardware 320A makes up image capture system 120B. Another portion of hardware 320A and a portion of plurality of computer-based methods 390A make up intelligent image processing system 130B. Yet another portion of hardware 320A and another portion of plurality of computer-based methods 390A make up augmented stereoscopic display system 140B Combination light source 310C includes a white light source 312 and two other light sources 311A and 311B. White light source 312 is similar to source 312A (FIG. 3C) except in addition to filter 318 another filter removes expected fluorescence emission wavelengths for fluorescence image 2 from the white illumination light.

Second light source 311A provides light to excite fluorescence image 1, while third light source 311B provides light to excite fluorescence image 2. In view of this disclosure, an appropriate light source can be selected based upon the fluorescence characteristics being utilized for the two different fluorescence images.

In the aspect illustrated in FIG. 3E, one fiber optic bundle 316 couples light from white light source 312 to the illumination path in endoscope 302. Fiber optic bundle 315A couples light from second light source 311A and light from third light source 311B to the illumination paths in endoscope 315A. Specifically, a first set of fibers within fiber optic bundle 315A couples light from second light source 311A to a first illumination path in endoscope 301A and a second set of fibers within fiber optic bundle 315A couples light from third light source 311B to a second illumination path in endoscope 301A.

This aspect is illustrative only and is not intended to be limiting. For example, if two illumination paths were in a single endoscope, a combination light source such as combination light source 510D with fiber optic bundle 514A (FIG. 5G) could be used instead of combination light source 310C.

Since the captured visible images and the two fluorescence images originated from optical paths at different locations, the captured images are aligned using image processing methods. In this example, the captured images are provided to single-step calibration 391A. Again, if the physical relationship between the two stereoscopic optical paths is constant, image alignment is done once in single-step calibration 391A, and the alignment information is then applied to all captured images (a fixed relationship or "single-step" calibration). The process in single-step calibration 391A is equivalent to that described above for each of the fluorescence images.

The results from single-step calibration 391A are supplied to spatial image registration 392A (FIG. 3A) of registration process 406 (FIG. 4). Spatial image registration 392A also receives as inputs, each of captured images 335, 335A, 336, and 338. The preprocessing and matching described above with respect to FIG. 3D is done for each of the fluorescence images. The results from spatial image registration 392 are available to image warpers 340, 340A.

Again, in one aspect, the augmented stereoscopic video output display may be operated in various modes. For example, in a first mode, only stereoscopic visible images are output to the surgeon, as in the da Vinci® Surgical System. In a second mode, the fluorescence images for fluorescence image 1 are superimposed on the visible images to create augmented images, and the stereoscopic augmented images are output to the surgeon. In a third mode, the fluorescence images for fluorescence image 2 are superimposed on the visible images to create augmented images, and the stereoscopic augmented images are output to the surgeon. In a fourth mode, the fluorescence images for fluorescence image 1 and the fluorescence images for fluorescence image 2 are both superimposed on the visible images to create augmented images, and the stereoscopic augmented images are output to the surgeon.

The video output may be toggled between these four modes by using, e.g., a foot switch, clicks of the master grips that control the surgical instruments, voice control, and other like switching methods. The toggle for switching between the four modes is represented in FIG. 3E as display mode select 360A.

In response to a user input 420 (FIG. 4) the signal from display mode select 360A (FIG. 3A) is provided to user interface 393A that in turn provides a control signal to blend circuit 351A and blend circuit 352A. If the surgeon selects visible only, visible left image 336 and visible right image 338 are presented in stereoscopic display 350.

If the surgeon selects visible plus fluorescence image 1, blend circuit 351A blends fluorescence left image 341 and visible left image 336, while blend circuit 352A blends fluorescence right image 342 and visible right image 352. If the surgeon selects visible plus fluorescence image 2, blend circuit 351A blends fluorescence left image 341A and visible left image 336, while blend circuit 352A blends fluorescence right image 342A and visible right image 338. If the surgeon selects visible plus fluorescence image 1 plus fluorescence image 2, blend circuit 351A blends fluorescence left image 341, fluorescence left image 341A and visible left image 336, while blend circuit 352A blends fluorescence right image 342, fluorescence right image 342A and visible right image 338.

Again, the fluorescing regions in the fluorescence images may be artificially colored (pseudo-colored) using known methods. When the artificial fluorescence image is blended with the visible video image, the surgeon then sees the fluorescing tissue (e.g., artificially made bright green) in a high contrast to the surrounding tissue in the visible image. Again, different image blending options, such as alpha blending, of the pseudo color fluorescence images and visible images are made available.

Single Stereoscopic Optical Path with Plurality of Cameras

Figure 5A:
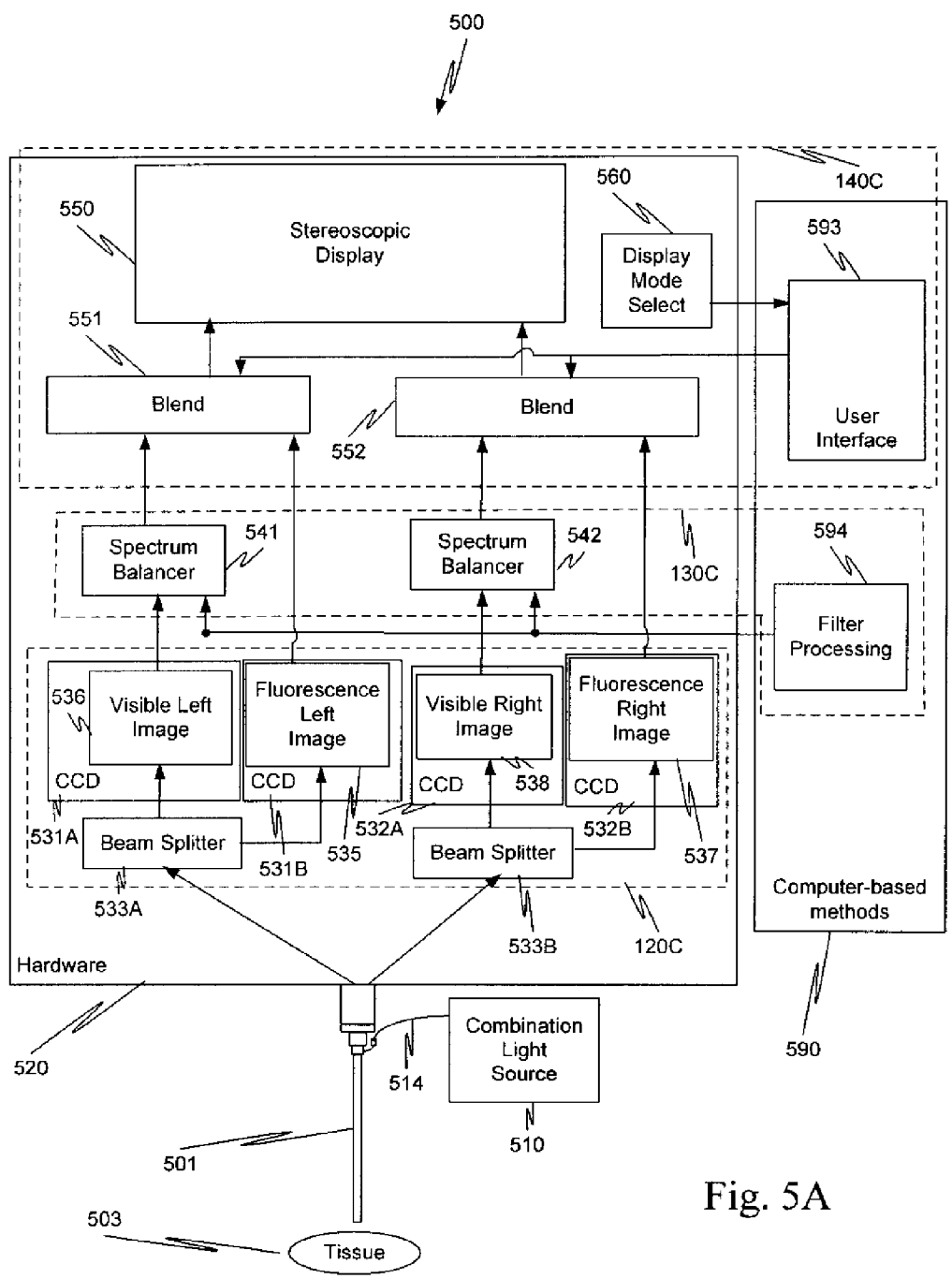
FIG. 5A is a schematic view that illustrates hardware and software (image processing and user interface) aspects of the use of a single stereoscopic optical path with separate cameras for capturing, processing, and outputting blended stereoscopic real-time visible and fluorescence images in a minimally invasive surgical robotic system.

In the embodiment of FIG. 5A, a robotic surgical system (not shown) includes a single stereoscopic optical path for transporting light from tissue 503 to augmented stereoscopic vision system 500. Light from the single stereoscopic optical path is used to generate a real-time stereoscopic video display of tissue 503 for the surgeon operating the robotic surgical system. The stereoscopic video display includes a three-dimensional view of tissue 503 augmented with an alternate image to highlight regions of interest in tissue 503 such as diseased portions of tissue 503 and/or other tissue of interest, such as a nerve or organ. In one aspect, the alternate image is presented in a specific color, e.g., blue.

In this example, a single endoscope 501 provides the stereoscopic optical path from tissue 503 to hardware 520. Endoscope 501 includes two light channels that make up the stereoscopic optical path. Endoscope 501 also includes an illumination path for providing light to tissue 503. While it is not shown, endoscope 501 is held and moved by the robotic surgical system. See FIG. 1 for example.

In this example, augmented stereoscopic vision system 500 includes a combination light source 510, hardware 520, and a plurality of computer-based methods 590. As shown in FIG. 5A, a portion of hardware 520 makes up image capture system 120C. Another portion of hardware 520 and a portion of plurality of computer-based methods 590 make up intelligent image processing system 130C. Yet another portion of hardware 520 and another portion of plurality of computer-based methods 590 make up augmented stereoscopic display system 140C. Within image capture system 120C and intelligent image processing system 130C, the portions that process visible images make up a visible imaging system while the portions that process fluorescence images make up an alternate imaging system.

Figure 6:
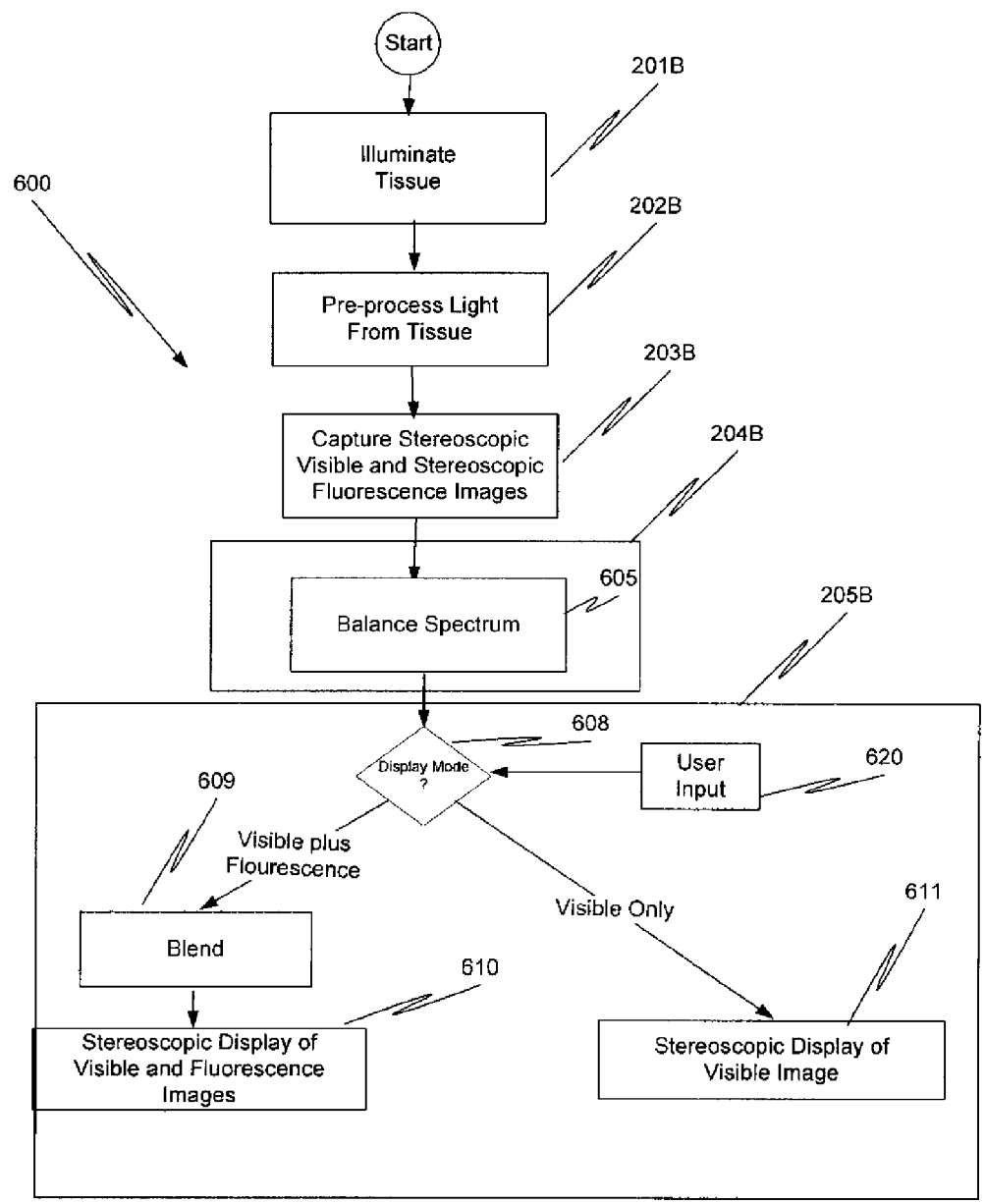
FIG. 6 is process flow diagram of a process performed using, for example, the augmented stereoscopic visualization system for a minimally invasive surgical robot of FIG. 5A.

Also, method 600 of FIG. 6 is implemented using augmented stereoscopic vision system 500. As shown in FIG. 6, method 600 includes a plurality of separate processes. Method 600 is one implementation of method 200 (FIG. 2).

Figure 5B:
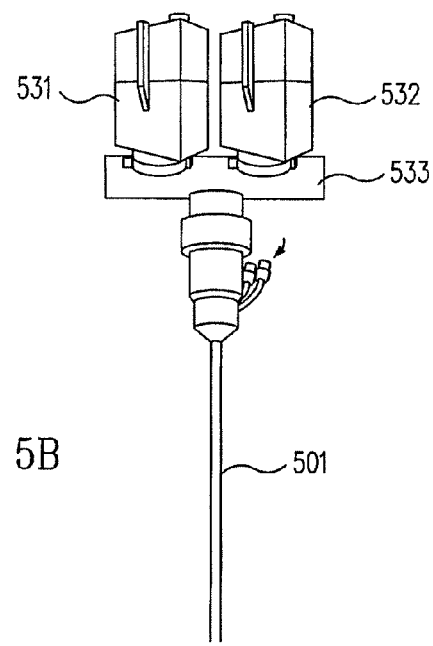
FIG. 5B is a more detailed view showing an endoscope two separate camera units coupled to the endoscope.
Figure 5C:
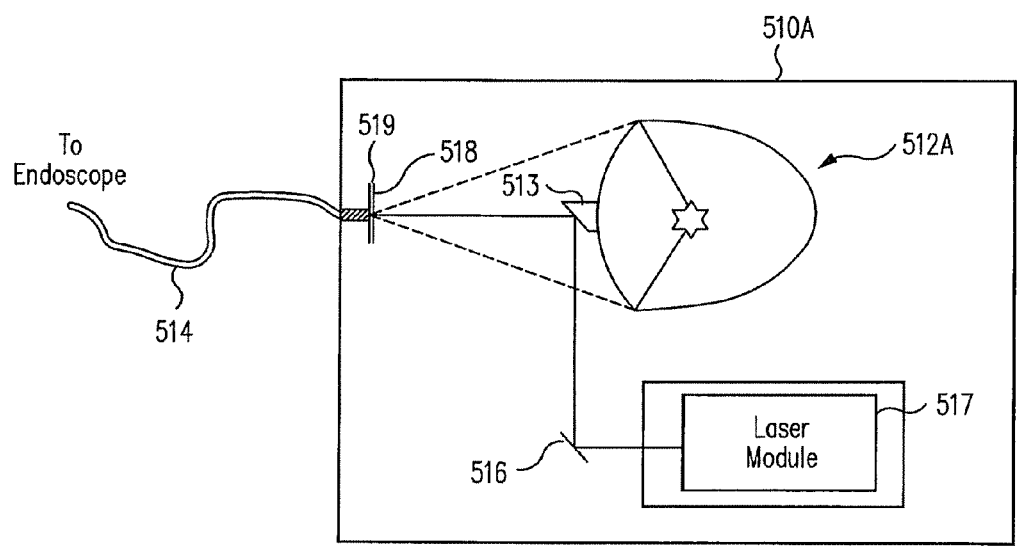
FIGS. 5C to 5E and 5G illustrate aspects of the combination light source and aspects of a fiber optic bundle or bundles used to transport light from the combination light source.
Figure 5D:
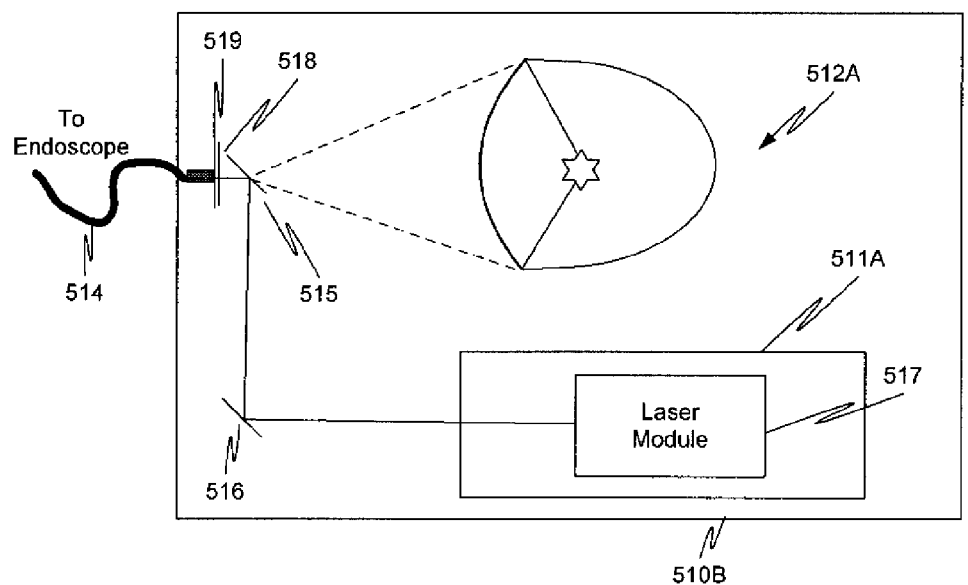
Figure 5E:
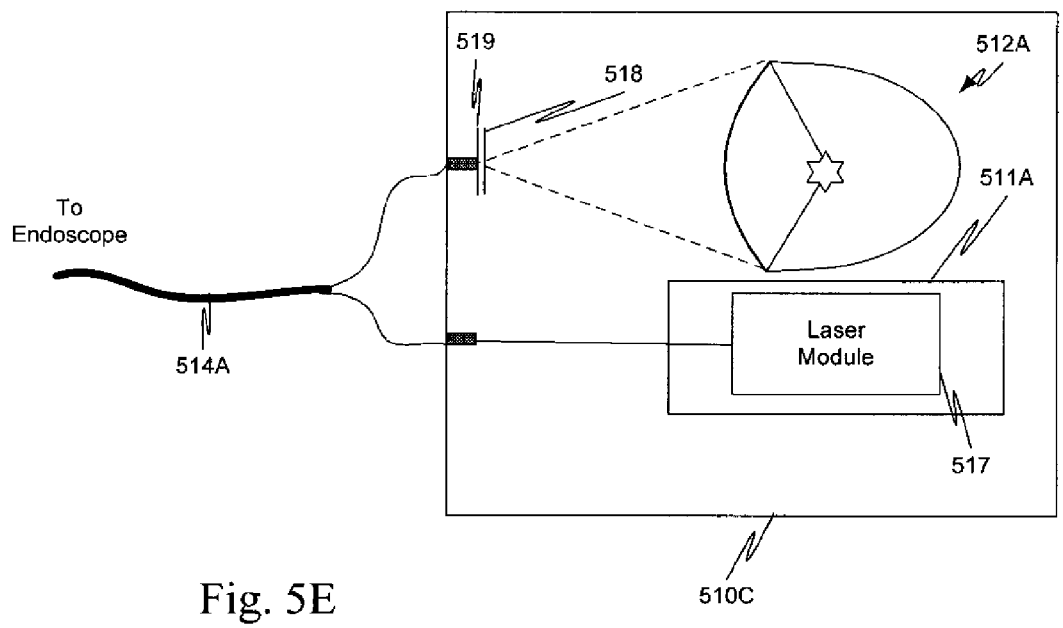

In one aspect, hardware 520 includes at least two camera units 531, 532 (FIG. 5B). One camera unit 532 includes a 3-chip charge-coupled device (CCD) high definition camera and at least a 1-chip CCD camera. Another camera 531 unit also includes a 3-chip charge-coupled device (CCD) high definition camera and at least a 1-chip CCD camera.

In this aspect, camera unit 531 and camera unit 532 are coupled to endoscope 501 by a block 533 that includes a filter and beam splitters, as described more completely below, for preprocessing the light from endoscope 501. In another aspect, the filter can be incorporated in the camera units.

Hardware 520 also includes hardware circuits for performing the functions described more completely below Plurality of computer-based methods 590 are, for example, software executing on a computer processor.

The visible and fluorescence images are simultaneously captured via the same stereoscopic optical path. One camera unit 531 captures visible and fluorescence left images, and second camera unit 532 captures visible and fluorescence right images. In one aspect, camera units 531, 532 are locked together.

Single Stereoscopic Optical Path with Plurality of Cameras—Illumination

Combination light source 510, 510A, 510B, 510C (FIGS. 5A, 5C, 5D, 5E) includes a white light source 512A and another light source 511A. Combination light source 510 is used in conjunction with an illumination path in endoscope 501 to perform illuminate tissue process 201B (FIG. 6). White light source 512A provides light that illuminates tissue 503. Other light source 511A provides light for the alternate image of tissue 503. For example, narrow band light from light source 511A is used to excite tissue-specific fluorophores so that the alternate image is a fluorescence image of specific tissue within tissue 503.

For alternate images that are fluorescence images, if the fluorescence excitation wavelength occurs in the visible spectrum, white light source 512A (FIG. 5B) may be used as both the white light source and as a source to excite the fluorophores. If the fluorescence excitation wavelength occurs outside the visible spectrum (e.g., in the near infrared (IR)) or if additional excitation energy is required at a wavelength in the visible spectrum, a laser module 517 (or other energy source, such as a light-emitting diode or filtered white light) is used to simultaneously illuminate tissue 503.

In one aspect, white light source 512A is the same as white light source 312A and the description of white light source 312A is incorporated herein by reference.

In combination light source 510A (FIG. 5C), a small injection mirror 513 is placed immediately in front of white light lamp unit 512A to reflect excitation light through the focal point of white light lamp unit 512A. A turning mirror 516 is placed between laser module 517 and injection mirror 513 to allow the optical path for the excitation light to be aligned with the white light. This mirror placement results in very high efficiency coupling of the white illumination light along with nearly 100-percent efficiency of laser light coupling into fiber optic bundle 514.

It has been observed that for the various aspects of the combination light sources, when the laser light is injected in a fiber optic bundle, the laser light disperses and illuminates tissue 503 adequately without requiring any other dispersion techniques.

In combination light source 510B (FIG. 5D), a beam splitter 515 (e.g., 50/50 dichroic mirror; various beam splitting technologies are known) is used to incorporate both the white illumination light and laser excitation light from turning mirror 516 into fiber optic bundle 514.

In another aspect (FIG. 5E), the white illumination light from white light source 512A and the laser excitation light from laser module 517 are coupled together using a fiber optic bundle 514A in which several fibers from fiber optic bundle 514A are split off and are separately terminated in a connector to which the laser light can be coupled.

In the case of the da Vinci® Surgical System, the endoscope has two illumination paths. Thus, the fiber optic bundle is split so that two groups of fibers, one carrying white light and the other carrying excitation light are each directed into a different one of the illumination paths. An advantage of this aspect is that for existing da Vinci® Surgical Systems, no excitation light alignment is required and various excitation light sources, as described herein, with various excitation light wavelengths can be easily swapped. For example, if different fluorophores with different excitation wavelengths are to be viewed during the same procedure (e.g., fluorophores associated with a tumor and fluorophores associated with nearby nerves, such as in prostate surgery), the excitation lasers for the different fluorophores can be easily exchanged in the combination light source. In one aspect, the fiber optic bundle or bundles remain connected to the combination light source while a light source is exchanged. Alternatively, two or more excitation light sources can be coupled into the one or more endoscope illumination channels in a similar manner.

In each of combination light sources 510, 510A, 510B, 510C, a band pass filter 518 removes expected fluorescence emission wavelengths from the white illumination light. This increases the contrast of the fluorescence image. The fluorescence image capture chip(s) are prevented from being saturated with reflected light from the tissue at the fluorescence wavelength.

Also, in one aspect, since charge-coupled devices (CCDs) are typically sensitive at wavelengths outside the visible spectrum, a short pass filter 519 removes the unused IR wavelengths beyond the desired emission and visible wavelengths. Removing the unused IR wavelengths increases the contrast for both the visible light image and the fluorescence image. In one embodiment the IR filter from the CCD cameras is removed to increase in sensitivity to the red and near IR wavelengths. The filtered white light is then directed into a fiber optic bundle, as described above, and is coupled into the stereoscopic endoscope for use in illuminating tissue 503 for visible imaging.

Figure 5F:
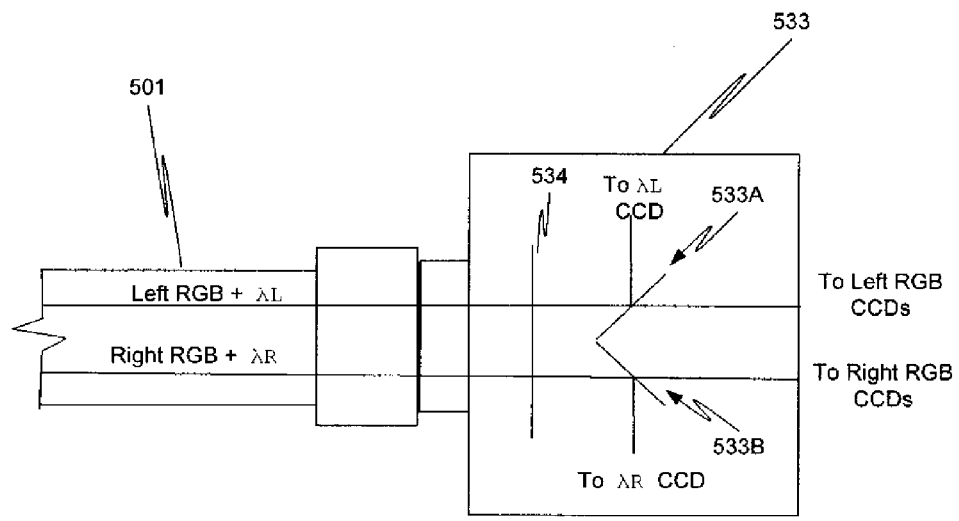
FIG. 5F illustrates one aspect for separating visible and fluorescence images from tissue.
Figure 5G:
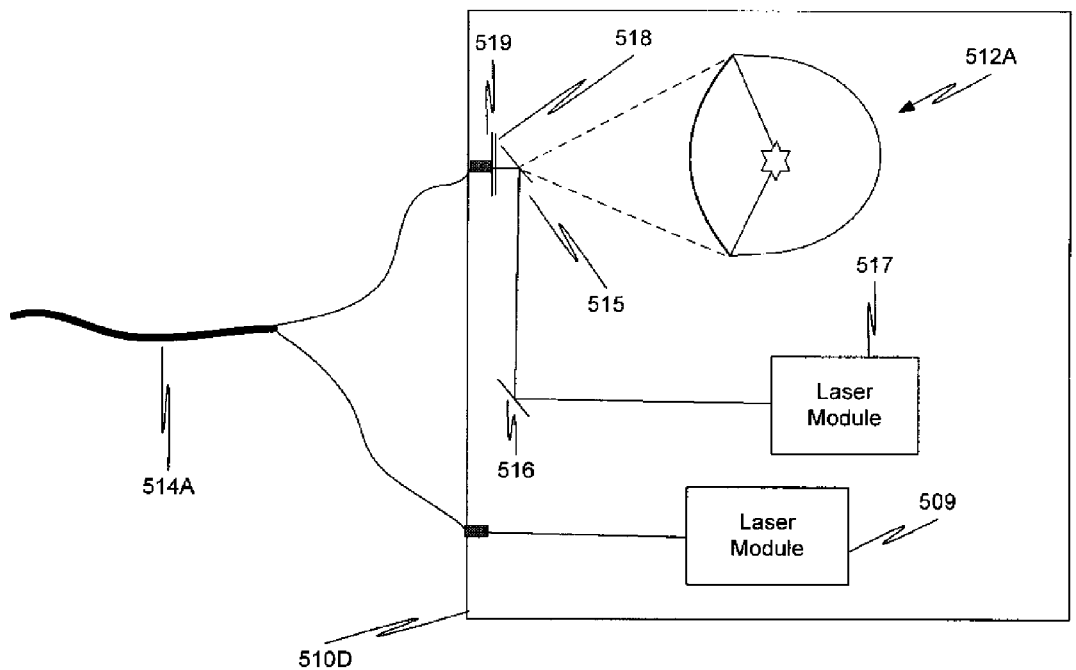

Single Stereoscopic Optical Path with Plurality of Cameras—Image Capture System 120C A fluorescence right image λR and a visible image from tissue 503 (FIGS. 5A, 5F) are transported in one path of the stereoscopic optical path in endoscope 501. Similarly, a fluorescence left image λL and a visible left image from tissue 503 are transported in the other path of the stereoscopic optical path in endoscope 501.

The images from the stereoscopic optical path of endoscope 501 are passed through a fluorescence excitation filter 534 (FIG. 5F) to remove the fluorescence excitation wavelengths from the images. This helps to enhance the contrast between the visible stereoscopic image and the fluorescence image and to improve the quality of the visible image.

The filtered visible left image and the fluorescence left image interact with a beam splitter 533A that splits the filtered images into a visible left image 536 that is captured in CCD 531A and a fluorescence left image 535 that is captured in CCD 531B. In one aspect, CCD 531A is a 3-CCD sensor that captures the left RGB image and CCD 531B is a 1-CCD monochromatic sensor that captures fluorescence left image 535.

Similarly, the filtered visible right image and the fluorescence right image interact with a beam splitter 533B that splits the filtered images into a visible right image 538 that is captured in CCD 532A and a fluorescence right image 537 that is captured in CCD 532B. In one aspect, CCD 532A also is a 3-CCD sensor that captures the right RGB image and CCD 532B is a 1-CCD monochromatic sensor that captures fluorescence right image 537.

Thus, a total of four images—left and right visible and fluorescence images—are captured. An advantage of this aspect is that the alignment between visible and fluorescence images is done in hardware as the chips are physically positioned during manufacturing. In addition, the single CCD can be selected for optimum sensing of the fluorescence image (e.g., in near IR).

In this aspect, block 533 (FIG. 5F) is used to perform pre-process light from tissue operation 202B (FIG. 6). Capture stereoscopic visible and stereoscopic fluorescence images process 203B is performed by capturing the various images in the CCDs as just described.

Single Stereoscopic Optical Path with Plurality of Cameras—Intelligent Image Processing System 130C Since the filtering described above creates a notch in each of visible left image 536 and visible right image 538, spectrum balancer 541, 542 corrects the color balance for the notch. Color balancing is commonly performed in cameras and similar techniques are used herein. For example, the cameras can include a plurality of built-in color balances. Filtering processing 594 selects the correct built-in color balance based upon the fluorescence filter characteristics for use in spectrum balancer 541, 542. Alternatively, filter processing 594 in combination with spectrum balancer 541, 542 could implement the color balancing based upon the fluorescence filter characteristics.

In this aspect, the combination of filter processing 594 and spectrum balancer 541, 542 perform balance spectrum process 605 (FIG. 6) in intelligent image processing 204B.

Single Stereoscopic Optical Path with Plurality of Cameras—Augmented Stereoscopic Display System 140C In one aspect, the augmented stereoscopic video output display may be operated in various modes. The operation of display mode select 560, user interface 593 and the interaction with blend circuit 551, 552 is the same as the above description for display mode select 360, user interface 393 and the interaction with blend circuit 351, 352 and that description is incorporated herein by reference.

Thus, in response to a user input 620 (FIG. 6) the signal from display mode select 560 (FIG. 5A) is provided to a display mode check operation 608 in a user interface 593 that in turn provides a control signal to blend circuits 551 and 552. If the surgeon selects visible only, spectrum balanced visible left image 536 and spectrum balanced visible right image 538 are presented in stereoscopic display 550 via stereoscopic display of visible image process 611 (FIG. 6) in generate stereoscopic video display of tissue process 205B.

If the surgeon selects visible plus fluorescence, in blend process 609, blend circuit 551 blends fluorescence left image 535 and spectrum balanced visible left image 536, while blend circuit 552 blends fluorescence right image 537 and spectrum balanced visible right image 538. Different image blending options, such as alpha blending, can be implemented in blend circuits 551, 552. The outputs of blend circuits 551, 552 are presented in stereoscopic display 550 via stereoscopic display of visible and fluorescence images process 610 (FIG. 6). The displayed fluorescence images can be processed in ways equivalent to those described above with respect to FIGS. 3A to 4 and so are not repeated here.

The above description of a camera unit with two cameras is illustrative only and is not intended to be limiting. For example, each camera unit could be a single camera with optics that split the incoming beam. In this aspect, two chips of a 3-CCD image sensor are used to capture the visible image, and the third chip is used to capture the fluorescence image. In this aspect, a prism (e.g., a trichroic beam splitter prism assembly) that directs light to the three CCD chips is designed such that the fluorescence wavelength light is reflected toward one CCD chip and the visible light is separated onto the other two CCD chips. Full color for the visible images can be reconstructed from the two CCD channels, as is commonly done. This aspect has the hardware alignment advantages described above.

In another aspect, features of intelligent image processing from FIG. 3A can be combined with aspects of FIG. 5A. For example, combination light source 510D (FIG. 5G) includes white light source 512A and laser module 517 configured, as described above with respect to FIG. 5D, to project the laser and white illumination light into one set of fibers in fiber optic cable 514A. A second laser module 509 provides a beam that is injected on a second set of fibers within fiber optic cable 514A. The light from two lasers 517, 509 excite different fluorescence emissions and so each optical path in endoscope 501 includes a visible image and two fluorescence images.

In this aspect, beam splitter 533A is configured to separate the visible left image and the fluorescence left image for the first fluorescence image. Beam splitter 533B is configured to separate the visible right image and the fluorescence right image for the second fluorescence image.

Thus, in this aspect, the fluorescence left image of the first fluorescence image is captured in CCD 531B and the fluorescence right image for the second fluorescence image is captured in CCD 532B. In each case, it is necessary to generate the other fluorescence image for the stereoscopic display.

The fluorescence left image of the first fluorescence image is spatially registered with the visible right image and then an image warper is used, based on the registration, to generate the fluorescence right image for the first fluorescence image.

Similarly, the fluorescence right image of the second fluorescence image is spatially registered with the visible left image and then an image warper is used, based on the registration, to generate the fluorescence left image for the second fluorescence image. Thus, the visible left image, visible right image, fluorescence left first image, fluorescence right first image, fluorescence left second image, and fluorescence right second image are available. Augmented stereoscopic display system 140B of FIG. 3E is used to display the various images.

Thus, in general, for aspects in which the fluorescence image information is captured in only one stereoscopic channel, a fluorescence image for the other channel must be generated to produce a stereoscopic fluorescence image display for the surgeon that is correlated to the stereoscopic visible image video. If the visible and fluorescence images share the same optical path, stereo matching of visible images is used to generate the fluorescence image for the second stereoscopic channel. If the visible and fluorescence images use different optical paths, the visible and fluorescence images are registered to each other in the channel that includes the captured fluorescence images, and then stereo matching of visible images is applied to generate the fluorescence images for the second channel.

Single Stereoscopic Optical Path with a Camera Unit

In one exemplary process, both visible and fluorescence images are captured in the right stereoscopic channel, and only a visible image is captured in the left channel. For example, in the embodiment of FIG. 7A, a robotic surgical system (not shown) includes a single stereoscopic optical path for transporting light from tissue 703 to augmented stereoscopic vision system 700. Light from the single stereoscopic optical path is used to generate a real-time stereoscopic video display of tissue 703 for the surgeon operating the robotic surgical system.

The stereoscopic video display includes a three-dimensional view of tissue 703 augmented with an alternate image to highlight regions of interest in tissue 503 such as diseased portions of tissue 503 and/or other tissue of interest, such as a nerve or organ. In one aspect, the alternate image is provided to only one eye, e.g., the right eye, in the stereoscopic view so that the surgeon can compare the left eye and right eye images without having to toggle between the augmented and non-augmented stereoscopic view. In addition, this aspect also provides a stereoscopic view with a stereoscopic alternate view. This is accomplished without the beam splitters used in FIG. 5a for example. In one aspect, the alternate view is presented in a specific color, e.g., blue.

In this example, a single endoscope 701 provides the stereoscopic optical path from tissue 703 to hardware 720. Endoscope 701 has two light channels making up the stereoscopic optical path and at least one illumination channel for providing light to tissue 701. While it is not shown, endoscope 701 is held and moved by the robotic surgical system. See FIG. 1 for example.

Figure 7A:
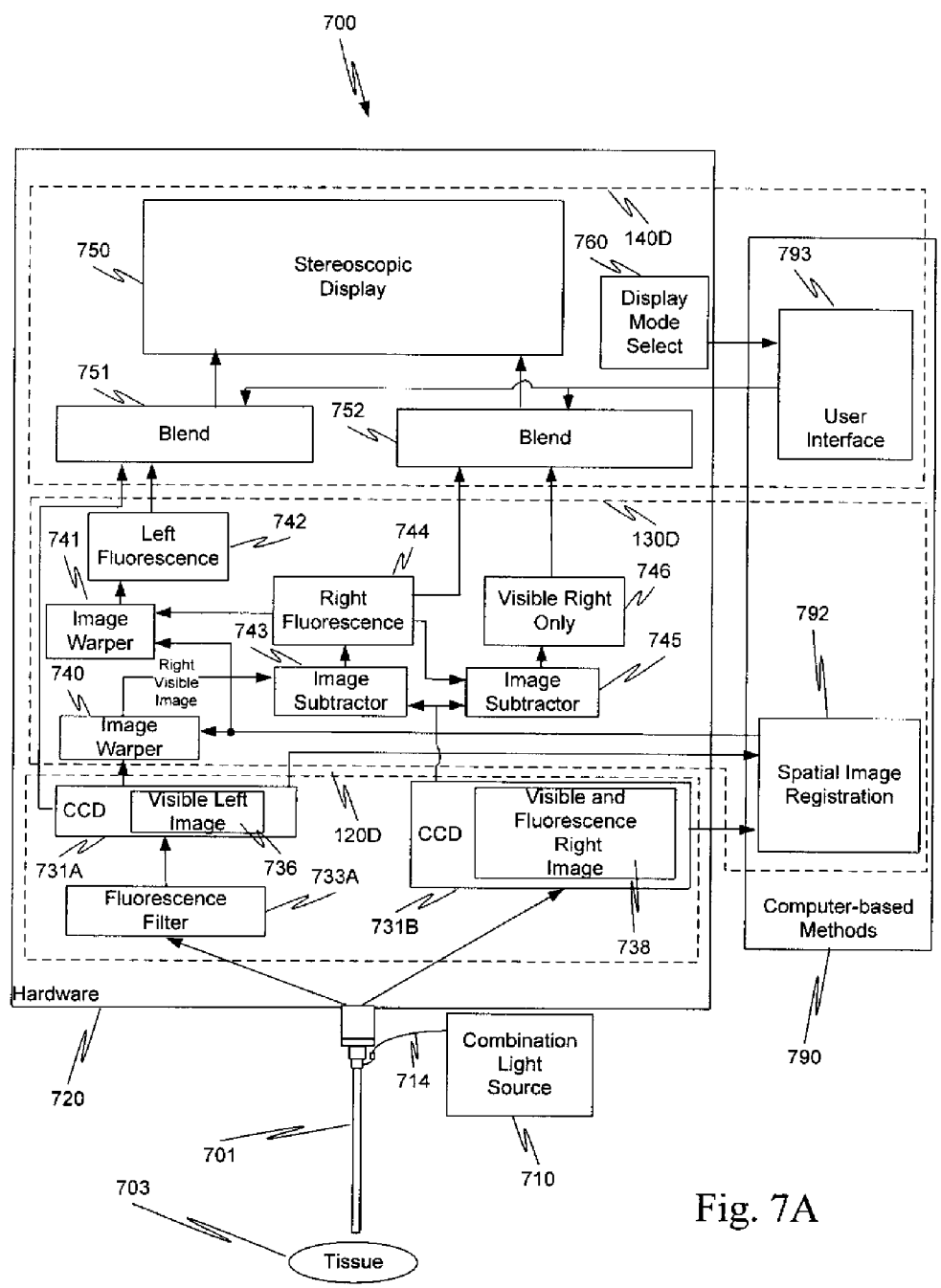
FIG. 7A is a schematic view that illustrates hardware and software (image processing and user interface) aspects of the use of channel division with a single stereoscopic optical path for capturing, processing, and outputting blended real-time stereoscopic visible and fluorescence images in a minimally invasive surgical robotic system.

In this example, augmented stereoscopic vision system 700 includes a combination light source 710, hardware 720, and a plurality of computer-based methods 790. As shown in FIG. 7A, a portion of hardware 720 makes up image capture system 120D. Another portion of hardware 720 and a portion of plurality of computer-based methods 790 make up intelligent image processing system 130D. Yet another portion of hardware 720 and another portion of plurality of computer-based methods 790 make up augmented stereoscopic display system 140D. Within image capture system 120D and intelligent image processing system 130D, the portions that process visible images make up a visible imaging system while the portions that process fluorescence images make up an alternate imaging system.

Figure 8:
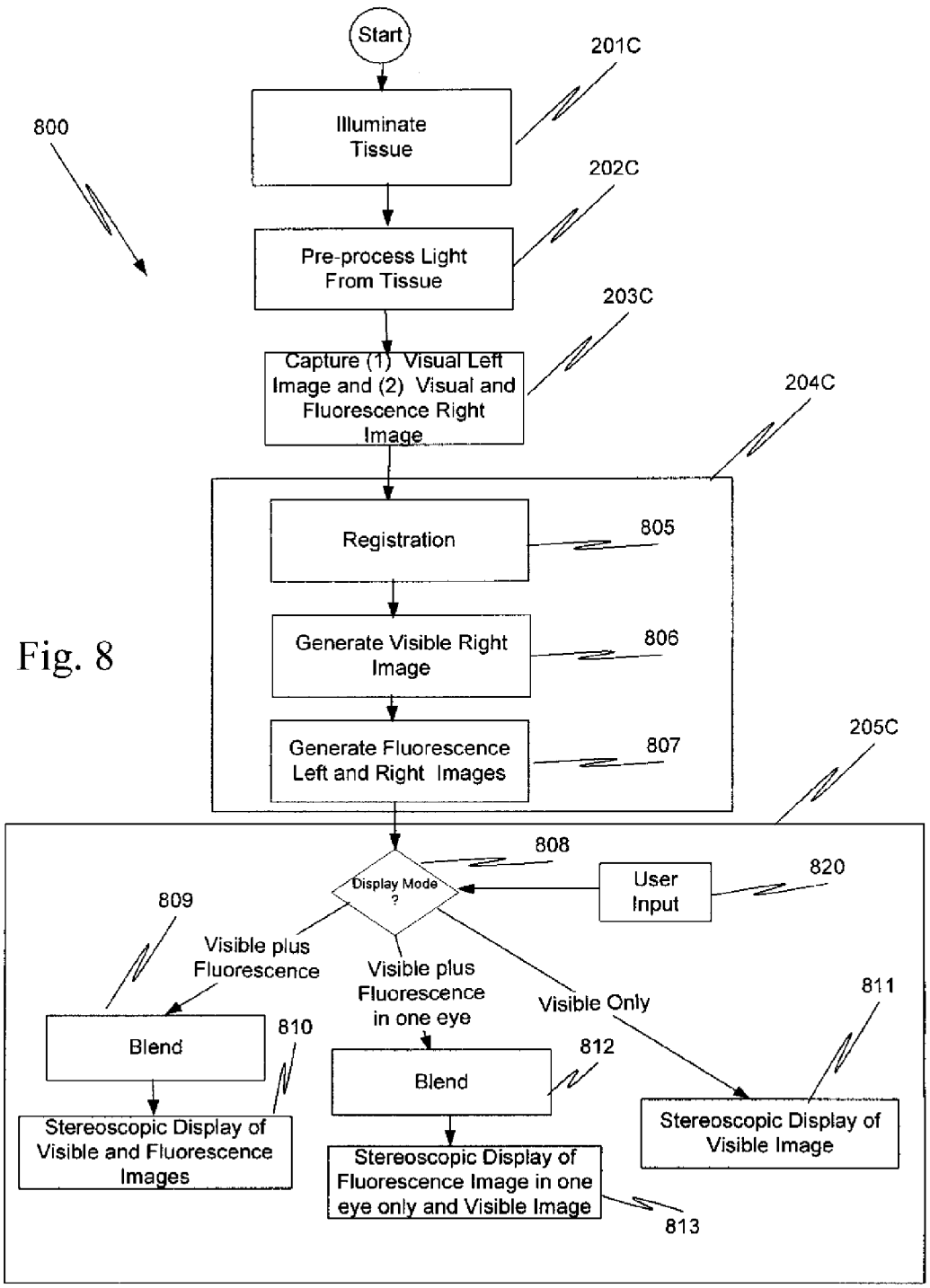
FIG. 8 is process flow diagram of a process performed using, for example, the augmented stereoscopic visualization system for a minimally invasive surgical robot of FIG. 7A.

Also, method 800 of FIG. 8 is implemented using augmented stereoscopic vision system 700. As shown in FIG. 8, method 800 includes a plurality of separate processes. Method 800 is one implementation of method 200 (FIG. 2).

Figure 7B:
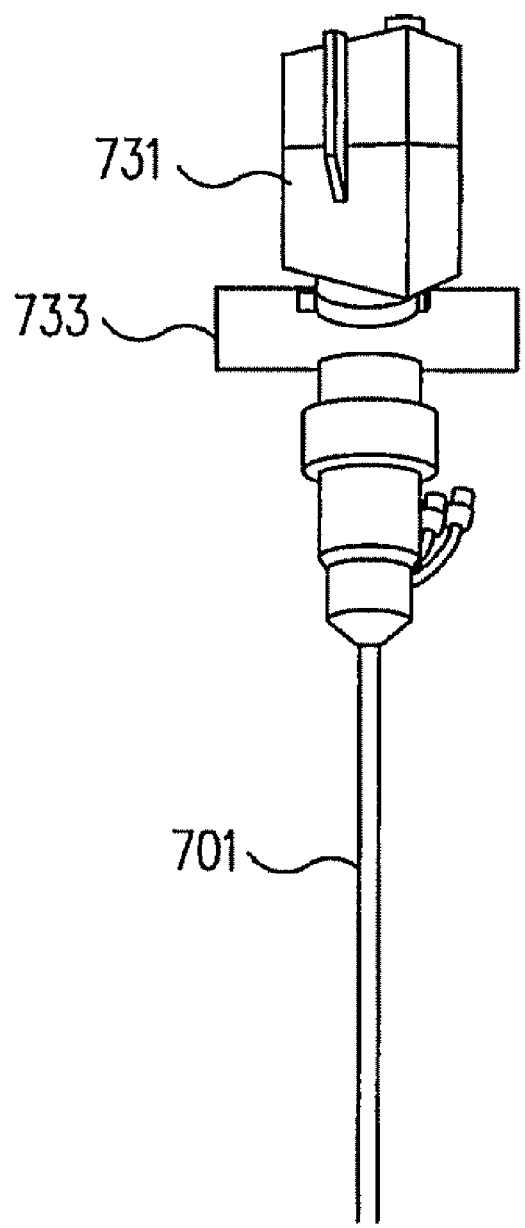
FIG. 7B is a more detailed view showing an endoscope with a single camera unit coupled to the endoscope.

In one aspect, hardware 720 includes a single camera unit 731 (FIG. 7B). Camera unit 731 includes a 3-chip charge-coupled device (CCD) sensor for each optical path of endoscope 701.

In this aspect, camera unit 731 (FIG. 7B) is coupled to endoscope 701 by a block 733 that includes a filter 733A (FIG. 7A) for preprocessing the light from the left optical path of the stereoscopic optical path of endoscope 701. In another aspect, the filter can be incorporated in the camera unit. The visible right image with the fluorescence image and the visible left image are simultaneously captured via the same stereoscopic optical path.

Hardware 720 also includes hardware circuits for performing the functions described more completely below. Plurality of computer-based methods 790 are, for example, software executing on a computer processor.

Single Stereoscopic Optical Path with a Camera Units Illumination

Combination light source 710 with fiber optic bundle 714 is equivalent to any one of combination light sources 510A (FIG. 5C), 510B (FIG. 5D) and 510C (FIG. 5E) and the associated fiber optic bundles, as well as the various aspects described above with respect to the implementation of combination light source 310A (FIG. 3C). Rather than repeat the description of those combination light sources that description is incorporated herein by reference. Combination light source 710 is used in conjunction with an illumination path in endoscope 701 to perform illuminate tissue process 201C (FIG. 8)

Single Stereoscopic Optical Path with a Camera—Image Capture System 120D

The visible left image from tissue 703 (FIG. 7A) is captured from a left optical channel of the stereoscopic optical path in endoscope 701, and the visible right image combined with the fluorescence image from tissue 703 is captured from a right optical channel of the stereoscopic optical path in endoscope 701.

To capture only the visible left image, the light from the left optical channel is filtered by fluorescence filter 733A to remove the fluorescence wavelength(s) from visible left image 736 that is captured in a left CCD 731A. A visible and fluorescence right image 738 is captured in a right CCD 731B. Left CCD 731A captures red, green, and blue images for visible left image 731. Similarly, right CCD 731B captures red, green, and blue images for visible and fluorescence right image 738.

In this aspect, filter 733A performs pre-process light from tissue operation 202C (FIG. 8). Capture visible left image and visible and fluorescence right images process 203C is performed by capturing the various images in the CCDs as just described.

Single Stereoscopic Optical Path with a Camera Unit—Intelligent Image Processing System 130D Spatial image registration 792 receives as inputs, each of captured images 736 and 738. Again, spatial image registration registers the images taken from different viewing angles so that any two corresponding pixels from both images, based on the registration results, refer to the same scene point in the world. Spatial image registration 792 is performed in registration process 805 (FIG. 8) in intelligent processing 204C.

In one aspect, spatial image registration 792, for the image modalities in Table 4, is the same as that presented in FIG. 3D.

TABLE 4

| | Input for matching | | |
|---|---|---|---|
| Image Modalities | Raw Image | Gradient Images | Image Features |
| Visible against visible + fluorescence | Yes | Yes | Yes |

In spatial image registration 392A (FIG. 3D), two of the captured images, e.g., a visible left image and a visible and fluorescence right image, are input as Image 1 to pre-processing 370 and Image 2 to pre-processing 371. Depending on the feature being used in matching the visible against the visible and fluorescence, pre-processing 370, 371 generates the appropriate information. For example, for gradient images, the gradient of the raw images along the X and Y directions is generated. Similarly, image features are obtained by pre-processing raw images. Many image features are available, for example, a histogram of image intensities in a local region.

The results from pre-processing 370, 371 are supplied to matching process 372. There are many methods available for matching process 372. A first example is a normalized cross-correlation of either raw images or gradient images computed using all pixels in a small region surrounding pixel at location (x, y). Another example is mutual information based matching with the inputs being intensity histograms.

The output of matching process 372 is a displacement (dx, dy) that gives the best matching score after moving the pixel at (x, y) from one input image to the other input image. If the displacement (dx, dy) is generated for all the pixels in the inputs, the result is called a disparity map consisting of two images of dx (x, y) and dy (x, y).

The pixel by pixel registration for the left and right images in spatial image registration 792 is available to image warper 740 and image warper 741. Image warper 740 also receives as input captured visible left image 736.

Using the spatial image registration information and visible left image 736, image warper 340 generates a visible right image and in turn, the visible right image is supplied to image subtractor 743. Image subtractor 743 subtracts the visible right image from captured visible and fluorescence image 738 to generate fluorescence right image 744. Using the spatial image registration information and fluorescence right image 744, image warper 741 generates a fluorescence left image 742. Image subtractor 745 subtracts fluorescence right image 744 from captured visible and fluorescence image 738 to generate visible right image 746.

Thus, in this aspect, the combination of elements 792, 740, 743, 744, 736, 738 and 745 are used in generate visible right image process 806 (FIG. 8). The combination of elements 792, 740, 743, 736 and 738 are used to generate the fluorescence right image in generate fluorescence left and right images process 807, while the combination of elements 792, 740, 743, 744, 741, 736 and 738 are used to generate the fluorescence left image in generate fluorescence left and right images process 807.

The processes described above are illustrative only and are not intended to be limiting. Visible right image only 746 can be generated in a variety of ways. For example, for regions of visible right image only 746 that contain only visible data, the visible data can be taken from captured right image 738 and for regions that contain fluorescence, the regions are warped using the captured left image.

Again, note that while this description is necessarily linear and describes a single pass through the processing, the processes are occurring in real-time and the various images are being continuously updated to reflect the current state of tissue 703 as observed via endoscope 701. Also, the various processes can proceed in parallel if the necessary information is available.

Single Stereoscopic Optical Path with a Camera Unit—Augmented Stereoscopic Display System 140D In one aspect, the augmented stereoscopic video output display may be operated in various modes. For example, in a first mode, only stereoscopic visible images are output to the surgeon, as in the da Vinci® Surgical System. In a second mode, a fluorescence image is superimposed on the visible images to create an augmented image, and the stereoscopic augmented image is output to the surgeon. In a third mode, a visible image for one eye of the stereoscopic display is blended with the corresponding fluorescence image for that eye and only the visible image is presented for the other eye. Thus, the stereoscopic augmented view has an augmented view for one eye and a normal view for the other eye in the stereoscopic display.

The video output may be toggled between these modes by using, e.g., a foot switch, a double click of the master grips that control the surgical instruments, voice control, and other like switching methods. The toggle for switching between the various modes is represented in FIG. 7A as display mode select 760.

In response to a user input 820 (FIG. 8) the signal from display mode select 760 FIG. 7A) is provided to a display mode check operation 808 in a user interface 793 that in turn provides a control signal to blend circuit 751 and blend circuit 752. If the surgeon selects visible only, visible left image 736 and visible right image 746 are presented in stereoscopic display 750 via stereoscopic display of visible image process 811 (FIG. 8).

If the surgeon selects visible plus fluorescence in the right eye only, in blend process 812, blend circuit 751 passes visible left image 736 to stereoscopic display 750, while blend circuit 752 blends fluorescence right image 744 and visible right image 746. Alternatively, blend circuit 752 could pass visible and fluorescence right image 738 to stereoscopic display 750. The outputs of blend circuits 751, 752 are presented in stereoscopic display 750 via stereoscopic display of fluorescence image in one eye only and visible image process 813 (FIG. 8) in generate stereoscopic video display of tissue process 205C.

If the surgeon selects visible plus fluorescence, in blend process 809, blend circuit 751 blends fluorescence left image 742 and visible left image 736, while blend circuit 752 blends fluorescence right image 744 and visible right image 746.

Different image blending options, such as alpha blending, can be implemented in blend circuits 751, 752. The outputs of blend circuits 751, 752 are presented in stereoscopic display 750 via stereoscopic display of visible and fluorescence images process 810 (FIG. 8)

The techniques previously described for enhancing the fluorescence image in the stereoscopic display are also applicable to this embodiment.

Also, in the above described aspect, the left and right images could be reversed. Thus, the left image is an example of a first image and the right image is an example of a second image.

Time Division—Single Stereoscopic Optical Path with a Camera Unit

In still another aspect, the visible and fluorescence images are captured via the same stereoscopic optical path, but image capture is time division multiplexed. In this aspect, the same camera unit captures data for both the visible and fluorescence images, but at different times. This time division is implemented by synchronizing a light source on/off with the video frame capture.

Figure 9A:
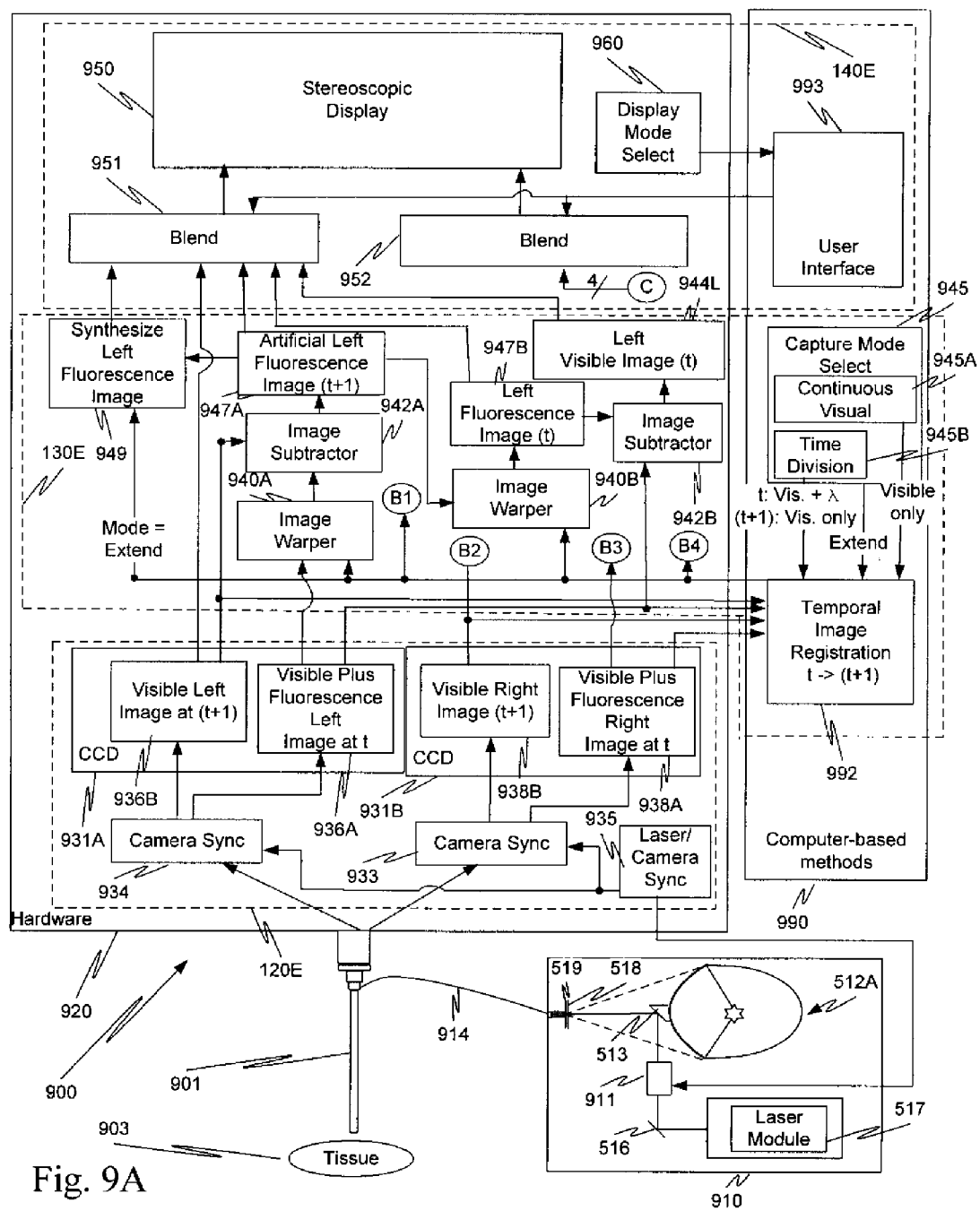
FIGS. 9A and 9B are a schematic view that illustrates hardware and software (image processing and user interface) aspects of the use of time division with a single stereoscopic optical path for capturing, processing, and outputting blended stereoscopic visible and fluorescence images in a minimally invasive surgical robotic system.
Figure 9B:
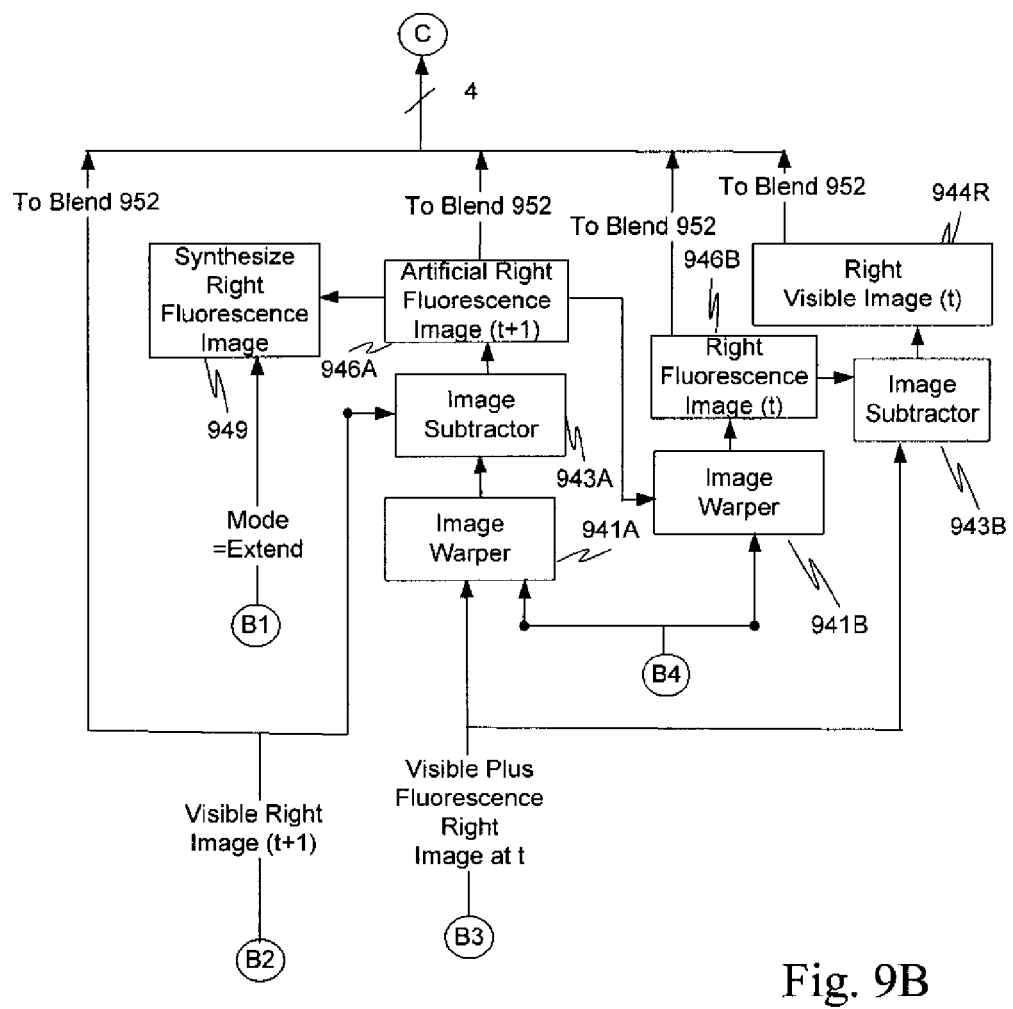

For example, in the embodiment of FIGS. 9A and 9B, a robotic surgical system (not shown) includes a single stereoscopic optical path for transporting light from tissue 903 to augmented stereoscopic vision system 900. Light from the single stereoscopic optical path is used to generate a real-time stereoscopic video display of tissue 903 for the surgeon operating the robotic surgical system. The stereoscopic video display includes a three-dimensional view of tissue 903 blended with an alternate image to highlight regions of interest in tissue 903 such as diseased portions of tissue 903 and/or other tissue of interest, such as a nerve or organ.

In this example, a single endoscope 901 provides the stereoscopic optical path from tissue 903 to hardware 920. Endoscope 901 has two light channels making up the stereoscopic optical path and at least one illumination channel for providing light to tissue 903. While it is not shown, endoscope 901 is held and moved by the robotic surgical system. See FIG. 1 for example.

In this example, augmented stereoscopic vision system 900 includes a combination light source 910, hardware 920, and a plurality of computer-based methods 990. As shown in FIGS. 9A and 9B, a portion of hardware 920 makes up image capture system 120E. Another portion of hardware 920 and a portion of plurality of computer-based methods 990 make up intelligent image processing system 130E. Yet another portion of hardware 920 and another portion of plurality of computer-based methods 990 make up augmented stereoscopic display system 140E. Within image capture system 120E and intelligent image processing system 130E, the portions that process visible images make up a visible imaging system while the portions that process fluorescence images make up an alternate imaging system.

Figure 10A:
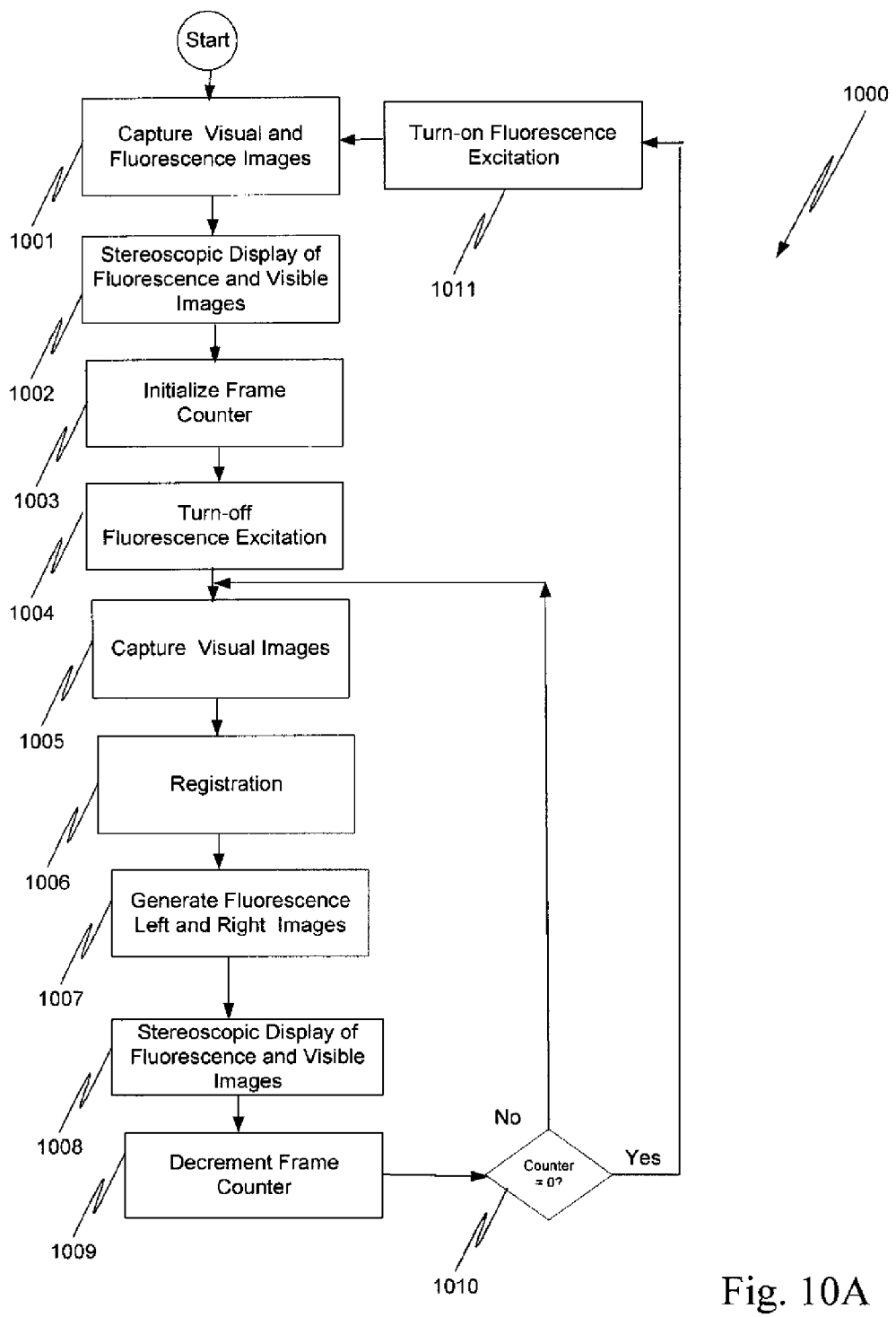
FIG. 10A is a process flow diagram of a process performed using, for example, the augmented stereoscopic visualization system for a minimally invasive surgical robot of FIG. 9A.

Also, method 1000 of FIG. 10A is implemented using augmented stereoscopic vision system 900. As shown in FIG. 10A, method 1000 includes a plurality of separate processes. Method 1000 is one implementation of method 200 (FIG. 2).

In one aspect, hardware 920 includes a single camera unit such as camera unit 731 (FIG. 7B). Camera unit 731 includes a 3-chip charge-coupled device (CCD) sensor for each optical path of endoscope 901.

Hardware 920 also includes hardware circuits for performing the functions described more completely below. Plurality of computer-based methods 990 are, for example, software executing on a computer processor. In the following description, multiple hardware units are described that perform the same function. This is for ease of description only and is not intended to require the exact number shown. Depending on the implementation, a single instance of the hardware unit could be used, or alternatively a number less than the number shown could be used so long as the hardware performs within a relevant time period.

Time Division—Single Stereoscopic Optical Path with a Camera Unit—Illumination Combination light source 910 (FIG. 9A) with fiber optic bundle 914 is similar to any one of combination light sources 510A (FIG. 5C), 510B (FIG. 5D) and 510C (FIG. 5E) and the associated fiber optic bundles, as well as the various aspects described above with respect to the implementation of combination light source 310A (FIG. 3C). Accordingly, the description of those combination light sources is incorporated herein by reference. However, combination light source 910 includes a means for turning off and on at least one of the light sources.

As an example, combination light source 510A is selected as the starting point for combination light source 910 and a Pockels cell 911 is inserted in the laser light's path between turning mirror 516 and injection mirror 513. Pockels cell 911 is connected to a laser/camera sync circuit 935. As explained more completely, in one aspect at a time t, Pockels cell 911 receives a signal from laser/camera sync circuit 935 so that the laser beam passes through Pockels cell 911 and is injected into fiber optic cable 914 with the light from white light source 512A. Here, time t is associated with a frame, while time (t+1) is associated with a different frame.

At a time (t+1), Pockels cell 911 receives a signal from laser/camera sync circuit 935 so that the laser beam is blocked by Pockels cell 911 and only the light from white light source 512A is injected into fiber optic cable 914. Thus, for a first time interval, tissue 903 is illuminated with white light and with light that simulates fluorescence from tissue 903 and then for a second time interval, immediately following the first time interval, tissue 903 is illuminated with only the white light. In this example, the laser beam is modulated on and off. However, in view of the following description, system 900 could be implemented with the white light source modulated on and off and with the laser beam maintained continuously on.

Time Division—Single Stereoscopic Optical Path with a Camera Unit—Image Capture System 120E Laser/camera sync circuit 935 also provides a signal to camera sync 934 and 933 in image capture system 120E. In response to that signal, camera sync 934 causes a frame to be captured in left CCD sensor 931A and camera sync 933 causes the frame to be captured in right CCD sensor 931B. Each CCD sensor is a 3-chip CCD sensor and so the captured image has red, green and blue color components. FIG. 9B is an example of the synchronization between combination light source 910 and the frame capture.

For example, at time t, tissue 903 is illuminated with both the white light and the laser light and a signal Left Optical Path Capture, Right Optical Path Capture is sent to camera sync 934 and 933, respectively. Thus, at time t, a first stereoscopic frame 936A of visible left image and fluorescence left image λL is captured in left CCD 931A. Also, at time t, a first stereoscopic frame 938A of visible right image and fluorescence right image λR is captured in right CCD 931B.

For example, at time (t+1), tissue 903 is illuminated with only the white light; the laser light is turned off; and a signal Left Optical Path Capture, Right Optical Path Capture is sent to camera sync 934 and 933, respectively. Thus, at time (t+1), a second stereoscopic frame 936B of the visible left image is captured in left CCD 931A. Also, at time (t+1), a second stereoscopic frame 938A of the visible right image is captured in right CCD 931B.

Figure 9C:
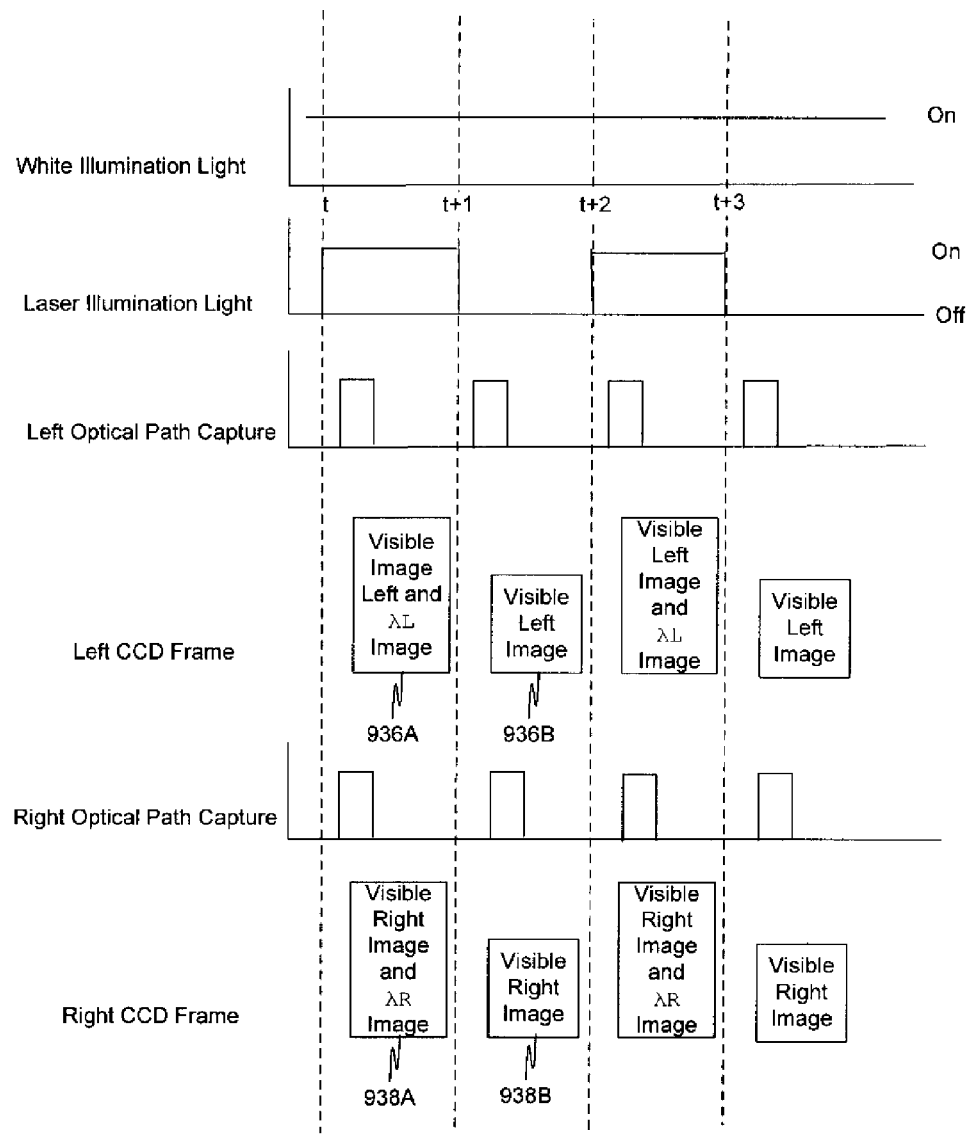
FIG. 9C illustrates one aspect of the timing, synchronization, and capture of the system in FIGS. 9A and 9B.

As illustrated in FIG. 9C, for this example, the capture process continues and so the fluorescence image capture rate is one half the capture rate of the visible image, e.g., visible data is collected in every frame while fluorescence and visible data is collected in every other frame. This capture rate is illustrative only and in view of this disclosure an appropriate capture rate for the fluorescence image can be chosen.

The left images from tissue 903 (FIG. 9A) are captured from a left optical channel of the stereoscopic optical path in endoscope 901, and the right images from tissue 903 are captured from a right optical channel of the stereoscopic optical path in endoscope 901.

In the example of FIGS. 9A and 9B, two frames are shown as being captured by the CCD sensor. This is for ease of illustration only and is not intended to be limiting. As is known, prior to capture of the frame at time (t+1), the frame captured in the CCD sensor could be moved to a buffer, for example, for the processing described more completely below.

Time Division—Single Stereoscopic Optical Path with a Camera Unit—Intelligent Image Processing System 130E Since the fluorescence and visible images are captured at different frame rates, temporal registration 992 is used in synchronization of the fluorescence images with the visible images. In this example, spatial registration is not needed. However, in one aspect, where spatial registration is used, the spatial registration is done prior to temporal registration 992. As described more completely below, the information from temporal registration is used in applying a transformation to generate missing fluorescence frames through image warping as well as in generating individual images when the visible and fluorescence images are captured together.

Thus, in this example, temporal image registration 992 receives as inputs, each of captured frames 936A, 936B, 938A and 938B. Temporal image registration 992 also receives an input from capture mode select 945. In this example, three capture modes are considered. A first capture mode is, as described above, a time division mode 945B where visible plus fluorescence images and visible images only are captured. In a second capture mode, continuous visual mode 945A, only visible images are captured and the fluorescence excitation light source is held off. In the third capture mode, referred to as an extended mode, only visible images are captured because the fluorescence images are no longer available and so the fluorescence left and right images are synthesized, as described more completely below. Note that while in the second and third capture modes, the setup for the modes is different, the capture, processing and display processes are effectively equivalent.

Using the temporal image registration information of visible left image 936B at time (t+1) with captured visible left image combined with fluorescence left image 936A at time t, image warper 940A generates a combined visible left image and fluorescence left image for time (t+1). Image warper 940A compensates for any motion between times t and (t+1).

The generated combined visible left image and fluorescence left image for time (t+1) is supplied to image subtractor 942A as a first input. Image subtractor 942A receives visible left image 936B at time (t+1) from left CCD 931A as a second input. Image subtractor 942A subtracts visible left image 936B from the generated combined visible left image and fluorescence left image for time (t+1) to generate artificial fluorescence left image 947A at time (t+1).

The generated fluorescence left image 947A at time (t+1) is an input to image warper 940B. Image warper 940B also receives temporal image registration information as an input. Image warper 940A generates a fluorescence left image 947B for time t from generated fluorescence left image 947A at time (t+1). Image warper 940B compensates for any motion between times t and (t+1).

Generated fluorescence left image 947B for time t is supplied to image subtractor 942B as a first input. Image subtractor 942A receives captured visible left image combined with fluorescence left image 936A at time t from left CCD 931A as a second input. Image subtractor 942B subtracts generated fluorescence left image 947B for time t from captured visible left image combined with fluorescence left image 936A at time t to generate visible left image 944L at time t.

Using the temporal image registration information of visible right image 938B at time (t+1) with captured visible right image combined with fluorescence right image 938A at time t, image warper 941A (FIG. 9B) generates a combined visible right image and fluorescence right image for time (t+1). Image warper 941A compensates for any motion between times t and (t+1).

The generated combined visible right image and fluorescence right image for time (t+1) is supplied to image subtractor 943A as a first input. Image subtractor 932A receives visible right image 938B at time (t+1) from right CCD 931B as a second input. Image subtractor 943A subtracts visible right image 938B from the generated combined visible right image and fluorescence right image for time (t+1) to generate artificial fluorescence right image 946A at time (t+1).

The generated artificial fluorescence right image 946A at time (t+1) is an input to image warper 941B. Image warper 941B also receives temporal image registration information as an input. Image warper 941B generates a fluorescence right image 946B for time t from generated artificial fluorescence right image 946A at time (t+1). Image warper 941B compensates for any motion between times t and (t+1).

Generated fluorescence right image 946B for time t is supplied to image subtractor 943B as a first input. Image subtractor 943A receives captured visible right image combined with fluorescence right image 938A at time t from right CCD 931B as a second input. Image subtractor 943B subtracts generated fluorescence right image 946B for time t from captured visible right image combined with fluorescence right image 938A at time t to generate visible right image 944R at time t.

Fluorescence left image 947B and fluorescence right image 946B are a stereoscopic pair of fluorescence images. Similarly, artificial fluorescence left image 947A and artificial fluorescence right image 946A are a stereoscopic pair of fluorescence images.

In FIGS. 9A and 9B, the fluorescence and visible data for the frames at times t and (t+1) are shown as both being supplied to blend circuits 951 and 952. This is for ease of understanding only. The two frames would be provided in the proper sequence so that the stereoscopic display presented to the surgeon flows in the proper time sequence even though the video sequence may be delayed by one or more frames to allow for the processing described above.

When capture mode select 945 (FIG. 9A) is in continuous visual mode 945A, laser module 517 is turned off and so only visible images are captured. In this mode, a fluorescence image is not generated or displayed, and so the captured visible images are simply displayed on stereoscopic display 950 in the normal way.

Augmented system 900, in this example, also includes the ability to provide a fluorescence image indicating tissue of interest for a long period of time, even after an agent in the tissue no long fluoresces. In this situation irrespective of the configuration of combination light source 910, only visible images are captured and registered in temporal registration 992. This mode is referred as the extended mode.

In the extended mode, temporal registration 992 provides the image registration information to synthesize fluorescence left image 949 and to synthesize fluorescence right image 948 in the extended mode. Synthesize fluorescence left image 949 also receives as input the last fluorescence left image generated, i.e., fluorescence left image 947A. Synthesize fluorescence left image 949 generates a synthesized fluorescence left image by using the temporal registration information to move fluorescence left image 947A into the correct position with respect to the current visible only left image. In one aspect, the process used to generate a synthetic fluorescence left image is equivalent to that just described to generate an artificial fluorescence left image.

Similarly, synthesize fluorescence right image 948 also receives as input the last fluorescence right image generated, i.e., fluorescence right image 946A. Synthesize fluorescence right image 948 generates a synthesized fluorescence right image by using the registration information to move fluorescence right image 946 into the correct position with respect to the current visible only right image. In one aspect, the process used to generate a synthetic fluorescence right image is equivalent to that just described to generate an artificial fluorescence right image.

Again, note that while this description is necessarily linear and describes a single pass through the processing, the processes are repeating in real-time and the various images are being continuously updated to reflect the current state of tissue 903 as observed via endoscopes 901 using the processes just described.

Time Division—Single Stereoscopic Optical Path with a Camera Unit—Augmented Stereoscopic Display System 140E In one aspect, the augmented stereoscopic video output display may be operated in various modes. For example, in a first mode, only stereoscopic visible images are output to the surgeon, as in the da Vinci® Surgical System. In a second mode, a fluorescence image is superimposed on the visible images to create an augmented image, and the stereoscopic augmented image is output to the surgeon.

The video output may be toggled between these modes by using, e.g., a foot switch, a double click of the master grips that control the surgical instruments, voice control, and other like switching methods. The toggle for switching between the two modes is represented in FIG. 9A as display mode select 960 which generates a signal that is provided to user interface 993 that in turn outputs a signal to blend circuits 951, 952, which function in the same way as previously described for the other blend circuits.

The techniques previously described for enhancing the fluorescence image in the stereoscopic display are also applicable to this embodiment.

In addition, in some aspects, another display mode that generates an augmented display with fluorescence and visible images may be implemented. This display mode can be a variation of the first display mode or a completely different display mode. In either case, the fluorescence image flickers on and off in the stereoscopic display and so is not continuously displayed. This feature can be implemented, for example, using intelligent image processing system 130E to supply the appropriate frames to system 140E so that the desired flicker rate is obtained. Alternatively, the laser light from combination light source 910 can be modulated to provide the flicker in the display. The flicker mode can be used in the other aspects described herein and so is not repeated for each one.

The above description of time division works for a first frame rate for the visible images, e.g., 30 frames per second, and a second frame rate for capture of fluorescence images. This description can be combined with the other aspects described above to provide time division in any of the aspects. Also, for time division multiplexing aspects, or in other image capture and processing aspects, filtering may be done to remove artifacts including motion artifacts and/or illumination artifacts if the endoscope or tissue is moved or the illumination changes.

Figure 9D:
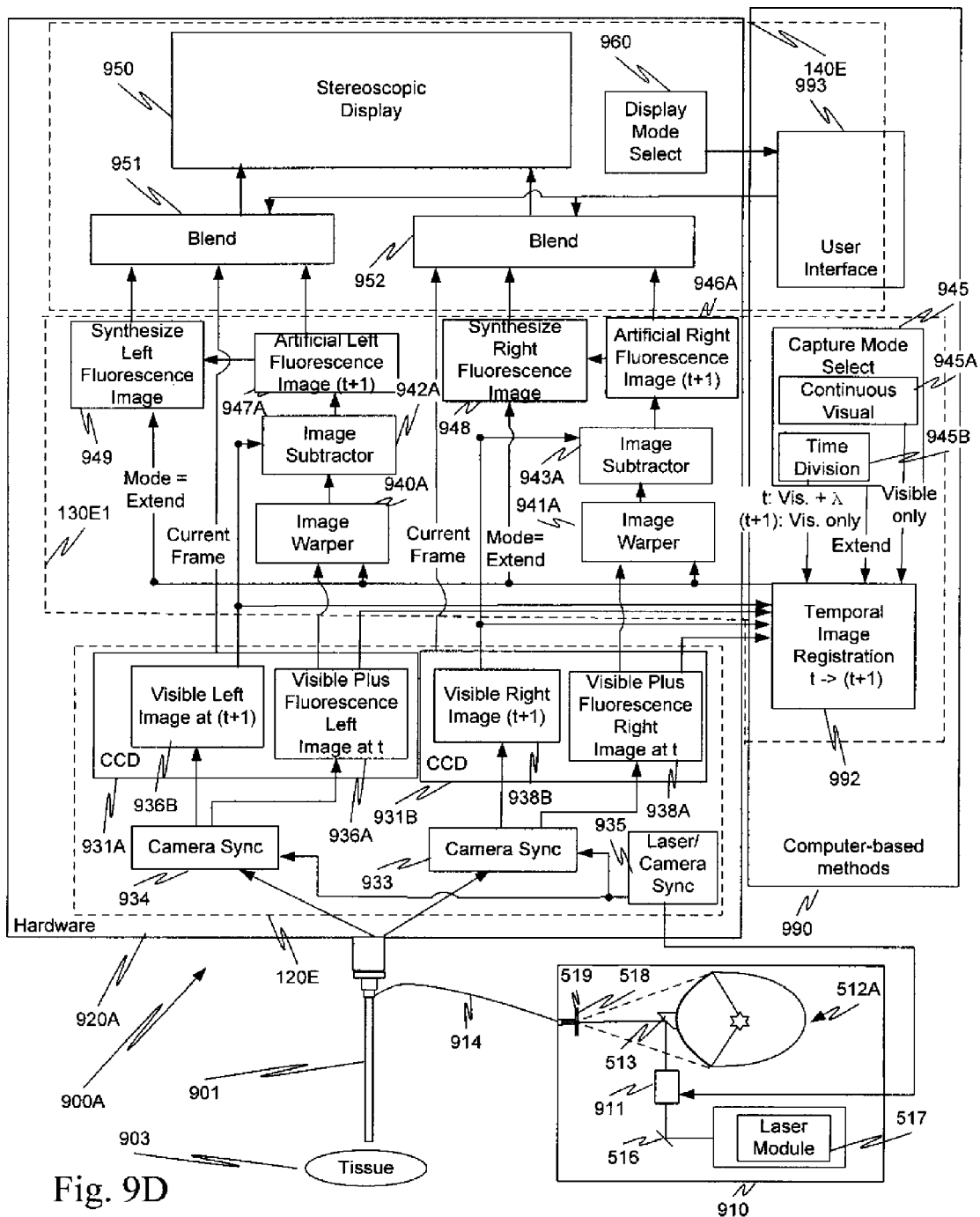
FIG. 9D is a schematic view that illustrates hardware and software (image processing and user interface) aspects of the use of time division with a single stereoscopic optical path for capturing, alternative processing, and outputting blended stereoscopic visible and fluorescence images in a minimally invasive surgical robotic system.

The aspects in FIGS. 9A and 9B are illustrative only and in view of the disclosure those knowledgeable in the field can implement a variety of configurations to achieve similar results. For example, FIG. 9D illustrates one alternative embodiment. In this example, system 900A includes hardware 920A that includes an alternative intelligent image processing system 130E. Here, Current Frame selects the appropriate stored frame to send to augmented stereoscopic display system 140E. For example, frames 936A and 936B are accessed as a stereoscopic pair and sent to system 140E. Next, frame 936B and artificial fluorescence left image 947A and frame 938B and artificial fluorescence right image 946A are provided to system 140E. The other elements in FIG. 9D work in the same way as described above for elements with the same reference numeral in FIGS. 9A and 9B.

Figure 9E:
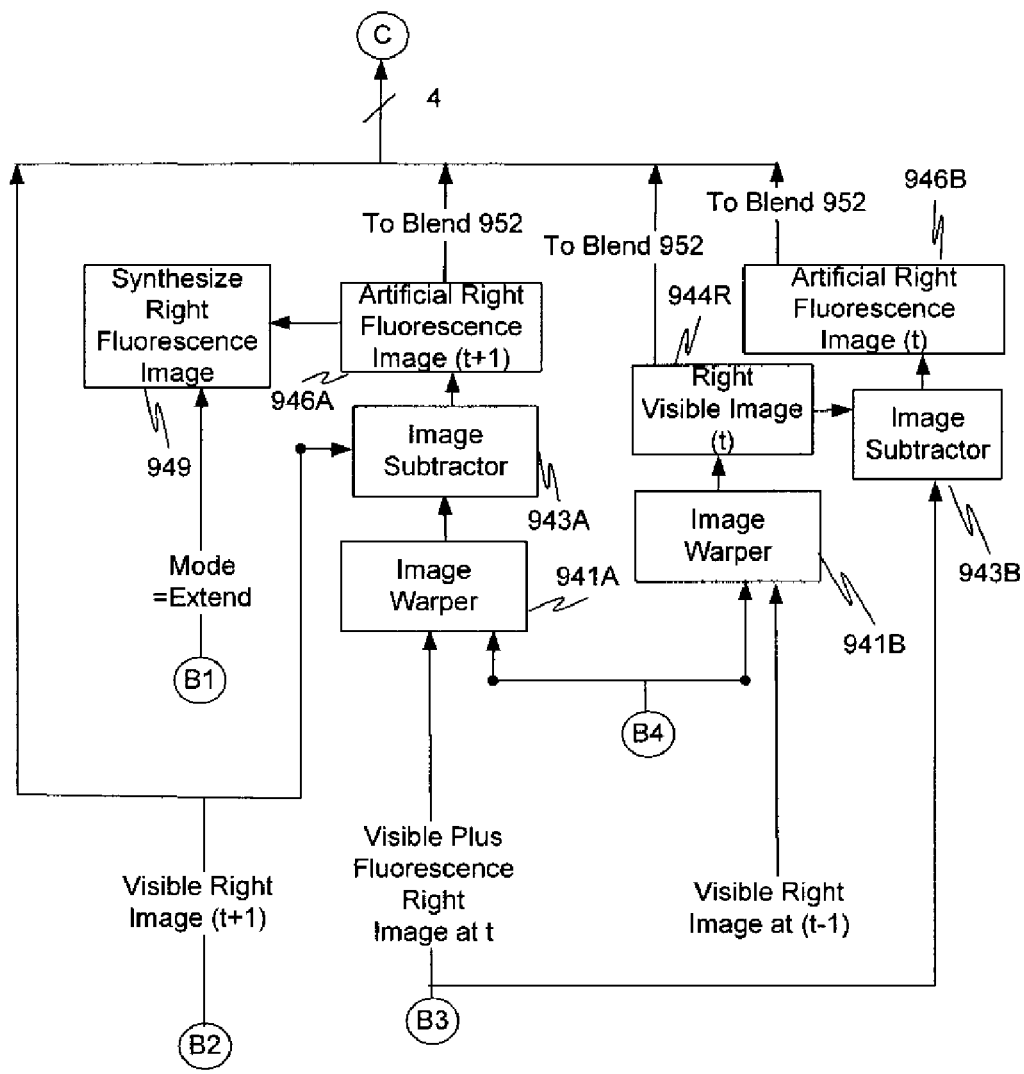
FIG. 9E is a schematic view that illustrates an alternative aspect of the intelligent image processing system.

FIG. 9E illustrates another aspect of intelligent image processing system 130E that could be incorporated for example in the system of FIGS. 9A and 9B. Here, only the processing of the images captured from the right optical channel in the stereoscopic optical path is shown. The hardware and processing for the images captures from the left optical channel is equivalent and so is not shown.

In this aspect, image warper 941B receives the visible right image captured at time (t−1) and the appropriate registration information. Image warper 941B generates visible right image 944R at time t. Image subtractor 943B receives as inputs visible right image 944R at time t and captured visible plus fluorescence right image 938A at time t. Image subtractor 943B subtracts visible right image 944R from captured visible plus fluorescence right image 938A to generate artificial fluorescence right image 946B at time t.

FIG. 10A is a process flow diagram for general time division multiplexing in which a combination visible fluorescence image frame is captured and then N, where N is an integer, visible only image frames are captured. For convenience, FIG. 10A is explained using the apparatus of FIG. 9A. FIG. 10A assumes that any initialization has been completed and process 1000 is in operation.

In capture visible and fluorescence images process 1001, image capture system 120E captures a stereoscopic pair of combined visible and fluorescence images 936A, 936B. Blended visible and fluorescence images are displayed on stereoscopic display 950 in stereoscopic display of images process 1002.

Initialize frame counter process 1003 initializes a frame counter to N (In the example described above N is one), and then in turn-off fluorescence excitation process 1004, laser/camera sync circuit 935 causes Pockels cell 911 to block the laser light beam.

Next, laser/camera sync circuit 935 causes visible images 938B, 938B to be captured in capture visible images process 1005. In registration process 1006, visible left image 936B is registered to captured combination left image 936A and right visible image 938B is registered to captured combination right image 938A.

Generate fluorescence left and right images process 1007 uses intelligent image processing system 130E to generate these images as described above with respect to FIGS. 9A and 9B. The visible and fluorescence images associated with the next frame in the time sequence for display are blended and displayed on stereoscopic display 950 in process 1008.

The frame counter is decremented in process 1009 and counter equal to zero check operation 1010 determines whether to capture another set of visible images or another set of combination visible and fluorescence images. If the frame counter is not equal to zero, processes 1005 to 1009 are repeated. If the frame counter is equal to zero, process 1011 turns on the fluorescence excitation source and transfers to process 1001.

Figure 10B:
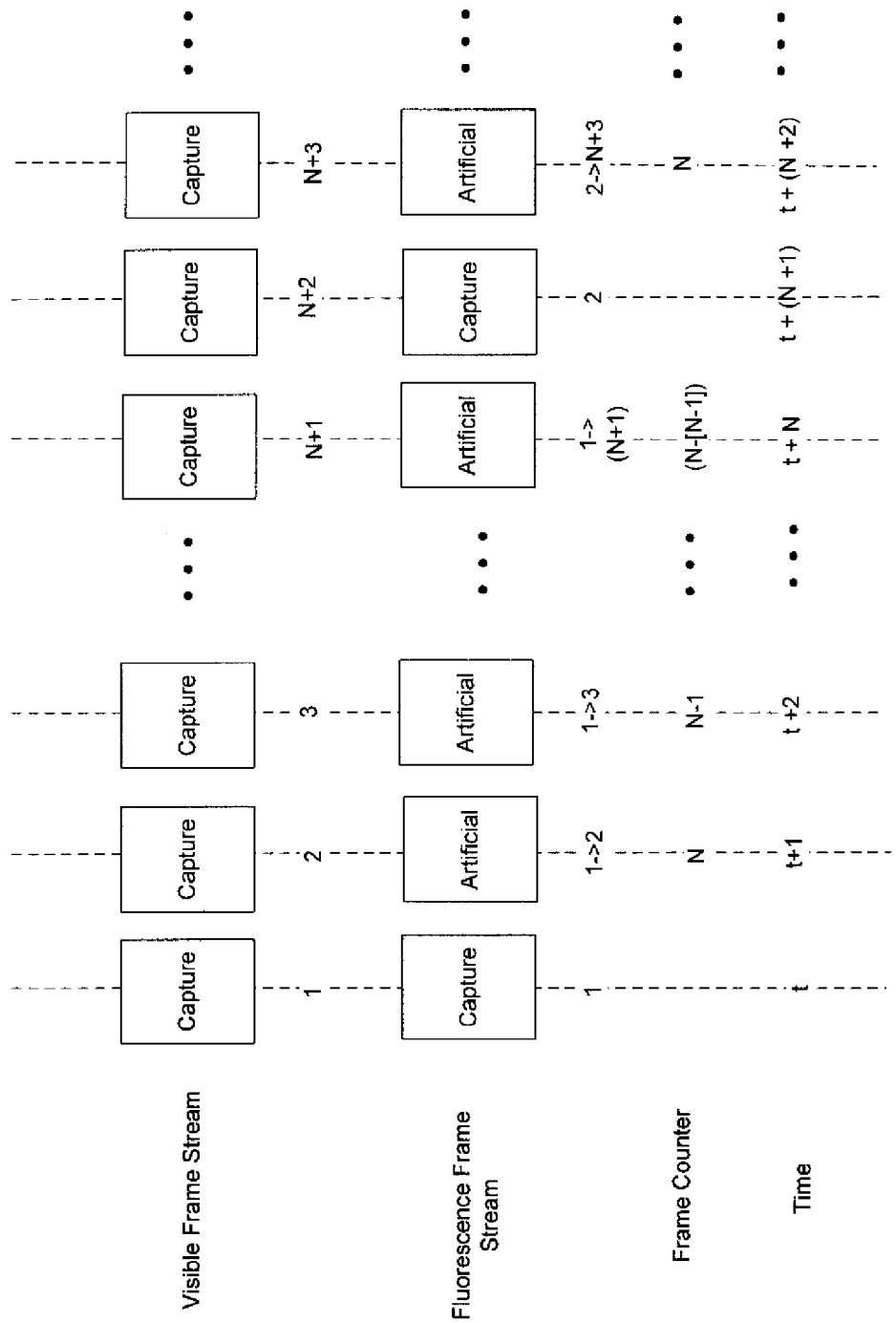
FIG. 10B illustrates aspects of the timing, synchronization, capture, and artificial fluorescence frames generated using the process of FIG. 10A.

FIG. 10B illustrates the visible and fluorescence frame streams in process 1000. As described above and shown in FIG. 10B, at time t, visible and fluorescence frames are captured.

From time (t+1) to time (t+N), only visible frames are captured. During this time interval, the fluorescence frame captured at time t is temporally registered to each captured visible frame and then the fluorescence frame captured at time t is warped to produce the artificial fluorescence frame for the corresponding time as shown in FIG. 10B. In one aspect, the captured and artificial fluorescence frames could be integrated and the integrated result displayed. Notice that the artificial fluorescence frames are used to synchronize the frame rate of the fluorescence image with the frame rate of the visible image in the stereoscopic display.

In more general terms, the fluorescence image may be artificially sustained in the video output to the surgeon between the frames that capture the fluorescence image. The artificially sustained fluorescence image is blended with the visible images as the camera switches between capturing visible and fluorescence images.

Also, as another example and as indicated above, the fluorescence image may be sustained after an injected agent no longer fluoresces so that the fluorescing region is still visible to the surgeon. In one aspect, the sustained image output is automatically stopped if the camera is moved so that the surgeon does not see a false blending of fluorescence and visible images. If the fluorescing region in the fluorescence image is spatially registered to the visible image, however, the sustained fluorescence image may be output because it is correctly blended with the visible image. As discussed above, artifacts may be filtered from the output display.

Time Division—Single Stereoscopic Optical Path with a Camera Unit that Captures Fluorescence Image Combined with a Visible Color Component In still another aspect, the visible and fluorescence images are captured via the same stereoscopic optical path, but image capture is time division multiplexed and the fluorescence image is captured with one of the visible color components, e.g., the red color component. In this aspect, the same camera unit captures data for both the visible and fluorescence images, but at different times. This time division is implemented by synchronizing a light source on/off with the video frame capture.

Figure 11A:
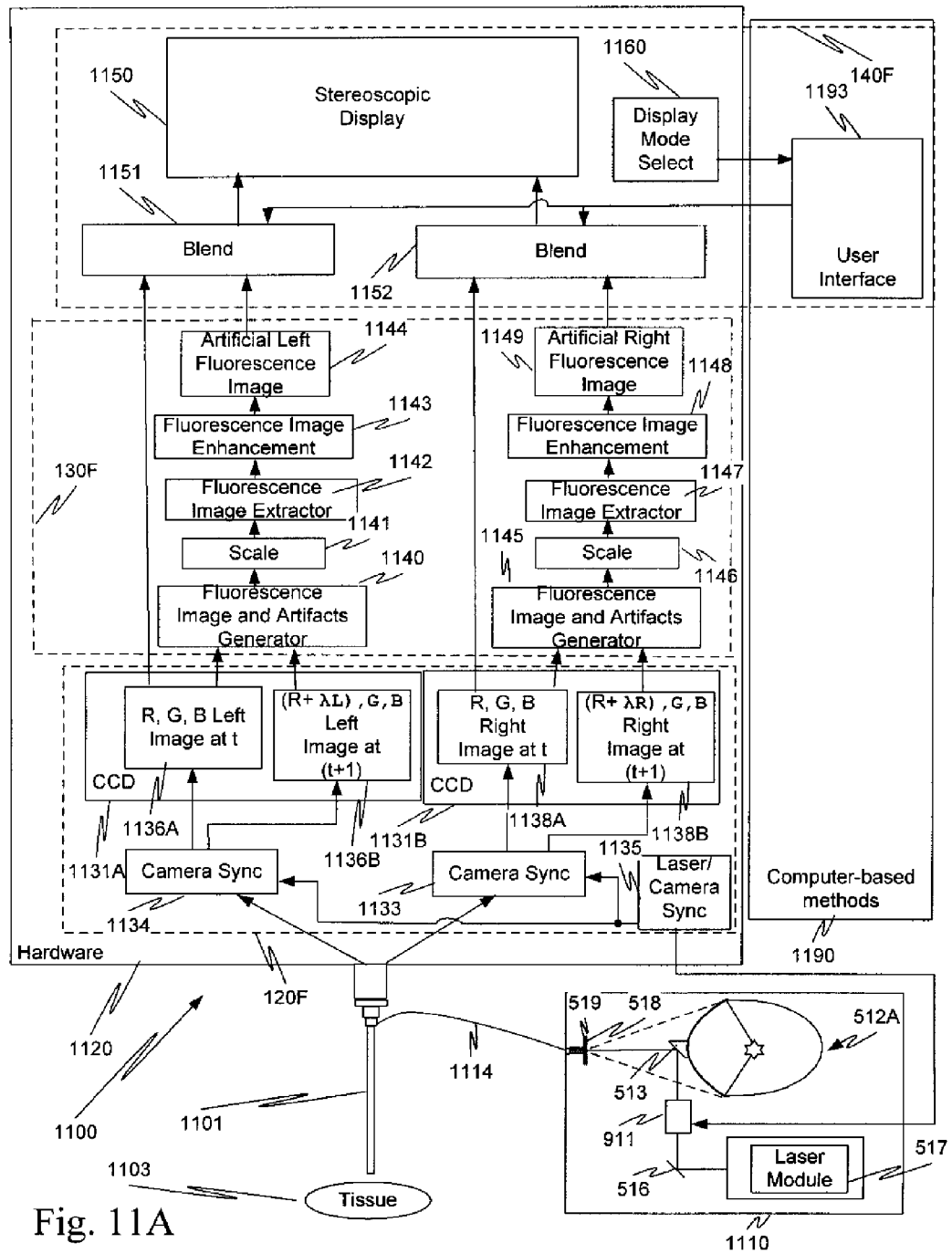
FIG. 11A is a schematic view that illustrates hardware and software aspects of the use of time division and capturing a fluorescence image with one of the visible color components using a single stereoscopic optical path, processing, and outputting blended stereoscopic visible and fluorescence images in a minimally invasive surgical robotic system.

For example, in the embodiment of FIG. 11A, a robotic surgical system (not shown) includes a single stereoscopic optical path for transporting light from tissue 1103 to augmented stereoscopic vision system 1100. Light from the single stereoscopic optical path is used to generate a real-time stereoscopic video display of tissue 1103 for the surgeon operating the robotic surgical system. The stereoscopic video display includes a three-dimensional view, sometimes called presentation, of tissue 1103 blended with an alternate image to highlight regions of interest in tissue 1103 such as diseased portions of tissue 1103 and/or other tissue of interest, such as a nerve or organ.

In this example, a single endoscope 1101 provides the stereoscopic optical path from tissue 1103 to hardware 1120. Endoscope 1101 has two light channels making up the stereoscopic optical path and at least one illumination channel for providing light to tissue 1103. While it is not shown, endoscope 1101 is held and moved by the robotic surgical system. See FIG. 1 for example.

In this example, augmented stereoscopic vision system 1100 includes a combination light source 1110, hardware 1120, and at least one computer-based method 1190. As shown in FIG. 11A, a portion of hardware 1120 makes up image capture system 120F. Another portion of hardware 1120 makes up intelligent image processing system 130F. Yet another portion of hardware 1120 and a computer based method make up augmented stereoscopic display system 140F. Within image capture system 120F and intelligent image processing system 130F, the portions that process visible images make up a visible imaging system while the portions that process fluorescence images make up an alternate imaging system.

Figure 12:
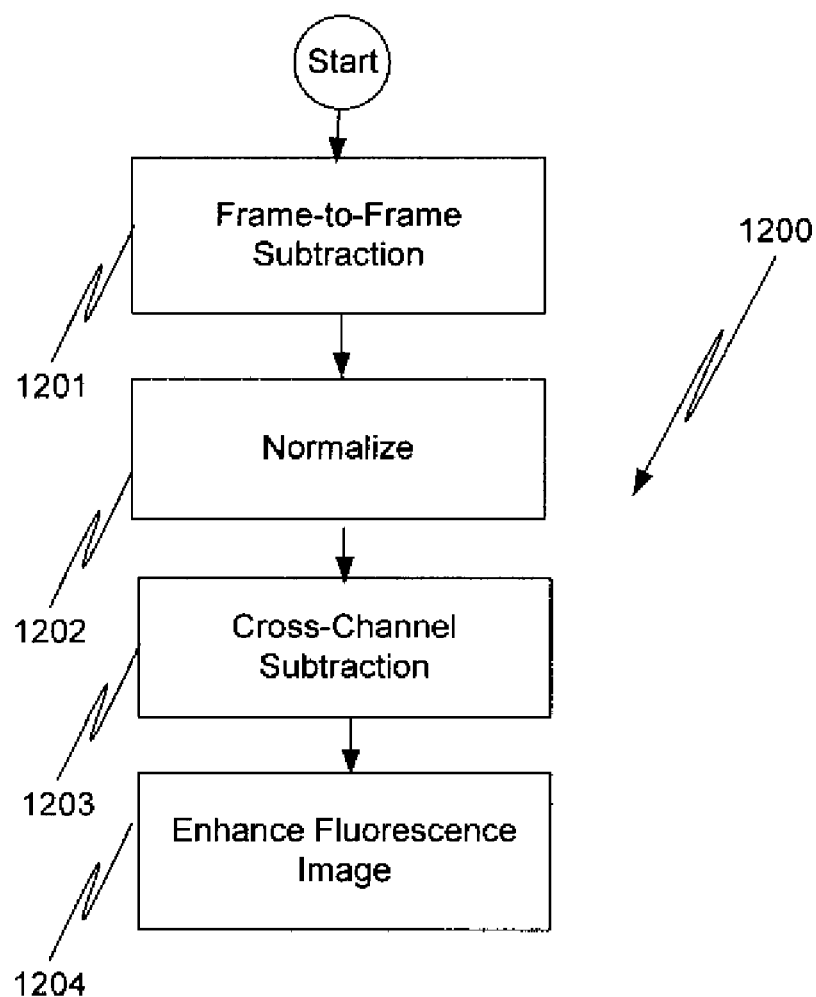
FIG. 12 is a process flow diagram for one aspect of the intelligent image processing system of FIG. 11A.

Also, method 1200 of FIG. 12 is implemented using augmented stereoscopic vision system 1100. As shown in FIG. 12, method 1200 includes a plurality of separate processes.

In one aspect, hardware 1120 includes a single camera unit such as camera unit 731 (FIG. 7B). Camera unit 731 includes a 3-chip charge-coupled device (CCD) sensor for each optical path of endoscope 1101.

Hardware 1120 also includes hardware circuits for performing the functions described more completely below. At least one computer-based method 1190 is, for example, software executing on a computer processor.

Time Division—Single Stereoscopic Optical Path with a Camera Unit that Captures Fluorescence Image Combined with a Visible Color Component—Illumination Combination light source 1110 with fiber optic bundle 1114 is similar to any one of combination light sources 510A (FIG. 5C), 510B (FIG. 5D) and 520C (FIG. 5E) and the associated fiber optic bundles, as well as the various aspects described above with respect to the implementation of combination light source 310A (FIG. 3C) Accordingly, the description of those combination light sources is incorporated herein by reference. However, combination light source 1110 includes a means for turning off and on at least one of the light sources and so light source 910 is used, as and example, and the above description of light source 910A is incorporated herein by reference.

In one aspect, at a time t, Pockels cell 911 receives a signal from laser/camera sync circuit 1135 so that the laser beam is blocked by Pockels cell 911 and only the light from white light source 512A is injected into fiber optic cable 1114. At a time (t+1), Pockels cell 911 receives a signal from laser/camera sync circuit 1135 so that the laser beam passes through Pockels cell 911 and is injected into fiber optic cable 1114 with the light from white light source 512A. Here, time t is associated with a frame, while time (t+1) is associated with a different frame.

Thus, for a first time interval, tissue 1103 is illuminated with only the white light and then for a second time interval immediately following the first time interval, tissue 1103 is illuminated with white light and with light that simulates fluorescence from tissue 1103. In this example, the laser beam is modulated on and off. However, in view of the following description, system 1100 could be implemented with the white light source modulated on and off and with the laser beam maintained continuously on.

Figure 11B:
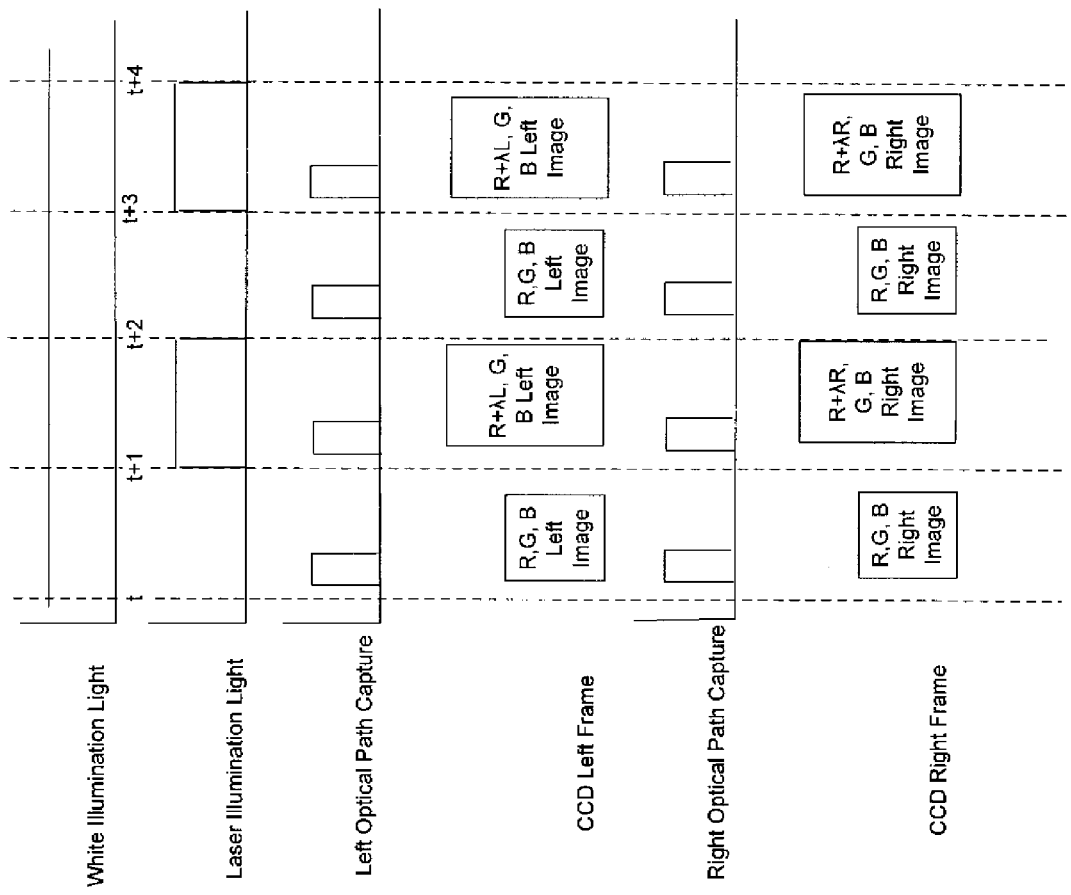
FIG. 11B illustrates one aspect of the timing, synchronization, and capture of the system in FIG. 11A.

Time Division—Single Stereoscopic Optical Path with a Camera Unit that Captures Fluorescence Image Combined with a Visible Color Component—Image Capture System 120F Laser/camera sync circuit 1135 also provides a signal to camera sync 1134 and 1133. In response to that signal, camera sync 1134 causes a frame to be captured in left CCD sensor 1131A and camera sync 1133 causes a frame to be captured in right CCD sensor 1131B. Each CCD sensor is a 3-chip CCD sensor. FIG. 11B is an example of the synchronization between combination light source 1110 and the frame capture.

For example, at time t, tissue 1103 is illuminated with the white light and a signal Left Optical Path Capture, Right Optical Path Capture is sent to camera sync 1134 and 1133, respectively. Thus, at time t, a first stereoscopic frame 1136A of visible red, green and blue components of a visible left image is captured in left CCD 1131A. Also, at time t, a first stereoscopic frame 1138A of visible red, green and blue components of a visible right image is captured in right CCD 1131B.

For example, at time (t+1), tissue 1103 is illuminated with both the white light and the laser light, and a signal Left Optical Path Capture, Right Optical Path Capture is sent to camera sync 1134 and 1133, respectively. Thus, at time (t+1), a second stereoscopic frame 1136B of visible red, green and blue components of a visible left image is captured in left CCD 1131A. However, the visible red component is combined with the fluorescence left image λL so that the combined image is captured in left CCD 1131A. Also, at time (t+1), a second stereoscopic frame 1138A of visible red, green and blue components of a visible right image is captured in right CCD 1131B. However, the visible red component is combined with the fluorescence right image λR so that the combined image is captured in right CCD 1131B. This capture rate is illustrative only and in view of this disclosure an appropriate capture rate for the fluorescence image can be chosen.

The left images from tissue 1103 (FIG. 11A) are captured from a left optical channel of the stereoscopic optical path in endoscope 1101, and the right images from tissue 1103 are captured from a right optical channel of the stereoscopic optical path in endoscope 1101.

In the example of FIG. 11A, two frames are shown as being captured by the CCD sensor. This is for ease of illustration only and is not intended to be limiting. As is known, prior to capture of the frame at time (t+1), the frame captured in the CCD sensor could be moved to a buffer, for example, for the processing described more completely below.

Time Division—Single Stereoscopic Optical Path with a Camera Unit that Captures Fluorescence Image Combined with a Visible Color Component—Intelligent Image Processing System 130E Since the fluorescence image is captured with one of visible color components, it necessary to extract the fluorescence image so that the fluorescence image can be processed to highlight the fluorescence tissue in the stereoscopic visual display. The processing of the left and right images is similar and so in the following description only the left channel is considered.

Herein, the red, green and blue visible components captured at time t are represented by $R_t$, $G_t$, and $B_t$, respectively. The component captured at time (t+1) are represented by $(R+\lambda)_{t+1}$, $G_{t+1}$ and $B_{t+1}$.

Fluorescence image and artifacts generator 1140 (FIG. 11A), in one aspect, uses a frame-to-frame subtraction process 1201 of process 1200 (FIG. 12) to generate a fluorescence image with possible artifacts introduced by illumination changes as well as motion artifacts. Frame-to-frame subtraction process 1201 subtracts the frame captured at time t from the frame captured at time (t+1). For example, $$I_R = (R+\lambda)_{t+1} - R_t$$

$$I_G = G_{t+1} - G_t$$

$$I_B = B_{t+1} - B_t$$

where $I_R$, $I_R$, and $I_R$ are frame-to-frame color component differences for the red, green and blue color components, respectively. More specifically, frame-to-frame red color component difference $I_R$ is the fluorescence image combined with possible artifacts of the red color component; and frame-to-frame green color component difference $I_G$ and frame-to-frame blue color component difference $I_B$ are the possible artifacts of the green and blue color components, respectively. The phrase "possible artifacts" is used because tissue 1103, endoscope 1101 and instruments may not move between the two frames and the lighting may be stable in such a case there would be no artifacts.

To separate artifacts from the fluorescence image, scale system 1141 (FIG. 11A), in one aspect, implements normalize process 1202 (FIG. 12). Scale system 1141 is optional and is not used in all aspects. However, in this aspect, normalize process 1202 processes frame-to-frame color component differences $I_R$, $I_G$, and $I_B$ so that the differences have a common scale. For example, in one aspect, the mean for each color component difference is subtracted from the color component difference and the result is scaled to a unit variance. For example, $$\hat{I}_R = \frac{I_R - \bar{I}_R}{\sigma^2_{I_R}}$$

$$\hat{I}_G = \frac{I_G - \bar{I}_G}{\sigma^2_{I_G}}$$

$$\hat{I}_B = \frac{I_B - \bar{I}_B}{\sigma^2_{I_B}}$$

where $I_R$, $I_G$ and $I_B$ and $\bar{I}_R$, $\bar{I}_G$ and $\bar{I}_B$, respectively, are the same elements. A bar over the color component difference represents the mean for that color components and a square of σ represents the variance. The determination of the mean and variance could be based on the whole frame or alternatively a smaller region of the frame.

If there was motion or an illumination change between the times of the capture of the two frames, the artifacts in the three color components between the two frames are usually similar, but may not be exactly identical. Thus, the artifacts of the normalized green and blue color components between the two frames can be used to approximate the artifacts in the normalized red component. Thus, in one aspect, the normalized blue and green components are used to ameliorate the effects of artifacts between the two frames in the fluorescence image.

Thus, fluorescence image extractor 1142 (FIG. 11A), in one aspect implements cross-channel subtraction process 1203 (FIG. 12). Cross-channel subtraction process 1203 subtracts the normalized blue and green frame-to-frame color component differences from the normalized frame-to-frame red color component that includes fluorescence image λ to obtain the fluorescence image F. Specifically, in one aspect, cross-channel subtraction process 1203 generates fluorescence image F as:

$$F = |\hat{I}_R - \hat{I}_B| + |\hat{I}_R - \hat{I}_G|$$

Fluorescence image enhancement 1143 (FIG. 11A), in one aspect, implements enhance fluorescence image process 1204 (FIG. 12). Enhance fluorescence image process 1204 optionally scales fluorescence image F and changes the color from red to either green or blue, e.g., false colors fluorescence image F so that when fluorescence left image 1144 is blended with a visible image, the fluorescence image stands out. Artificial fluorescence left image 1144 and artificial fluorescence right image 1149 are a stereoscopic pair of fluorescence images.

In one aspect, optional sparse tissue tracking is included. For example, temporal registration for pixels declared as motion regions is used to determine whether there truly was motion in each of the motion regions. In addition, image filtering and thresholding can be used to clean up the final fluorescence image.

The above aspects of process 1200 are illustrative only and are not intended to be limiting. Various variants of these processes can be implemented in the hardware. For example, Frame-Frame Subtraction $$I_{t+1} - I_t = \{R_{t+1} - R_t + \lambda_{t+1},\ G_{t+1} - G_t,\ B_{t+1} - B_t\}$$

Detect the Motion/Illumination Change Regions (MIR)

MIR: if $(G_{t+1} - G_t) + (B_{t+1} - B_t) >$ threshold_1

Determine Fluorescence Region (FR) After Post Processing if

FR: if NOT MIR & $abs((R_{t+1} - R_t) + \lambda_{t+1} - (G_{t+1} - G_t)) >$ threshold_2

In one aspect the thresholds are empirically determined.

Elements 1145 to 1149 function in a matter to that just described for the left channel and also implement process 1200. Accordingly, the implementation of elements 1145 to 1149 follows directly from the above description.

This processing continues for each pair of captured frames. Various alternatives can be used to generate artificial images to provide the frame rate needed for display of the visible and fluorescence images. For example, the images can simply be repeated. Alternatively, once multiple frames have been processed interpolation could be used to generate artificial frames for the fluorescence image and/or visible image as needed.

Time Division—Single Stereoscopic Optical Path with a Camera Unit that Captures Fluorescence Image Combined with a Visible Color Component—Augmented Stereoscopic Display System 140F In one aspect, the augmented stereoscopic video output display may be operated in various modes. For example, in a first mode, only stereoscopic visible images are output to the surgeon, as in the da Vinci® Surgical System. In a second mode, a fluorescence image is superimposed on the visible images to create an augmented image, and the stereoscopic augmented image is output to the surgeon.

The video output may be toggled between these modes by using, e.g., a foot switch, a double click of the master grips that control the surgical instruments, voice control, and other like switching methods. The toggle for switching between the two modes is represented in FIG. 11A as display mode select 1160 which generates a signal that is provided to blend circuits 1151, 1152, which function in the same way as previously described for the other blend circuits.

The techniques previously described for enhancing the fluorescence image in the stereoscopic display are also applicable to this embodiment.

Single Stereoscopic Optical Path with a Modified Camera Unit

In still another aspect, the visible and fluorescence images are captured via the same stereoscopic optical path, but the fluorescence image is again captured with one of the visible color components. In this aspect, the same camera unit captures data for both the visible and fluorescence stereoscopic images but a prism, as explained more completely below, combines the fluorescence image with one of the visible color components.

Figure 13A:
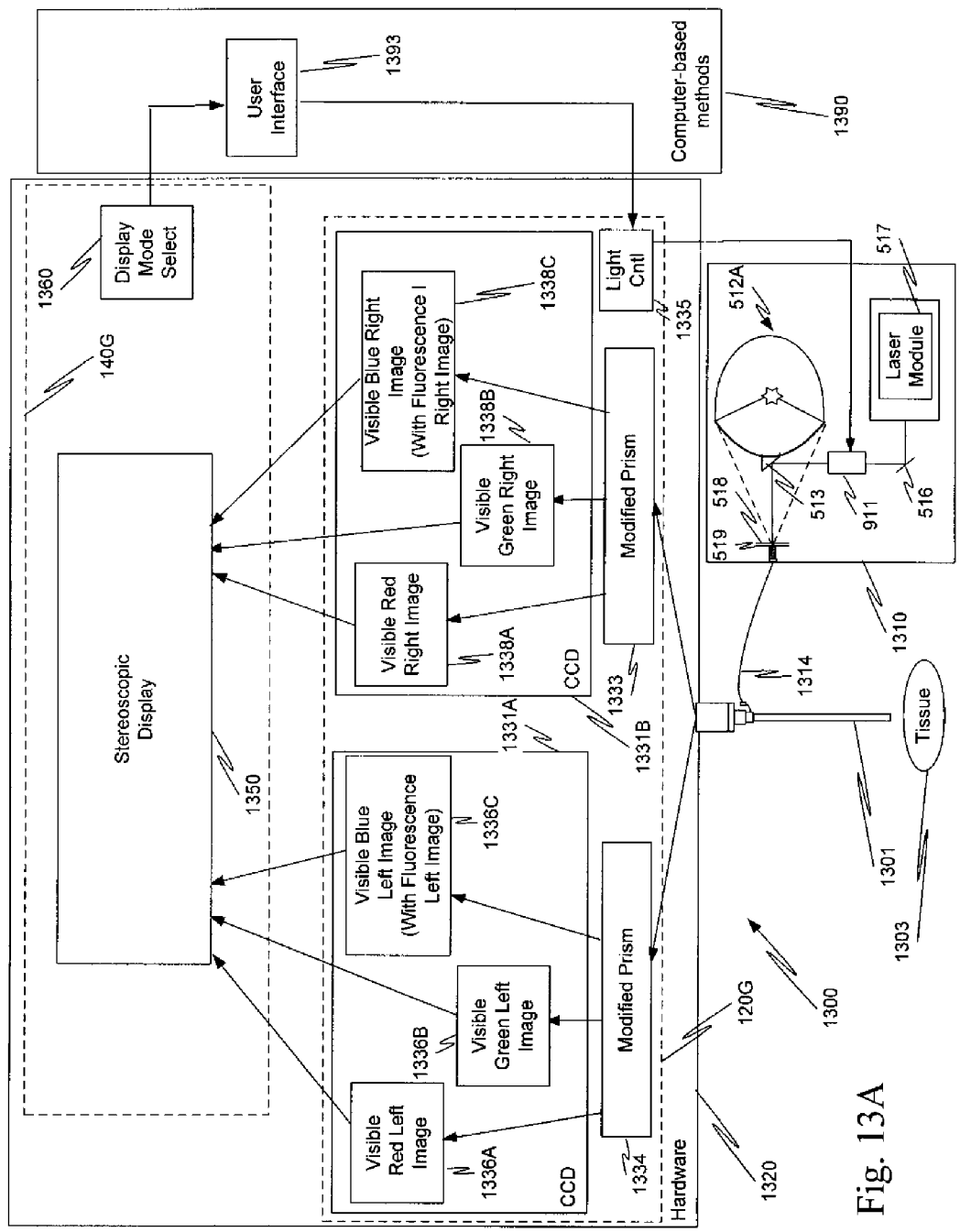
FIG. 13A is a schematic view that illustrates hardware and software (image processing and user interface) aspects of using a single stereoscopic optical path, capturing with a camera unit having modified prisms, processing, and outputting real-time stereoscopic visible and fluorescence images in a minimally invasive surgical robotic system.

For example, in the embodiment of FIG. 13A, a robotic surgical system (not shown) includes a single stereoscopic optical path for transporting light from tissue 1303 to augmented stereoscopic vision system 1300. Light from the single stereoscopic optical path is used to generate a real-time stereoscopic video display of tissue 1303 for the surgeon operating the robotic surgical system. The stereoscopic video display includes a three-dimensional view of tissue 1303 with an alternate image to highlight regions of interest in tissue 1303 such as diseased portions of tissue 1303 and/or other tissue of interest, such as a nerve or organ.

In this example, a single endoscope 1301 provides the stereoscopic optical path from tissue 1303 to hardware 1320. Endoscope 1301 has two light channels making up the stereoscopic optical path and at least one illumination channel for providing light to tissue 1303. While it is not shown, endoscope 1301 is held and moved by the robotic surgical system. See FIG. 1 for example.

In this example, augmented stereoscopic vision system 1300 includes combination light source 1310, hardware 1320, and at least one computer-based method 1390. As shown in FIG. 13A, a portion of hardware 1320 makes up image capture system 120G. In this aspect, an intelligent image processing system is not used. Yet another portion of hardware 1320 and at least one computer-based method 1393 make up augmented stereoscopic display system 140G. Within image capture system 120G, the portions that process visible images make up a visible imaging system while the portions that process fluorescence images make up an alternate imaging system.

In one aspect, hardware 1320 includes a single camera unit such as a modified camera unit 731 (FIG. 7B). Camera unit 731 includes a 3-chip charge-coupled device (CCD) sensor for each optical path of endoscope 1301.

Hardware 1320 also includes hardware circuits for performing the functions described more completely below. Computer-based methods 1390 are, for example, software executing on a computer processor.

Single Stereoscopic Optical Path with a Modified Camera Unit—Illumination

Combination light source 1310 with fiber optic bundle 1314 is similar to combination light source 910 and fiber optic bundle 914. Accordingly, the description of that combination light source is incorporated herein by reference. However, in combination light source 1310 the control of a means for turning off and on at least one of the light sources is different from that in combination light source 910.

In this aspect, Pockels cell 911 receives a control signal from light controller 1335 that in turn receives a signal from user interface 1393. When the surgeon selects visible only, a signal is applied to Pockels cell 911 so that the laser beam is blocked by Pockels cell 911 and only the light from white light source 512A is injected into fiber optic cable 1314. When the surgeon selects visible plus fluorescence, both light sources provide a beam that is injected into fiber optic cable 1314.

Figure 13B:
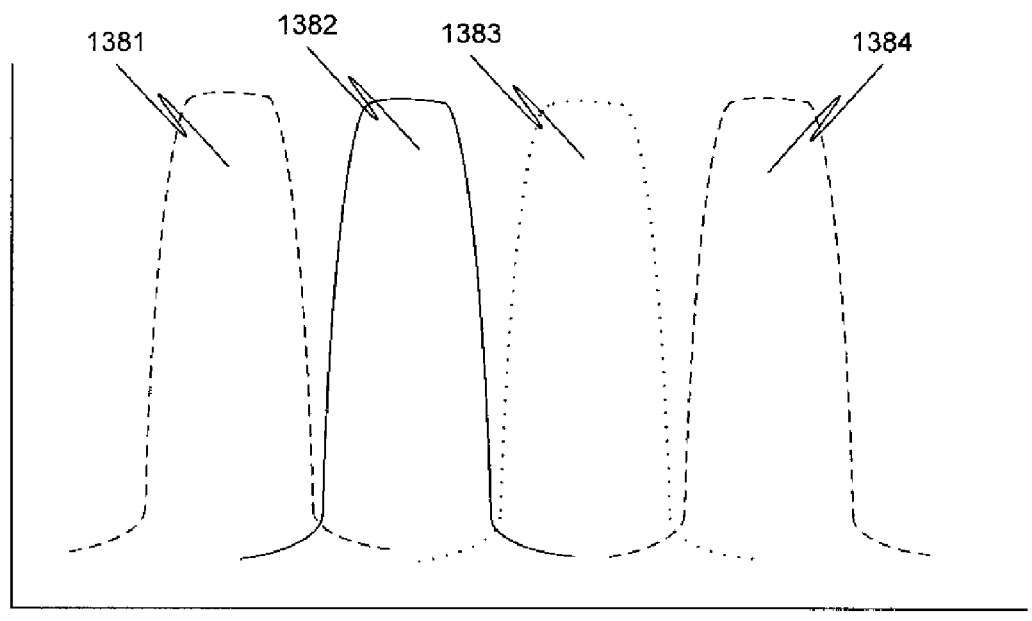
FIG. 13B illustrates a spectrum from a prism that separates visible and fluorescence light from tissue into a first color component of the visible image, a second color component of the visible image, a third color component of the visible image, and a fourth component separated and removed from the first, second, and third color components with the fourth component having a color of one the color components.

Single Stereoscopic Optical Path with a Modified Camera Unit—Image Capture System 120G In this aspect, the camera unit is modified so that the light from each optical path is passed through a modified prism 1334, 1333. Each of modified prisms 1334, 1333, for example, has the characteristics shown in FIG. 13B.

Modified prisms 1334, 1333 split the visible plus fluorescence images from the optical paths into typical RGB components 1381, 1382, 1383 (Note the color of the component is represented by the characteristic of the line-blue by a dashed line; green by a solid line; and red by a dotted line.) However, in this example, modified prisms 1334, 1333 generate not only a blue color component 1381 but also a second blue peak 1384 that is in near infrared region. Thus, when the fluorescence image is in the near infrared, this prism separates the combined visible and fluorescence images into a visible RGB image and a blue fluorescence image in the near infrared. Modified prism 1334, 1333 are made in a conventional fashion, except a portion of the prism that normally passes only one visible color component is modified to pass both that visible color component and another component that is separated and removed from the color component. The another component corresponds to a fluorescence image.

While in this aspect, dual peaks are provided with respect to the blue component, depending upon the fluorescence wavelength, the prism can be modified to obtain the desired results for any of the color components. In this aspect, the CCD for the blue color component accumulates both peak 1481 and peak 1484 and so captures the visible blue image from the optical path combined with the fluorescence image from that optical path.

Thus, as illustrated in FIG. 13A, when both the beam from light source 512A and the beam from light source 517 illuminate tissue 1303, a red left CCD in left CCD 1331A captures a visible red left image 1336A; a green left CCD in left CCD 1331A captures a visible green left image 1336B; and a blue left CCD in left CCD 1331A captures a visible blue left image combined with a fluorescence left image 1336C. Similarly, a red right CCD in left CCD 1331B captures a visible red right image 1338A; a green right CCD in right CCD 1331B captures a visible green right image 1338B; and a blue right CCD in right CCD 1331B captures a visible blue right image combined with a fluorescence right image 1338C.

When the laser beam is not injected in fiber optic bundle 1314 and only light from light source 512A is injected, the red left CCD in left CCD 1331A captures a visible red left image 1336A; the green left CCD in left CCD 1331A captures a visible green left image 1336B; and the blue left CCD in left CCD 1331A captures only a visible blue left image 1336C. This is why "With Fluorescence Left Image" is enclosed in parentheses in FIG. 13A, because the fluorescence left image is not always captured. Similarly, the red right red CCD in right CCD 1331B captures a visible red right image 1338A; the green right CCD in right CCD 1331B captures a visible green right image 1338B; and the blue right CCD in right CCD 1331B captures only a visible blue right image 1338C. This is why "With Fluorescence Right Image" also is enclosed in parentheses in FIG. 13A, because the fluorescence right image is not always captured.

Single Stereoscopic Optical Path with a Modified Camera Unit—Augmented Stereoscopic Display System 140G In one aspect, the augmented stereoscopic video output display may be operated in various modes. For example, in a first mode, only real-time stereoscopic visible images are output to the surgeon, as in the da Vinci® Surgical System. In a second mode, a fluorescence image is superimposed on the visible image to create an augmented image, and the real-time stereoscopic augmented image is output to the surgeon.

As indicated above, the video output may be toggled between these modes by using, e.g., a foot switch, a double click of the master grips that control the surgical instruments, voice control, and other like switching methods. The toggle for switching between the two modes is represented in FIG. 13A as display mode select 1360 which generates a signal that is provided to user interface 1393 that in turn provides a control signal to light controller 1335 as previously described.

The techniques previously described for enhancing the fluorescence image in the stereoscopic display are also applicable to this embodiment. When such techniques are used an intelligent image processing system would be included in system 1300.

In addition, in some aspects, another display mode that generates an augmented display with fluorescence and visible images may be implemented. This display mode can be a variation of the first display mode or a completely different display mode. In either case, the fluorescence image flickers on and off in the stereoscopic display and so is not continuously displayed. This feature can be implemented, for example, using an intelligent image processing system to supply the appropriate frames to system 140G so that the desired flicker rate is obtained. Alternatively, the laser light from combination light source 1310 can be modulated to provide the flicker in the display.

Figure 14:
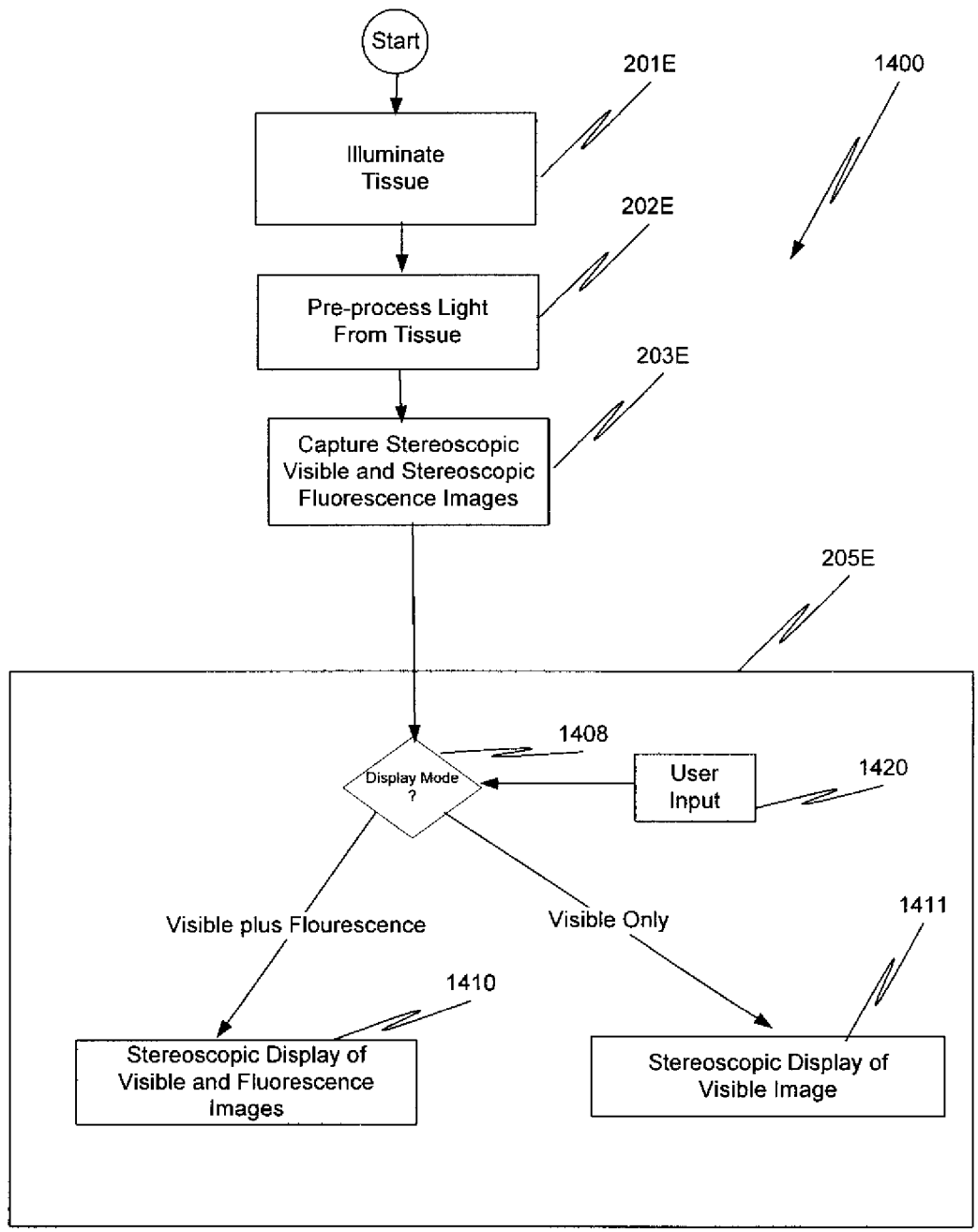
FIG. 14 is process flow diagram of a process performed using, for example, the augmented stereoscopic visualization system for a minimally invasive surgical robot of FIG. 13A.

In one aspect, method 1400 (FIG. 14) is implemented using augmented stereoscopic vision system 1300. In illuminate tissue process 201E, light from combination light source 1310 illuminates tissue 1303.

Light from tissue 1303 is split into the various components, as described above, in pre-process light from tissue process 202E. The various components including the components combined with the fluorescence images are captured in capture stereoscopic visible and stereoscopic fluorescence images process 203E.

Based upon the user input to user input process 1420, a display mode check operation 1408 in user interface 1393 configures combination light source, if necessary, and performs one of stereoscopic display of visible and fluorescence images process 1410 and stereoscopic display of visible image only process 1411. Process 1410 and 1411, in generate stereoscopic video display of tissue process 205E, generate the displays that were described above with respect to augmented stereoscopic vision system 1300.

Time-Division—Singe Stereoscopic Optical Path with a Single CCD Camera Unit

In still another aspect, the visible and fluorescence images are captured via the same stereoscopic optical path, but image capture is time division multiplexed. In this aspect, the same camera unit captures data for both the color components of the visible image and the fluorescence image, but at different times. This time division is implemented by synchronizing capture with filtering using a rotating filter, as described more completely below.

Figure 15:
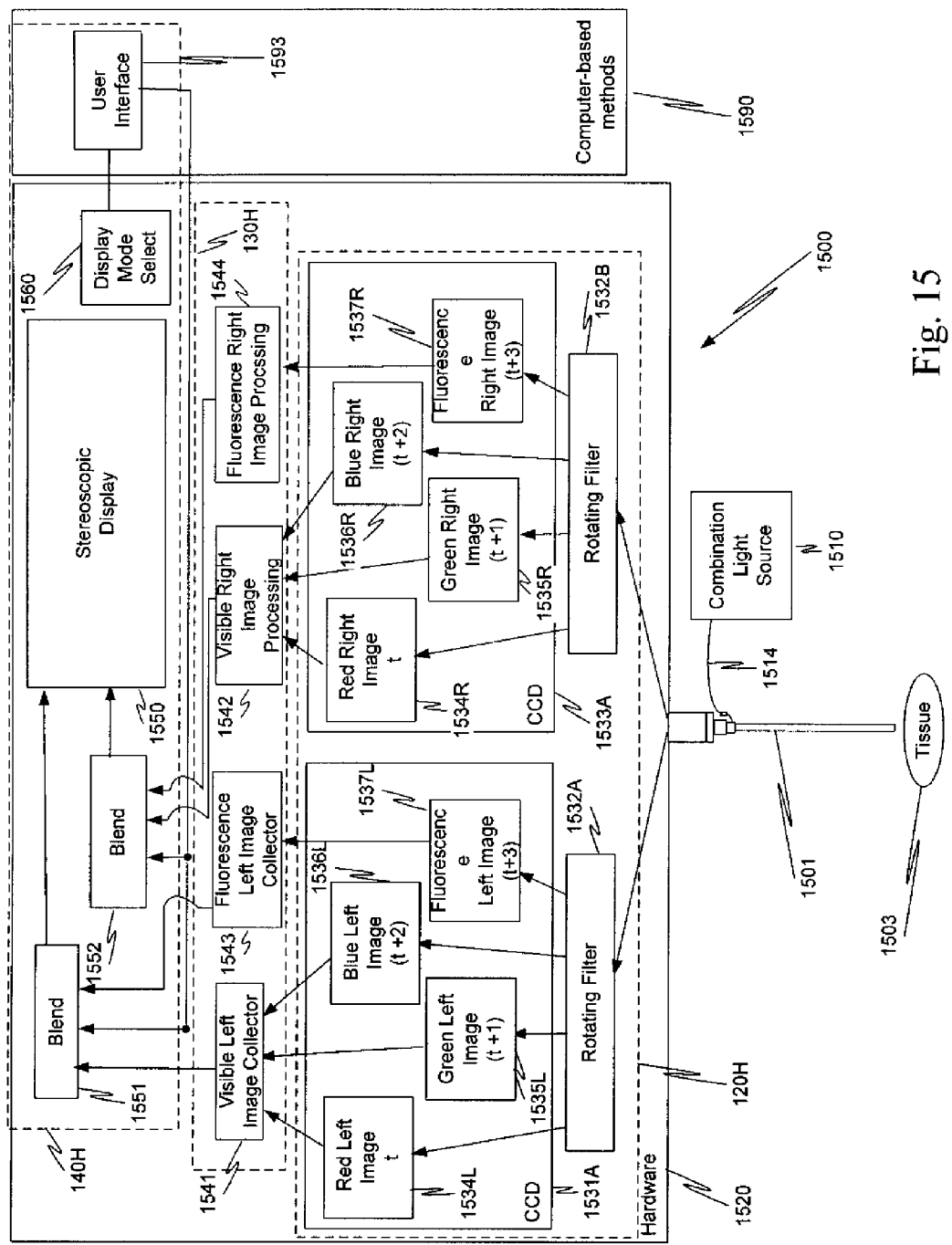
FIG. 15 illustrates one aspect of the timing, synchronization, and capture for the time and channel division in an augmented stereoscopic visualization system for a minimally invasive surgical robot utilizing a stereoscopic endoscope with 1-chip CCD sensor.

For example, in the embodiment of FIG. 15, a robotic surgical system (not shown) includes a single stereoscopic optical path for transporting light from tissue 1503 to augmented stereoscopic vision system 1500. Light from the single stereoscopic optical path is used to generate a real-time stereoscopic video display of tissue 1503 for the surgeon operating the robotic surgical system. The stereoscopic video display includes a three-dimensional view of tissue 1503 blended with an alternate image to highlight regions of interest in tissue 1503 such as diseased portions of tissue 1503 and/or other tissue of interest, such as a nerve or organ.

In this example, augmented stereoscopic vision system 1500 includes combination light source 1510, hardware 1520, and at least one computer-based method 1590. As shown in FIG. 15, a portion of hardware 1520 makes up image capture system 120H. Another portion of hardware 1520 makes up intelligent image processing system 130H. Yet another portion of hardware 1520 and a user interface 1593 in computer-based methods 1590 make up augmented stereoscopic display system 140H. Within image capture system 120H and intelligent image processing system 130H, the portions that process visible images make up a visible imaging system while the portions that process fluorescence images make up an alternate imaging system.

In one aspect, hardware 1520 includes a single camera unit such as a modified camera unit 731 (FIG. 7B). Camera unit 731 includes a single coupled device (CCD) sensor for each optical path of endoscope 1501.

Hardware 1520 also includes hardware circuits for performing the functions described more completely below. Computer-based methods 1590 are, for example, software executing on a computer processor.

Time-Division—Singe Stereoscopic Optical Path with a Single CCD Camera Unit—Illumination Combination light source 1510 with fiber optic bundle 1514 is similar to any one of combination light sources 510A (FIG. 5C), 510B (FIG. 5D) and 510C (FIG. 5E) and the associated fiber optic bundles, as well as the various aspects described above with respect to the implementation of combination light source 310A (FIG. 3C). Accordingly, the description of those combination light sources is incorporated herein by reference.

Time-Division—Single Stereoscopic Optical Path with a Single CCD Camera Unit—Image Capture System 120G In this aspect, tissue 1503 is illuminated with both the white light and the laser light from combination light source 1510. The capture operations for the left and right images are equivalent.

Rotating filter 1532A includes four band pass filters: a visible red filter, a visible green filter, a visible blue filter and a fluorescence filter. Rotating filter 1532B is similarly configured. Rotating filters 1532A, 1532B are coupled with the capture of an image in the single CCD of the camera unit, e.g. left CCD 1531A for the filtered light from the left optical path of endoscope 1501 and right CCD 1533A for filtered light from the right optical path of endoscopic 1501.

At time t, rotating filter 1532A filters light from the left optical path of endoscope 1501 with the red filter and so left CCD 1531A captures red left image 1534L at time t. At time t+1, rotating filter 1532A filters light from the left optical path of endoscope 1501 with the green filter and so left CCD 1531A captures green left image 1535L at time t+1. At time t+2, rotating filter 1532A filters light from the left optical path of endoscope 1501 with the blue filter and so left CCD 1531A captures blue left image 1536L at time t+2. At time t+3, rotating filter 1532A filters light from the left optical path of endoscope 1501 with the fluorescence filter and so left CCD 1531A captures fluorescence left image 1537L at time t+3.

At time t, rotating filter 1532B filters light from the right optical path of endoscope 1501 with the red filter and so right CCD 1533A captures red right image 1534R at time t. At time t+1, rotating filter 1533A filters light from the right optical path of endoscope 1501 with the green filter and so right CCD 1533A captures green right image 1535R at time t+1. At time t+2, rotating filter 1532B filters light from the right optical path of endoscope 1501 with the blue filter and so right CCD 1533A captures blue right image 1536R at time t+2. At time t+3, rotating filter 1532B filters light from the right optical path of endoscope 1501 with the fluorescence filter and so right CCD 1533A captures fluorescence right image 1537R at time t+3.

The capture process starts over at time t+4 in this aspect. In the example of FIG. 15, four frames are shown as being captured by the CCD sensor. This is for ease of illustration only and is not intended to be limiting. As is known, prior to capture of the frame, the previously captured frame in the CCD sensor could be moved to a buffer, for example, for the processing described more completely below.

In this example, the two light sources in combination light source were maintained continuously on. In another aspect, the white light source is held on for capture at times t, t+1, and t+2 and then turned off before the capture at time t+3. For the capture at time t+3, the laser is turned on. In this aspect, the fluorescence filter would not be used.

Time Division—Single Stereoscopic Optical Path with a Single CCD Camera Unit—Intelligent Image Processing System 130H Since the fluorescence and visible components images are captured at different instances of time, visible left image collector 1541 determines when three new frames of visible left image data are available and provides those three frames as a visible image frame to blend circuit 1551. Similarly, fluorescence left image collector 1543 determines when a new frame of fluorescence left image data is available and provides that frame as a fluorescence image to blend circuit 1551 Collector 1542 and collector 1544 operate similarly for the right images and provide the data to blend circuit 1552.

In one aspect, the capture frame rate is four times the normal video display rate and so the video display has the normal number of frames per second. However, this aspect can be used with a variety of frame rates. For example, the fluorescence capture frame rate could be some fraction of visible image capture frame rate. When a fluorescent frame is not captured for every RGB frame captured, the features of FIG. 9A could be used to process the data and generate artificial fluorescence frames, for example.

Time Division—Single Stereoscopic Optical Path with a Single CCD Camera Unit—Augmented Stereoscopic Display System 140H In one aspect, the augmented stereoscopic video output display may be operated in various modes. The operation of display mode select 1560, user interface 1593 and the interaction with blend circuit 1551, 1552 is the same as the above description for display mode select 360, user interface 393 and the interaction with blend circuit 351, 352 and that description is incorporated herein by reference.

The techniques previously described for enhancing the fluorescence image in the stereoscopic display are also applicable to this embodiment.

In all of the aspects described above, areas of fluorescence can be extracted from the images and identified with pseudo-coloring. Also, image processing to remove noise below a selected threshold may be performed to enhance image quality.

In one embodiment the IR filter from the CCD cameras is removed to increase sensitivity to the red and near IR wavelengths for improved fluorescence image capture.

In any of the various video capture aspects for the visible and fluorescence images described above, the frame rate can be varied to improve image capture. The visible images may be captured at standard video frame rates (e.g., 30 Hz) to provide acceptable images for the surgeon to see the tissue and the minimally invasive surgical tools in the stereoscopic video output at the surgeon's console. The frame rate for the fluorescence images may be at the same frame rate used for the visible images, or it may be slowed (e.g., 8 Hz) using the processes described above. Depending upon the optical paths and the cameras units used, various combinations of the processes described above can be used to generate any missing frames, either visible or fluorescence.

In some instances a slow frame rate is important to capture critical image information in weakly fluorescing regions. The slow frame rate allows more time for the camera/chip that is capturing the fluorescence images to receive the fluorescence energy from the excited fluorophores in the tissue of interest. The movable but steady endoscopic camera platform provided by a robotic surgical system is a significant benefit for the slow frame rate capture required for some fluorescence images. In contrast, a hand-held endoscope would produce low frame rate images that are blurred.

In some aspects, visible images and fluorescence images captured at different frame rates are synchronized in a manner similar to that described above by generating artificial fluorescence frames. In the case of stationary cameras, such as the endoscopic camera that is held stationary by the da Vinci® Surgical System platform, only small relative motions occur between camera and tissue, such as motion due to breathing. For these small motions, blur in the captured fluorescence images can be ignored in many situations. In the case of moving cameras, such as when the da Vinci® Surgical System endoscopic camera is moved by the robotic camera manipulator arm, temporal registration of visible images is first carried out to deblur the motion-blurred fluorescence images. Then, fluorescence images can be generated for image synchronization as described above.

As indicated above, since the fluorescence images show tissue of medical interest, the fluorescence images can be processed to enhance the surgeon's video display presentation. This processing produces an artificial fluorescence image. For example, the fluorescing regions in the fluorescence image may be artificially colored (pseudo-colored) using known methods. When the artificial fluorescence image is blended with the visible video image, the surgeon then sees the fluorescing tissue (e.g., artificially made bright green) in a high contrast to the surrounding tissue in the visible image. Different image blending options, such as alpha blending, of the pseudo color fluorescence images and visible images are made available.

In view of the above described aspects, knowledgeable persons understand that image sensors may be positioned outside the patient at the proximal end of the endoscope, or they may be placed at the distal end of the endoscope adjacent the tissue. Left and right stereoscopic images may be captured by separate chips or cameras, or they may be captured by different regions of a single chip in a single camera.

Although alternate imaging has been described in terms of fluorescence, other imaging modalities may be included. In some aspects, the visible image and the alternate image may be blended in a two-dimensional (single channel; monoscopic) image capture and display system.

The seamless blending of both visible and fluorescence images in real-time in a surgical robotic system provides a significant procedural benefit to the surgeon and a significant clinical benefit to the patient. The surgeon's ability to see fluorescing tissue of interest during surgery enhances both the precision and completeness of identifying and removing diseased tissue, and of identifying healthy tissue that should be preserved. For example, during prostate surgery some or all of the diseased prostate is removed, yet it is necessary to preserve adjacent nerves to avoid causing erectile dysfunction and/or urinary incontinence.

We claim:

1. An apparatus comprising:
    an endoscope held by a robotic surgical system, the endoscope comprising a stereoscopic optical channel;
    an image capture unit coupled to receive light via the stereoscopic optical channel;
    an image processing system coupled to receive images from the image capture unit;
    a stereoscopic display system coupled to display images received from the image processing system;
    a first image captured by the image capture unit at a first time and a second image captured by the image capture unit at a second time different from the first time, the first image comprising a combination of a first visible image and a first fluorescence image, the second image comprising a second visible image and no fluorescence image;
    an artificial fluorescence image, generated by the image processing system from the first fluorescence image;
    a first stereoscopic display image, generated by the image processing system from the first image, and output by the stereoscopic display system; and
    an augmented stereoscopic display image, generated by the image processing system from the second visible image and the artificial fluorescence image, and output by the stereoscopic display system.

2. The apparatus of claim 1,
    wherein the combined image comprises a stereoscopic image including a stereoscopic pair of images;
    wherein the stereoscopic pair of images includes:
        a first visible left image combined with a fluorescence left image; and
        a first visible right image combined with a fluorescence right image;
    wherein the fluorescence left and right images are the fluorescence image; and
    wherein the visible left image and visible right image are the first visible image.

3. The apparatus of claim 2 wherein the image processing system generates the artificial fluorescence image as an artificial stereoscopic pair of fluorescence images using the fluorescence left and right images captured at the first time.

4. The apparatus of claim 3:
    wherein the second visible image comprises a stereoscopic visible image including a second visible left image, and a second visible right image; and
    wherein the augmented stereoscopic image further comprises:
        a blend of the stereoscopic visible image captured at the second time and the artificial stereoscopic pair of fluorescence images.

5. The apparatus of claim 4 wherein the image processing system further comprises:
    an image warper coupled to receive the combined image, wherein the image warper converts the first visible right image combined with the fluorescence right image to a warped first visible right image combined with the fluorescence right image.

6. The apparatus of claim 5 wherein the image processing system further comprises:
    an image subtractor coupled to the image warper to receive the warped first visible right image combined with the fluorescence right image, and coupled to the capture unit to receive the second visible right image captured at the second time, wherein the image subtractor subtracts the second visible right image captured at the second time from the warped first visible right image combined with the fluorescence right image to generate an artificial fluorescence right image, wherein the artificial fluorescence right image is one image in the artificial stereoscopic pair of fluorescence images.

7. The apparatus of claim 5 wherein the image processing system further comprises:
    a synthesize fluorescence right image system coupled to said artificial fluorescence right image, wherein said synthesize fluorescence right image system uses said artificial fluorescence right image to generate a synthesized fluorescence right image.

8. The apparatus of claim 3 wherein the image processing system further comprises:
    a temporal image registration configured to temporally register the combined image and the second visible image.

9. The apparatus of claim 8 wherein the image processing system further comprises:
    an image warper coupled to said temporal image registration, wherein the image warper converts the first visible right image combined with the fluorescence right image captured at the first time to a warped image, wherein the warped image includes a warped visible right image combined with the fluorescence right image.

10. The apparatus of claim 1 wherein the endoscope further comprises an illumination channel, and the apparatus further comprises:
    a combination light source, coupled to the illumination channel, comprising:

a first light source for providing a first illumination light; and a second light source for providing a second illumination light, wherein the second illumination light is different from the first illumination light; and said second illumination light is synchronized with the capture of at least one of the first and second images.

11. The apparatus of claim 10 further comprising:
a fiber optic bundle connecting the illumination channel to the combination light source.

12. The apparatus of claim 11 wherein the second light source can be changed to a different light source while the at least fiber optic bundle remains connected to the illumination channel and to the combination light source.

13. The apparatus of claim 1:
wherein the first visible image includes a first stereoscopic left visible image and a first stereoscopic right visible image;
wherein the first fluorescence image includes a stereoscopic left fluorescence image and a stereoscopic right fluorescence image;
wherein the second visible image includes a second stereoscopic left visible image and a second stereoscopic right visible image;
wherein the artificial fluorescence image includes a stereoscopic left artificial fluorescence display image generated by the image processing system from the stereoscopic left fluorescence image, and includes a stereoscopic right artificial fluorescence display image generated by the image processing system from the stereoscopic right fluorescence image;
wherein the first stereoscopic display image includes a first stereoscopic left visible display image, generated by the image processing system from the first stereoscopic left visible image, combined with a first stereoscopic left fluorescence display image, generated by the image processing system from the stereoscopic left fluorescence image, and includes a first stereoscopic right visible display image, generated by the image processing system from the first stereoscopic right visible image, combined with a first stereoscopic right fluorescence display image, generated by the image processing system from the stereoscopic right fluorescence image; and
wherein the augmented stereoscopic display image includes a second stereoscopic left visible display image, generated by the image processing system from the second stereoscopic left visible image, combined with the stereoscopic artificial left fluorescence display image, and includes a second stereoscopic right visible display image, generated by the image processing system from the second stereoscopic right visible image, combined with the first stereoscopic artificial right fluorescence display image.

14. The apparatus of claim 1:
wherein the first time precedes the second time.

15. An apparatus comprising:
an endoscope held by a robotic surgical system, the endoscope comprising a stereoscopic optical channel;
an image capture unit coupled to receive light via the stereoscopic optical channel;
an image processing system coupled to receive images from the image capture unit;
a stereoscopic display system coupled to display images received from the image processing system;
a first image captured by the image capture unit at a first time and a second image captured by the image capture unit at a second time different from the first time, the first image comprising a first visible image and no fluorescence image, the second image comprising a combination of a second visible image and a fluorescence image;
an artificial fluorescence image, generated by the image processing system from the fluorescence image;
a first stereoscopic display image, generated by the image processing system from the first image, and output by the stereoscopic display system; and
an augmented stereoscopic display image, generated by the image processing system from the artificial fluorescence image and the first visible image, and output by the stereoscopic display system.

16. The apparatus of claim 15 wherein,
said first image comprises a visible first color component, a visible second color component, and a visible third color component; and
said second image comprises a visible first color component combined with said fluorescence image, a visible second color component, and a visible third color component.

17. The apparatus of claim 16 wherein said image processing system further comprises a fluorescence image and artifacts generator to generate (1) artifacts for said visible second and third color components, and (2) said fluorescence image plus artifacts for said visible first color component.

18. The apparatus of claim 17 wherein said image processing system further comprises a fluorescence image extractor coupled to said fluorescence image and artifacts generator, wherein said fluorescence image extractor generates a first fluorescence image for said second time.

19. The apparatus of claim 18 wherein said image processing system further comprises a fluorescence image enhancement system coupled to said fluorescence image generator wherein said fluorescence image enhancement system receives said first fluorescence image and generates said artificial fluorescence image.

20. A method comprising:
capturing at a first time, a first image from light from a stereoscopic optical path in an endoscope held and positioned by a robotic surgical system, wherein the light is from tissue;
capturing at a second time different from the first time, a second image from the light wherein the first image is a combined image including a combination of a fluorescence image and a first visible image, and the second image is a second visible image;
generating an artificial fluorescence image using the captured fluorescence image; and
generating an augmented stereoscopic image of at least a portion of the tissue, the augmented stereoscopic image comprising the artificial fluorescence image and the second visible image.

21. The method claim 20,
wherein the combined image comprises a stereoscopic image including a stereoscopic pair of images;
wherein the stereoscopic pair of images includes:
a visible left image combined with the fluorescence left image, and
a visible right image combined with the fluorescence right image;
wherein the fluorescence left and right images are the fluorescence image; and
wherein the visible left image and visible right image are the first visible image.

* * * * *